(12) United States Patent
Linden et al.

(10) Patent No.: US 6,545,002 B1
(45) Date of Patent: Apr. 8, 2003

(54) SUBSTITUTED 8-PHENYLXANTHINES USEFUL AS ANTAGONISTS OF $A_{2B}$ ADENOSINE RECEPTORS

(75) Inventors: Joel M. Linden, Charlottesville, VA (US); Kenneth A. Jacobson, Silver Spring, MD (US); Yong-Chul Kim, Hoover, AL (US)

(73) Assignees: University of Virginia Patent Foundation, Charlottesville, VA (US); National Institutes of Health, Rockville, MD (US)

( * ) Notice: Subject to any disclaimer, the term of this patent is extended or adjusted under 35 U.S.C. 154(b) by 0 days.

(21) Appl. No.: 09/505,504

(22) Filed: Feb. 17, 2000

Related U.S. Application Data

(60) Provisional application No. 60/136,898, filed on Jun. 1, 1999, provisional application No. 60/136,900, filed on Jun. 1, 1999, and provisional application No. 60/151,875, filed on Aug. 31, 1999.

(51) Int. Cl.[7] .................... C07D 473/06; A61K 31/522; A61P 3/10; A61P 1/12; A61P 27/02

(52) U.S. Cl. ................ 514/263.2; 514/263.2; 514/263.34; 544/269; 544/270; 544/271

(58) Field of Search ................. 544/271, 269, 544/270; 514/263, 265, 263.2, 263.22, 263.34

(56) References Cited

U.S. PATENT DOCUMENTS

| | | | |
|---|---|---|---|
| 4,452,788 A | 6/1984 | Bristol | 424/253 |
| 4,612,315 A | 9/1986 | Jacobson et al. | 514/263 |
| 4,696,932 A | 9/1987 | Jacobson et al. | 514/263 |
| 5,298,508 A | 3/1994 | Jacobson et al. | 514/263 |
| 5,300,298 A | 4/1994 | LaNoue | 424/442 |
| 5,443,836 A * | 8/1995 | Downey | 424/423 |
| 5,446,046 A | 8/1995 | Beladrinelli et al. | 514/263 |
| 5,776,940 A * | 7/1998 | Daluge | 544/271 |
| 5,854,081 A | 12/1998 | Linden et al. | 436/501 |
| 5,932,558 A | 8/1999 | Cronstein et al. | 514/46 |
| 6,060,481 A | 5/2000 | LaNoue et al. | 514/263 |
| 6,437,124 B1 * | 8/2002 | Daluge et al. | 544/271 |

FOREIGN PATENT DOCUMENTS

| | | |
|---|---|---|
| EP | 0203721 | 12/1986 |
| EP | 0374808 | 12/1989 |
| WO | 99/42093 | 8/1999 |

OTHER PUBLICATIONS

Alexander, S.P., et al., "Characterization of the human brain putative $A_{2B}$ adenosine receptor expressed in Chinese hamster ovary (CHO.$A_{2B4}$) cells", *British Journal of Pharmacology*, 119, pp. 1286–1290, (1996).

Auchampach, J.A., et al., "Canine Mast Cell Adenosine Receptors: Cloning and Expression of the $A_3$ Receptor and Evidence that Degranulation is Mediated by the $A_{2B}$ Receptor", *Molecular Pharmacology*, 52 (5), pp. 846–860, (1997).

Barcz, E., et al., "The influence of theobromine on angiogenic activity and proangiogenic cytokines production of human ovarian cancer cells", *Oncology Reports*, 5 (2), pp. 517–520, (1998).

Barnes, P.J., et al., "Theophylline in the Management of Asthma: Time for Reappraisal?", *European Respiratory Journal*, 7, pp. 579–591, (1994).

Biaggioni, I., et al., "Adenosine Produces Pulmonary Vasoconstriction in Sheep: Evidence for Thromboxane $A_2$/Prostaglandin Endoperoxide–receptor Activation", *Circulation Research*, 65 (6), pp. 1516–1525, (Dec. 1989).

Björk, T., et al., "Isolated Bronchi from Asthmatics are Hyperresponsive to Adenosine, which Apparently Acts Indirectly by Liberation of Leukotrienes and Histamine", *Am. Rev. Respir. Dis*, 145, pp. 1087–1091, (1992).

Brackett, L.E., et al., "Functional Characterization of the $A_{2b}$ Adenosine Receptor in NIH 3T3 Fibroblasts", *Biochemical Pharmacology*, 47 (5), pp. 801–814, (1994).

Bridges, A.J., et al., "$N^6$–[2–(3,5–Dimethoxyphenyl)–2–(2–Methylphenyl)–Ethyl]Adenosine and Its Uronamide Derivatives. Novel Adenosine Agonists With Both High Affinity and High Selectivity for the Adenosine $A_2$ Receptor", *Journal of Medicinal Chemistry*, 31 (7), pp. 1282–1285, (1988).

(List continued on next page.)

*Primary Examiner*—Mark L. Berch
(74) *Attorney, Agent, or Firm*—Schwegman, Lundberg, Woessner & Kluth, P.A.

(57) ABSTRACT

The present invention provides compounds having the formula I:

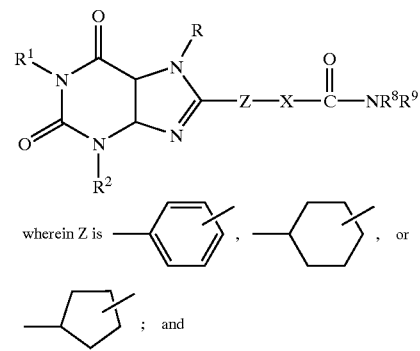

X is $(C_1-C_8)$alkylene, $(C_2-C_8)$alkenylene, $(C_2-C_8)$ alkynylene, wherein one of the carbon atoms in the alkylene, alkenylene or alkynylene groups is optionally replaced with a group having the formula —O—, —N($R^4$)C(O)—, —OC(O—, S—, —S(O)—or —$SO_2$—, or a pharmaceutically acceptable salt thereof and pharmaceutical compositions comprising compounds having the formula I. The compounds of the invention are selective antagonists of $A_{2B}$ adenosine receptors (ARs). These compounds and compositions are useful as pharmaceutical agents for treatment of diseases that are mediated by $A_{2B}$ adenosine receptors.

27 Claims, 8 Drawing Sheets

OTHER PUBLICATIONS

Bruns, R.F., "Adenosine Antagonism by Purines, Pteridines and Benzopteridines in Human Fibroblasts", *Biochemical Pharmacology*, 30, pp. 325–333, (1981).

Bruns, R.F., "Adenosine Receptors—Roles and Pharmacology", *Biological Actions of Extracellular ATP*, 603, Annals of The New York Academy of Sciences, pp. 211–226, (1990).

Bruns, R.F., et al., "Adenosine receptor binding: Structure–activity analysis generates extremely potent xanthine antagonists", *Proceedings of the National Academy of Sciences*, 80 (7), pp. 2077–2080, (Apr. 1983).

Bruns, R.F., et al., "Binding of the $A_1$–selective adenosine antagonist 8–cyclopentyl–1,3–dipropylxanthine to rat brain menbranes", *Naunyn–Schmiedeberg's Archives of Pharmacology*, pp. 59–63, (1987).

Bruns, R.F., et al., "Characterization of the $A_2$ Adenosine Receptor Labeled by [$^3$H]NECA in Rat Striatal Membranes", *Molecular Pharmacology*, 29, pp. 331–346, (1986).

Buster, B., et al., "The Effect of Adenosine Receptor Agonists on Neutrophil Pleocytosis and Blood–Brain Barrier Pathophysiology in Experimental Bacterial Meningitis", *Abstract of the Interscience Conference on Antimicrobial Agents and Chemotherapy*, 37, Abstract No. B–72, p. 39, (1997).

Chapman, K.R., et al., "Long–Term Xanthine Therapy of Asthma—Enprofylline and Theophylline Compared", *Chest*, 106 (5), pp. 1407–1413, (Nov. 1994).

Cheng, Y., et al., "Relationship Between the Inhibition Constant ($K_i$) and the Concentration of Inhibitor Which Causes 50 Per Cent Inhibition ($I_{50}$) of an Enzymatic Reaction", *Biochemical Pharmacology*, 22 (23), pp. 3099–3108, (Dec. 1, 1973).

Clancy, J.P., et al., "Adenosine and its nucleotides activate wild–type and R117H CFTR through an $A_{2B}$ receptor–coupled pathway", *American Journal of Physiology*, 276 (Issue 2), Cell Physiology, pp. C361–C369, (Feb. 1999).

Clarke, H., et al., "The Protective Effects of Intravenous Theophylline and Enprofylline against Histamine– and Adenosine 5'–Monophosphate–provoked Bronchoconstriction : Implications for the Mechanisms of Action of Xanthine Derivatives in Asthma", *Pulmonary Pharmacology*, 2, pp. 147–154, (1989).

Cooper, J., et al., "An endogenous $A_{2B}$ adenosine receptor coupled to cyclic AMP generation in human embryonic kidney (HEK 293) cells", *British Journal of Pharmacology*, 122, pp. 546–550, (1997).

Crist, G.H., et al., "Tissue–Specific effects of in vivo adenosine receptor blockade on glucose uptake in Zucker rats", *The FASEB Journal*, 12, pp. 1301–1308, (Oct. 1998).

Cristalli, G., et al., "2–Alkynyl Derivatives of Adenosine an Adenosine–5'–N–ethyluronamide as Selective Agonists at $A_2$ Adenosine Receptors1", *Journal of Medicinal Chemistry*, 35 (13), pp. 2363–2368, (1992).

Cristalli, G., et al., "Characterization of Potent Ligands at Human Recombinant Adenosine Receptors", *Drug Development Research*, 45, Research Overview, pp. 176–181, (1998).

Cronstein, B.N., et al., "Adenosine; A Physiologic Modulator Of Superoxide Anion Generated By Human Neutrophils. Adenosine Acts Via An $A_2$ Receptor On Human Neutrophils", *Journal Of Immunology*, 135 (2), pp. 1366–1371, (1985).

Cronstein, B.N., et al., "Methotrexate Inhibits Leukocyte Influx Into Inflammatory Sites Via The Adenosine ($A_2$) Receptor", *Clinical Research*, 41 (2), p. 244A, (1993).

Cronstein, B.N., et al., "The Adenosine/Neutrophil Paradox Resolved: Human Neutrophils Possess Both $A_1$ and $A_2$ Receptors That Promote Chemotaxis and Inhibits $O_2$ Generation, Respectively", *Journal of Clinical Investigation*, 85 (4), pp. 1150–1157, (1990).

Cronstein, N., et al., "Occupancy Of Adenosine Receptors Raises Cyclic AMP Alone And In Synergy With Occupancy Of Chemoattractant Receptors And Inhibits Membrane Depolarization", *Biochemical Journal*, 252 (3), pp. 709–715, (1988).

Cushley, M.J., et al., "Adenosine–induced Bronchoconstriction in Asthma. Antagonism by Inhaled Theophylline", *American Review of Respiratory Disease*, 129 (3), pp. 380–384, (Mar. 1984).

Cushley, M.J., et al., "Adenosine–induced bronchoconstriction in asthma: Role of mast cell–mediator release", *J. Allergy Clin. Immunol.*, 75 (2), pp. 272–278, (Feb. 1985).

Daly, J.W., et al., "Molecular Probes for Adenosine Receptors", *In: The Nervous System*, J.A. Ribiero, ed., Taylor & Francis, London, pp. 41–52, (1989).

Daly, J.W., et al., "Subclasses of Adenosine Receptors in the Central Nervous System: Interaction with Caffeine and Related Methylxanthines", *Cellular and Molecular Neurobiology*, 3 (1), pp. 69–80, (1983).

de Zwart, M., et al., "A Functional Screening of Adenosine Analogues at the Adenosine $A_{2B}$ Receptor: A Search For Potent Agonists", *Nucleosides & Nucleotides*, 17 (6), pp. 969–985, (1998).

de Zwart, M., et al., "Potent Antagonists for the Adenosine $A_{2B}$ Receptor. II. Triazolotriazines with High Affinity", *Ferrara Abstracts*, Abstract No. 107, 1 p., (1998).

Doyle, M.P., et al., "Nucleotide–induced Arteriolar Constriction: a Mast Cell–dependent Response.", *American Journal of Physiology*, pp. H2042–H2050, (May 1994).

Drazen, J.M., et al., "Treatment of Asthma with Drugs Modifying the Leukotriene Pathway", *Drug Therapy, Review Article*, 340 (3), pp. 197–206, (Jan. 21, 1999).

Felgner, P.L., et al., "Lipofection: A highly efficient, lipid–mediated DNA–transfection procedure", *Proceedings of the National Academy of Sciences*, 84, Biochemistry, pp. 7413–7417, (Nov. 1987).

Feoktistov, I., et al., "Adenosine $A_{2b}$ receptors", *The American Society for Pharmacological and Experimental Therapeutics*, 49 (4), pp. 381–402, (1987).

Feoktistov, I., et al., "Adenosine $A_{2b}$ Receptors Evoke Interleukin–8 Secretion in Human Mast Cells—An Enprofylline–Sensitive Mechanism with Implications for Asthma", *The Journal of Clinical Investigation*, 96, pp. 1979–1986, (1995).

Feoktistov, I., et al., "Role of Adenosine in Asthma", *Drug Development Research*, 39, pp. 333–336, (1996).

Feoktistov, I., et al., "Role of p38 Mitogen–Activated Protein Kinase and Extracellular Signal–Regulated Protein Kinase Kinase in Adenosine $A_{2B}$ Receptor–Mediated Interleukin–8 Production in Human Mast Cells", *Molecular Pharmacology*, 55, pp. 726–734, (1999).

Forsythe, P., et al., "Adenosine, mast cells, and asthma", *Inflammation Research*, 48, pp. 301–307, (1999).

Francis, J.E., et al., "Highly Selective Adenosine $A_2$ Receptor Agonists in a Series of N–Alkylated 2–Aminoadenosines", *Journal of Medicinal Chemistry*, 34 (8), pp. 2570–2579, (1991).

Fredholm, B.B., et al., "Actions of Caffeine in the Brain with Special Reference to Factors That Contribute to Its Widespread Use", *Pharmacological Reviews*, 51 (1), pp. 83–133, (1999).

Furlong, T.J., et al., "Molecular characterization of a human brain adenosine $A_2$ receptor", *Molecular Brain Research*, 15 (1,2), pp. 62–66, (Sep. 1992).

Gao, Z., et al., "$A_{2B}$ Adenosine and $P2Y_2$ Receptors Stimulate Mitogen–activated Protein Kinase in Human Embryonic Kidney–293 Cells. Cross–talk Between Cyclic AMP and Protein Kinase c Pathways", *The Journal of Biological Chemistry*, 274 (9), pp. 5972–5980, (Feb. 26, 1999).

Grant, M.B., et al., "Adenosine Receptor Activation Induces Vascular Endothelial Growth Factor in Human Endothelial Cells", *Circulation Research*, 85, pp. 699–706, (1999).

Griswold, D.E., et al., "Effects of Selective Phosphodiesterase Type IV Inhibitor, Rolipram, on Fluid and Cellular Phases of Inflammatory Response", *Chemical Abstracts*, 119, Abstract No. 173828e, p. 49, (1993).

Hannon, J.P., et al., "A Role for Mast Cells in Adenosine $A_3$ Receptor–Mediated Hypotension in the Rat", *British Journal of Pharmacology*, 115 (6), pp. 945–952, (Jul. 1995).

Hussain, T., et al., "$^{125}$I–APE Binding to Adenosine Receptors in Coronary Artery: Photoaffinity Labeling With $^{125}$I–azidoAPE", *The Journal of Pharmacology and Experimental Therapeutics*, 276 (1), pp. 284–288, (Jan. 1996).

Hutchison, A.J., et al., "2–(Arylalkylamino)Adenosine–5'–Uronamides: A New Class of Highly Selective Adenosine $A_2$ Receptor Ligands", *Journal of Medicinal Chemistry*, 33 (7), pp. 1919–1924, (1990).

Hutchison, A.J., et al., "CGS 21680C, an $A_2$ Selective Adenosine Receptor Agonist With Preferential Hypotensive Activity", *The Journal of Pharmacology and Experimental Therapeutics*, 251 (1), pp. 47–55, (1989).

Iannone, M.A., et al., "Effects of Adenosine on Human Neutrophil Function and Cyclic AMP Content", *In: Topics and Perspectives in Adenosine Research*, Eds. E. Gerlach et al., Springer–Verlag, Berlin, Germany, pp. 286–298, (1986).

Jacobson, K.A., et al., "1,3–Dialkylxanthine Derivatives Having High Potency as Antagonists at Human $A_{2B}$ Adenosine Receptors", *Drug Development Research*, 47, Research Article, pp. 45–53, (1999).

Jacobson, K.A., et al., "8–Substituted Xanthines as Antagonists at $A_1$– and $A_2$–Adenosine Receptors", *Biochemical Pharmacology*, 37 (19), pp. 3653–3661, (1988).

Jacobson, K.A., et al., "A Functionalized Cogener Approach to Adenosine Receptor Antagonists: Amino Acid Conjugates of 1,3–Dipropylxanthine", *Molecular Pharmacology*, 29, pp. 126–132, (1985).

Jacobson, K.A., et al., "Development of Selective Purinoceptor Agonists and Antagonists", *In: Purinergic Approaches in Experimental Therapeutics*, Chapter 6, Edited by K.A. Jacobson et al., Wiley–Liss, Inc., pp. 101–128, (1997).

Jacobson, K.A., et al., "Electrophilic Derivatives of Purines as Irreversible Inhibitors of $A_1$ Adenosine Receptors", *Journal of Medicinal Chemistry*, 32 (5), pp. 1043–1051, (1989).

Jacobson, K.A., et al., "Functionalized Cogeners of 1,3–Dialkylxanthines: Preparation of Analogues with High Affinity for Adenosine Receptors", *Journal of Medicianl Chemistry*, 28 (9), pp. 1334–1340, (Sep. 1985).

Jacobson, K.A., et al., "Probing the adenosine receptor with adenosine and xanthine biotin conjugates", *Federation of European Biomedical Societies*, 184 (1), pp. 30–35, (May 1985).

Jacobson, K.A., et al., "Stimulation by Alkylxanthines of Chloride Efflux in CFPAC–1 Cells Does Not Involve $A_1$ Adenosine Receptors", *Biochemistry*, 34 (28), pp. 9088–9094, (1995).

Jacobson, K.A., et al., "Structure–Activity Relationships of 8–Styrylxanthines as $A_2$–Selective Adenosine Antagonists", *Journal of Medicinal Chemistry*, 36 (10), pp. 1333–1342, (1993).

Jacobson, K.A., et al., "Sulfur–Containing 1,3–Dialkylxanthine Derivatives as Selective Antagonists at $A_1$–Adenosine Receptors", *Journal of Medicinal Chemistry*, 32 (8), pp. 1873–1879, (1989).

Jacobson, K.A., et al., "Xanthine Functionalized Congeners as Potent Ligands at A2–Adenosine Receptors", *Journal of Medicinal Chemistry*, 30 (1), pp. 211–214, (Jan. 1987).

Jarvis, M.F., et al., "[$^3$H]CGS 21680, A Selective $A_2$ Adenosine Receptor Agonist Directly Labels $A_2$ Receptors in Rat Brain.", *Journal of Pharmacology and Experimental Therapeutics*, 251(3), pp. 888–893, (Dec. 1989).

Ji, X., et al., "Use of the Triazolotriazine [$^3$H] ZM 241385 as a Radioligand at Recombinant Human $A_{2B}$ Adenosine Receptors", *Drug Design and Discovery*, 16, pp. 217–226, (1999).

Jiang, Q., et al., "Mutagenesis Reveals Structure–Activity Parallels between Human $A_{2A}$ Adenosine Receptors and Biogenic Amine G Protein–Coupled Receptors", *Journal of Medicinal Chemistry*, 40 (16), pp. 2588–2595, (1997).

Jin, X., et al., "Inosine Binds to $A_3$ Adenosine Receptors and Stimulates Mast Cell Degranulation", *The Journal of Clinical Investigation*, 100 (11), pp. 2849–2857, (1997).

Kim, H.O., et al., "Structure–Activity Relationships of 1,3–Dialkylxanthine Derivatives at Rat $A_3$ Adenosine Receptors", *Journal of Medicinal Chemistry*, 37 (20), pp. 3373–3382, (Sep. 30, 1994).

Kim, Y., et al., "Acyl–Hydrazide Derivatives of a Xanthine Carboxylic Congener (XCC) as Selective Antagonists at Human $A_{2b}$ Adenosine Receptors", *Drug Development Research*, 47, Research Article, pp. 178–188, (1999).

Kim, Y., et al., "Derivatives of the Triazoloquinazoline Adenosine Antagonist (CGS 15943) Having High Potency at the Human $A_{2B}$ and $A_3$ Receptor Subtypes", *Journal of Medicinal Chemistry*, 41 (15), pp. 2835–2845, (1998).

Kohno, Y., et al., "Activation of $A_3$ Adenosine Receptors on Human Eosinophils Elevates Intracellular Calcium", *Blood*, 88 (9), pp. 3569–3574, (Nov. 1, 1996).

Kollias–Baker, C., et al., "Allosteric Enhancer PD 81,723 Acts by Novel Mechanism to Potentiate Cardiac Actions of Adenosine", *Circulation Research*, 75 (6), pp. 961–971, (Dec. 1994).

Konduri, G.G., et al., "Adenosine Is a Pulmonary Vasodilator in Newborn Lambs", *American Review of Respiratory Disease*, 146 (3), pp. 670–676, (Sep. 1992).

Lichtensein, L.M., "Allergy and the Immune System", *Scientific American*, Special Issue, pp. 117–124, (Sep. 1993).

Linden, J., "Allosteric Enhancement of Adenosine Receptors", *In: Purinergic Approaches in Experimental Therapeutics*, Chapter 5, Edited by K.A. Jacobson et al., and Published by Wiley–Liss, Inc., pp. 85–97, (1997).

Linden, J., "Calculating the Dissociation Constant of an Unlabeled Compound from the Concentration Required to Displace Radiolabel Binding by 50%", *Journal of Cyclic Nucletide Research*, 8 (3), pp. 163–172, (1982).

Linden, J., "Cloned Adenosine $A_3$ Receptors: Pharmacological Properties, Species Differences and Receptor Functions.", *Trends in Pharmacological Sciences*, 15 (8), pp. 298–306, (Aug. 1994).

Linden, J., "Molecular Characterization of $A_{2A}$ and $A_{2B}$ Adenosine Receptors (AR)", *Drug Development Research*, 43 (1), Ferrara Abstract No. 7, 1 p., (Jan. 1998).

Linden, J., et al., "$^{125}$I–Labeled 8–Phenylxanthine Derivatives: Antagonist Radioligands for Adenosine $A_1$ Receptors", *Journal of Medicinal Chemistry*, 31 (4), pp. 745–751, (Apr. 1988).

Linden, J., et al., "Characterization of Human $A_{2B}$ Adenosine Receptors: Radioligand Binding, Western Blotting, and Coupling to Gq in Human Embryonic Kidney 293 Cells and HMC–1 Mast Cells", *Molecular Pharmacology*, 56, pp. 705–713, (1999).

Linden, J., et al., "Molecular Biology and Pharmacology of Recombinant Adenosine Receptors", *In: Cardiovascular Biology of Purines*, Eds: G. Burnstock, et al., Kluwer Publishers, pp. 1–20, (1998).

Linden, J., et al,. "The Structure and Function of $A_1$ and $A_{2B}$ Adenosine Receptors", *Life Science*, 62 (17/18), pp. 1519–1524, (1998).

Lunell, E., et al., "Effects of Enprofylline, a Xanthine Lacking Adenosine Receptor Antagonism, in Pateitns with Chronic Obstructive Lung Disease", *European Journal of Clinical Pharmacology*, 22, pp. 395–402, (1982).

Luthin, D.R., et al., "Characterization of Two Affinity States of Adenosine $A_{2a}$ Receptors With a New Radioligand, 2–[2–(4–amino–3–[$^{125}$I]iodophenyl) Ethylamino]Adenosine.", *Molecular Pharmacology*, 47 (2), pp. 307–313, (Feb. 1995).

Luthin, D.R., et al., "Comparison of $A_4$ and $A_{2a}$ Binding Sites in Striatum and COS Cells Transfected With Adesosine $A_{2a}$ Receptors.", *The Journal of Pharmacology and Experimental Therapeutics*, 272, pp. 511–518, (Feb. 1995).

Marquardt, D.L., et al., "Potentiation of Mast Cell Mediator Release by Adenosine", *The Journal of Immunology*, 120 (3), pp. 871–878, (Mar. 1978).

Marquardt, D.W., "An Algorithm for Least–Squares Estimation of Nonlinear Parameters", *Journal of the Society for Industrial and Applied Mathematics*, 11 (2), pp. 431–441, (Jun. 1963).

Martin, P.J., et al., "2–Phenylethoxy–9–Methyladenine: An Adenosine Receptor Antagonist That Discriminates between $A_2$ Adenosine Receptors in the Aorta and the Coronary Vessels from the Guinea Pig", *The Journal of Pharmacology and Experimental Therapeutics*, 265 (1), pp. 248–253, (1993).

Mino, R.P., et al., "Adenosine $A_{2b}$ Receptor Inhibition Decreases Retinal Neovascularization In Mice With Oxygen Induced Retinopathy", *The Association for Research in Vision and Ophthalology (ARVC)*, www.arvo.org/arvo/arvo00/50936w.gif, 2 p., (Mar. 1, 2000).

Neary, J.T., et al., "Trophic actions of extracellular nucleotides and nucleosides on glial and neuronal cells", *Trends in Neurosciences*, 19 (1), pp. 13–18, (1996).

Newman, K.D., et al., "Adenovirus–mediated Gene Transfer into Normal Rabbit Arteries Results in Prolonged Vascular Cell Activation, Inflammation and Neointimal Hyperplasia", *Journal of Clinical Investigation*, 96 (6), pp. 2955–2965, (1995).

Niiya, K., et al., "2–(N'–Alkylidenehydrazino) Adenosines: Potent and Selective Coronary Vasodilators", *Journal of Medicinal Chemistry*, 35 (24), pp. 4557–4561, (1992).

Nolte, "Reduction of Postischemic Leukocyte–Endothelium Interaction by Adenosine Via $A_2$ Receptor", *Biological Abstract*, 94 (11), Abstract No. 116779, 1 p., (1992).

Nyce, J.W., et al., "DNA antisense therapy for asthma in an animal model", *Nature*, 385, pp. 721–725, (Feb. 20, 1997).

O'Regan, M.H., et al., "Adenosine Receptor Agonists Inhibit the Release of γ–Aminobutyric Acid (GABA) From the Ischemic Rat Cerebral Cortex", *Chemical Abstracts*, 117, Abstract No. 104867p, p. 170, (1992).

Olah, M.E., et al., "$^{125}$I–4–Aminobenzyl–5'–N–methylcarboxamidoadenosine, a High Affinity Radioligand for the Rat $A_3$ Adenosine Receptor", *Molecular Pharmacology*, 45, pp. 978–982, (1994).

Olsson, R.A., et al., "$N^6$ Substituted N–Alkyladenosine–5'–Uronamides: Bifunctional Ligands Having Recognition Groups for A1 and A2 Adenosine Receptors", *Journal of Medicinal Chemistry*, 29 (9), pp. 1683–1689, (1986).

Palmer, T.M., et al., "$^{125}$I–4–(2–[7–Amino–2–{2–fury}{1,2,4}triazolo{2,3–a} {1,3,5}triazin–5–yl–amino]ethyl)phenol, a High Affinity Antagonist Radioligand Selective for the $A_{2a}$ Adenosine Receptor", *Molecular Pharmacology*, 48 (6), pp. 970–974, (Dec. 1995).

Papesch, V., et al., "Synthesis of 1–Mono– and 1,3–Di–S-ubstituted 6–Amino–Uracils. Diuretic Activity", *The Journal of Organic Chemistry*, 16 (7), pp. 1879–1890, (Jul. 1951).

Peet, N.P., et al., "A Novel Synthesis of Xanthines: Support for a New Binding Mode for Xanthines with Respect to Adenosine at Adenosine Recetors", *Journal of Medicinal Chemistry*, 33 (12), pp. 3127–3130, (Dec. 1990).

Peet, N.P., et al., "Conformationally Restrained, Chiral (Phenylisopropyl) Amino–Substituted Pyrazolo[3,4–d]Pyrimidines and Purines With Selectivity for Adenosine $A_1$ and $A_2$ Receptors", *Journal of Medicinal Chemistry*, 35 (17), pp. 3263–3269, (1992).

Pfister, J.R., et al., "Synthesis and Biological Evaluation of the Enantiomers of the Potent and Selective $A_1$– adenosine Antagonist 1,3–dipropyl–8–[2–(5,6–epoxynorbonyl)]–xanthine", *Journal of Medicinal Chemistry*, 40(12), pp. 1773–1778, (Jun. 1997).

Pierce, K.D., et al., "Molecular Cloning and Expression of an Adenosine $A_{2b}$ Receptor from Human Brain", *Biochemical and Biophysical Research Communications*, 187 (1), pp. 86–93, (Aug. 31, 1992).

Remkumar, V., et al., "The $A_3$ Adenosine Receptor is the Unique Adenosine Receptor which Facilitates Release of Allergic Mediators in Mast Cells", *The Journal of Biological Chemistry*, 268 (23), pp. 16887–16890, (Aug. 15, 1993).

Raud, J., "Intravial Microscopic Studies on Acute Mast Cell–Dependent Inflammation", *In: Acta Physiologica Scandinavica*, 135, Supplementum 578, Published for the Scandinavian Physiological Society, Blackwell Scientific Publications, pp. 1–58, (1989).

Resnick, M.B., et al., "Activated Eosinophils Evoke Chloride Secretion in Model Intestinal Epithelia Primarily via Regulated Release of 5'–AMP", *The Journal of Immunology*, 151 (10), pp. 5716–5723, (Nov. 15, 1993).

Robeva, A.S., et al., "Double Tagging Recombitant $A_1$– and $A_{2A}$–Adenosine Receptors With Hexahistidine and the Flag Epitope. Development of an Efficient Generic Protein Purification Procedure.", *Biochemical Pharmacology*, 51(4), pp. 545–555, (Feb. 1996).

Robeva, A.S., et al., "Molecular Characterization of Recombinant Human Adenosine Receptors", *Drug Development Research*, 39, pp. 243–252, (1996).

Rosenblum, W.I., "A Possible Role for Mast Cells in Controlling the Diameter of Arterioles on the Surface of the Brain", *Brain Research*, 49, pp. 75–82, (1973).

Rosin, D.L., et al., "Immunohistochemical Localization of Adenosine $A_{2A}$ Receptors in the Rat Central Nervous System", *The Journal of Comparative Neurology*, 401, pp. 163–186, (1998).

Salvatore, C.A., et al., "Molecular Cloning and Characterization of the Human $A_3$ Adenosine Receptors", *Proceeding of the National Academy of Sciences*, 90 (21), pp. 10365–10369, (Nov. 1, 1993).

Schlack, et al., "Adenosine $A_2$ –Receptor Activation at Reperfusion reduces Infarct Size and Improves Myocardial Wall Function in Dog Heart", *Biological Abstract*, 96 (6), Abstract No. 67801, 1 p., (1993).

Schrier, D.J., et al., "Effects of Adenosine Agonists on Human Neutrophil Function", *Journal of Immunology*, 137 (10), pp. 3284–3289, (1986).

Schwabe, U., et al., "Characterization of Adenosine Receptors in Rat Brain by (-) [$^3$H]$N^6$–Phenylisopropyladenosine", *Archives of Phrmacology*, 313 (3), pp. 179–187, (Sep. 1980).

Shamin, M.T., et al., "Effects of 8–Phenyl and 8–Cycloalkyl Substituents on the Activity of Mono–, Di–, and Trisubstituted Alkylxanthines with Substitution at the 1–,3–, and 7–Positions", *Journal of Medicinal Chemistry*, 32 (6), pp. 1231–1237, (1989).

Shepard, R.K., et al., "Adenosine–Induced Vacoconstriction In Vitro. Role of the Mast Cell and $A_3$ Adenosine Receptor", *Circulation Research*, 78 (4), pp. 627–634, (Apr. 1996).

Smits, P., et al., "Cardiovascular effects of two xanthines and the relation to adenosine antagonism", *Clinical Pharmacology and Therapeutics*, 45 (6), pp. 593–599, (1989).

Stehle, J.H., et al., "Molecular Cloning and Expression of cDNA for a Novel $A_2$–Adenosine Receptor Subtype", *Molecular Endocrinology*, pp. 384–393, (1992).

Stowell, C.P., et al., "A Fluorescamine Assay for Submicrogram Quantities of Protein in the Presence of Triton X–100", *ANalytical Biochemistry*, 85 (85), pp. 572–580, (1978).

Strohmeier, G.R., et al., "The $A_{2b}$ Adenosine Receptor Mediates cAMP Responses to Adenosine Receptor Agonists in Human Intestinal Epithela", *The Journal of Bioligical Chemistry*, 270 (5), pp. 2387–2394, (Feb. 3, 1995).

Ueeda, M., et al., "2– Alkoxyadenosines: Potent and Selective Agonists at the Coronary Artery $A_2$ Adenosine Receptor", *Journal of Medicinal Chemistry*, 34(4), pp. 1334–1339, (1991).

Ukena, D., et al., "Species Differences in Structure–Activity Relationships of Adenosine Agonists and Xanthine Antagonists at Brain A1 Adenosine Receptors", *FEBS Letters*, 209 (1), pp. 122–128, (Dec. 1986).

Van Calker, D., et al., "Carbamazepine Distinguishes Between Adenosine Receeotors That Mediate Different Second Messenger Responses", *European Journal of Pharmacology*, 206 (4), pp. 285–290, (1991).

Van der Wenden, E.M., et al., "8–Substituted adenosine and theophylline–7–riboside analogues as potential partial agonists for the adenosine $A_1$ receptor", *European Journal of Pharmacology, Molecular Pharmacology Section 290*, pp. 189–199, (1995).

Nassallo, R., et al., "Theophylline: Recent Advances in the Understanding of Its Mode of Action and Uses in Clinical Practice", *Mayo Clin. Proc.*, 76, Review, pp. 346–354, (Apr. 1998).

Yoneyama, F., et al., "Vasodepressor Mechanisms of 2–(1–octynyl) –Adenosine (YT–146), a Selective Adenosine $A_2$ Receptor Agonist, Involve the Opening of Glibenclamide–sensitive $K^+$ Channels", *European Journal of Pharmacology*, 213 (1), pp. 199–204, (1992).

Zhou, Q.Y., et al., "Molecular Cloning and Characterization of an Adenosine Receptor: the A3 Adenosine Receptor", *Proceedings of the National Academy of Sciences*, 89 (16), pp. 7432–7436, (Aug. 15, 1992).

\* cited by examiner

1, R = H

2, R = Ph

3, Enprofylline

4a, R' = OH
4b, R' =

4c, R' =

4d, R' = NH(CH$_2$)$_2$NH$_2$

4a, X=OCH$_2$
4g, X=CH=CH

R$^3$ = aliphatic or aromatic amines

SUBSTITUTED 8-PHENYLXANTHINES USEFUL AS ANTAGONISTS OF $A_{2B}$ ADENOSINE RECEPTORS

CROSS-REFERENCE TO RELATED APPLICATIONS

This application claims priority of U.S. provisional patent applications Ser. Nos. 60/136,898 filed Jun. 1, 1999, and No. 60/136,900 filed Jun. 1, 1999, No. 60/151,875 filed Aug. 31, 1999.

GOVERNMENT FUNDING

The invention described herein was made with government support under Grant Numbers HL37942 and HL56111 awarded by the National Institute of Health. The United States Government has certain rights in the invention.

FIELD OF THE INVENTION

The present invention relates to compounds and pharmaceutical compositions that are selective antagonists of $A_{2B}$ adenosine receptors (ARs). These compounds and compositions are useful as pharmaceutical agents.

BACKGROUND OF THE INVENTION

The alkylxanthine theophylline (compound 1, FIG. 1), a weak non-selective adenosine antagonist (See Linden, J., et al., in *Cardiovascular Biology of Purines*, eds. G. Burnstock, et al., 1998, pp 1–20.) is useful therapeutically for the treatment of asthma. However, its use is associated with unpleasant side effects, such as insomnia and diuresis. (See Vassallo, R. et al., *Mayo. Clin. Proc.* 1998, 73, 346–354.) In recent years, the use of theophylline as a bronchodilator, for relief of asthma, has been supplanted by drugs of other classes, i.e., selective $\beta_2$-adrenergic agonists, corticosteroids, and recently leukotriene antagonists. (See Drazen, J. M., et al., *New Eng. J. Med.* 1999, 340, 197–206.) These compounds also have limitations, thus, the development of a theophylline-like drug with reduced side effects is still desirable.

It has been recognized that theophylline and its closely related analogue caffeine block endogenous adenosine acting as a local modulator of adenosine receptors in the brain and other organs at therapeutically useful doses. Adenosine activates four subtypes of G protein-coupled adenosine receptors (ARs), $A_1/A_{2A}/A_{2B}/A_3$. (See Fredholm, B. B., et al., *Pharmacol. Rev.* 1999, 51, 83–133.) In comparison to the other known actions of theophylline, e.g., inhibition of phosphodiesterases, theophylline is more potent in antagonism of adenosine receptors. Enprofylline, (compound 3, FIG. 1) a compound that is used to treat asthma, is another example of a xanthine that has been reported to block $A_{2B}$ adenosine receptors. However, this compound only weakly blocks $A_1$, $A_{2A}$ and $A_3$ adenosine receptors.

It has been reported that therapeutic concentrations of theophylline or enprofylline block human $A_{2B}$ receptors, and it has been proposed that antagonists selective for this subtype may have potential use as antiasthmatic agents. (See Feoktistov, I., et al., *Pharmacol. Rev.* 1997, 49, 381–402; and Robeva, A. S., et al., *Drug Dev. Res.* 1996, 39, 243–252. Enprofylline has a reported $K_i$ value of 7 μM and is somewhat selective in binding to human $A_{2B}$ ARs. (See Robeva, A. S., et al., *Drug Dev. Res.* 1996, 39, 243–252 and Linden, J., et al., *Mol. Pharmacol.* 1999, 56, 705–713.) $A_{2B}$ ARs are expressed in some mast cells, such as the BR line of canine mastocytoma cells, which appear to be responsible for triggering acute $Ca^{2+}$ mobilization and degranulation. (See Auchampach, J. A., et al., *Mol. Pharmacol.* 1997. 52, 846–860 and Forsyth, P., et al., *Inflamm. Res.* 1999, 48, 301–307.) $A_{2B}$ ARs also trigger $Ca^{2+}$ mobilization, and participate in a delayed IL8 release from human HMC-1 mast cells. Other functions associated with the $A_{2B}$ AR are the control of cell growth and gene expression, (See Neary, J., et al., *Trends Neurosci.* 1996, 19, 13–18.) endothelial-dependent vasodilation (See Martin, P. L., et al., *J. Pharmacol. Exp. Ther.* 1993, 265, 248–253.), and fluid secretion from intestinal epithelia. (See Strohmeier, G. R., et al., *J. Biol. Chem.* 1995, 270, 2387–2394.) Adenosine acting through $A_{2B}$ ARs has also been reported to stimulate chloride permeability in cells expressing the cystic fibrosis transport regulator. (See Clancy, J. P., et al., *Am. J. Physiol.* 1999, 276, C361–C369.)

Although adenosine receptor subtype-selective probes are available for the $A_1$, $A_{2A}$, and $A_3$ ARs, only few weakly selective antagonists and no selective agonists are known for the $A_{2B}$ receptor. Therefore, a continuing need exists for compounds that are selective $A_{2B}$ receptor antagonists.

SUMMARY OF THE INVENTION

The present invention provides compounds that act as antagonists of $A_{2B}$ adenosine receptors. Accordingly, the present invention provides a compound of formula I:

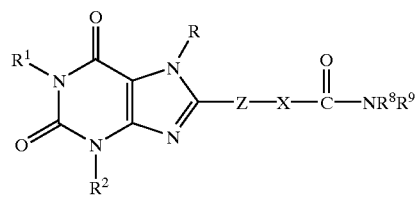

wherein R, and $R^1$ are independently hydrogen, $(C_1-C_8)$ alkyl, $(C_2-C_8)$alkenyl, $(C_2-C_8)$alkynyl, $(C_1-C_8)$alkoxy, $(C_3-C_8)$cycloalkyl, $(C_4-C_{16})$cycloalkylalkyl, hetero-cycle, $(C_6-C_{10})$aryl, $(C_7-C_{18})$aralkyl or heteroaryl;

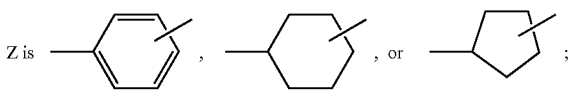

X is $(C_1-C_8)$alkylene, $(C_2-C_8)$alkenylene, $(C_2-C_8)$ alkynylene, wherein one of the carbon atoms in the alkylene, alkenylene or alkynylene groups can be replaced with group having the formula —O—, —N(R$^4$)C(O)—, —OC(O)—, —N(R$^5$)(R$^6$)—, —S—, —S(O)— or —SO$_2$—, wherein $R^2$ is hydrogen, $(C_1-C_8)$alkyl, $(C_2-C_8)$alkenyl, $(C_2-C_8)$ alkynyl, $(C_1-C_8)$alkoxy, $(C_3-C_8)$cycloalkyl, $(C_3-C_8)$ heterocycle, $(C_6-C_{10})$aryl, $(C_6-C_{10})$heteroaryl, $(C_4-C_{16})$cycloalkylalkyl or $(C_7-C_{18})$aralkyl, optionally substituted with one or more substituents selected from the group consisting of —OH, —SH, —NH$_2$, —NHR$^7$, —CN, —CO$_2$H, and —SO$_3$H, wherein $R^4$, $R^5$, $R^6$ and $R^7$ are independently hydrogen, $(C_1-C_8)$ alkyl, $(C_2-C_8)$alkenyl, $(C_3-C_8)$cycloalkyl, $(C_6-C_{10})$ aryl, $(C_7-C_{18})$aralkyl or halo$(C_1-C_6)$alkyl, wherein $R^8$ is hydrogen, $(C_3-C_8)$cycloalkyl, $(C_4-C_{16})$ cycloalkylalkyl, $(C_7-C_{18})$aralkyl, heterocycle or heteroaryl, each optionally substituted with one or more substituents, wherein the substituents independently are oxo, $(C_1-C_8)$alkyl, halo$(C_1-C_6)$alkyl, $(C_2-C_8)$alkenyl, $(C_6-C_{10})$aryl, $(C_7-C_{18})$aralkyl, heteroaryl, halo, —$OR^{15}$, —CN, —$NO_2$, —$CO_2R^{15}$, —$OC(O)R^{16}$, —$C(O)R^{16}$, —$NR^{13}R^{14}$, —$N(R^{23})C(O)R^{24}$, —$C(O)NR^{17}R^{18}$, —$SR^{19}$, —$SO_2R^{20}$ or —$SO_3H$; or $R^8$ is $(C_1-C_8)$alkyl, substituted with one or more substituents independently selected from the group consisting of oxo, $(C_2-C_8)$alkenyl, $(C_6-C_{10})$aryl, $(C_7-C_{18})$aralkyl, heteroaryl, halo —$OR^{15}$, —CN, —$NO_2$, —$CO_2R^{15}$, —$OC(O)R^{16}$, —$C(O)R^{16}$, —$NR^{13}R^{14}$, —$N(R^{23})C(O)R^{24}$, —$C(O)NR^{17}R^{18}$, —$SR^{19}$, —$SO_2R^{20}$ and —$SO_3H$; or $R^8$ is $(C_6-C_{10})$aryl, substituted with one or more substituents independently selected from the group consisting of $(C_1-C_8)$alkyl, halo$(C_1-C_6)$alkyl, $(C_2-C_8)$alkenyl, $(C_7-C_{18})$aralkyl, heteroaryl, —$OR^{15}$, —CN, —$NO_2$, —$CO_2R^{15}$, —$OC(O)R^{16}$, —$C(O)R^{16}$, —$NR^{13}R^{14}$, —$N(R^{23})C(O)R^{24}$, —$C(O)NR^{17}R^{18}$, —$SR^{19}$, —$SO_2R^{20}$ and —$SO_3H$; and wherein $R^9$ is —$NR^{10}R^{11}$, or $R^9$ is $(C_3-C_8)$cycloalkyl, $(C_4-C_{16})$cycloalkylalkyl, $(C_7-C_{18})$aralkyl, heterocycle or heteroaryl, each optionally substituted with one or more substituents, wherein the substituents independently are oxo, $(C_1-C_8)$alkyl, halo$(C_1-C_6)$alkyl, $(C_2-C_8)$alkenyl, $(C_6-C_{10})$aryl, $(C_7-C_{18})$aralkyl, heteroaryl, —$OR^{15}$, halo, —CN, —$NO_2$, —$CO_2R^{15}$, —$OC(O)R^{16}$, —$C(O)R^{16}$, —$NR^{13}R^{14}$, —$N(R^{23})C(O)R^{24}$, —$C(O)NR^{17}R^{18}$, —$SR^{19}$, —$SO_2R^{20}$ or —$SO_3H$; or $R^9$ is $(C_{1-8})$alkyl, substituted with one or more substituents independently selected from the group consisting of oxo, $(C_2-C_8)$alkenyl, $(C_6-C_{10})$aryl, $(C_7-C_{18})$aralkyl, heteroaryl, —$OR^{15}$, halo, —CN, —$NO_2$, —$OC(O)R^{16}$, —$C(O)R^{16}$, —$NR^{13}R^{14}$, —$N(R^{23})C(O)R^{24}$, —$C(O)NR^{17}R^{18}$, —$SR^{19}$, —$SO_2R^{20}$ and —$SO_3H$;

$R^9$ is $(C_6-C_{10})$aryl, substituted with one or more substituents independently selected from the group consisting of $(C_1-C_8)$alkyl, halo$(C_1-C_6)$alkyl, $(C_2-C_8)$alkenyl, $(C_7-C_{18})$aralkyl, heteroaryl, —$OR^{15}$, —CN, —$NO_2$, —$CO_2R^{15}$, —$OC(O)R^{16}$, —$C(O)R^{16}$, —$NR^{13}R^{14}$, —$N(R^{23})C(O)R^{24}$, —$C(O)NR^{17}R^{18}$, —$SR^{19}$, —$SO_2R^{20}$ and —$SO_3H$, and wherein $R^{10}$ and $R^{11}$ are independently hydrogen, $(C_1-C_8)$alkyl, $(C_2-C_8)$alkenyl, $(C_3-C_8)$cycloalkyl, $(C_6-C_{10})$aryl, $(C_7-C_{18})$aralkyl, heterocycle, heteroaryl, —$C(O)(CH_2)_nCO_2R^{12}$, —$C(O)CR^{21}$=$CR^{22}(CH_2)_m$ $CO_2R^{12}$, —$C(O)R^{12}$, —$C(O)(C_3-C_8)$cycloalkyl or —$C(O)(C_3-C_8)$cycloalkenyl, each optionally substituted with one or more substituents, wherein the substituents independently are oxo, $(C_1-C_8)$alkyl, halo$(C_1-C_6)$alkyl, $(C_2-C_8)$alkenyl, $(C_6-C_{10})$aryl, $(C_7-C_{18})$aralkyl, heteroaryl, —$OR^{15}$, halo, —CN, —$NO_2$, —$CO_2R^{15}$, —$OC(O)R^{16}$, —$C(O)R^{16}$, —$NR^{13}R^{14}$, —$N(R^{23})C(O)R^{24}$, —$C(O)NR^{17}R^{18}$, —$SR^{19}$, —$SO_2R^{20}$ or —$SO_3H$; or the $R^{10}$ and $R^{11}$ groups and the nitrogen atom can be taken together to form a heterocyclic ring or a heteroaryl ring, each ring optionally substituted with one or more substituents, wherein the substituents independently are oxo, $(C_1-C_8)$alkyl, halo$(C_1-C_6)$alkyl, $(C_2-C_8)$alkenyl, $(C_6-C_{10})$aryl, $(C_7-C_{18})$aralkyl, heteroaryl, —$OR^{15}$, halo, —CN, —$NO_2$, $CO_2R^{15}$, —$OC(O)R^{16}$, —$C(O)R^{16}$, —$NR^{13}R^{14}$, —$N(R^{23})C(O)R^{24}$, —$C(O)NR^{17}R^{18}$, —$SR^{19}$, —$SO_2R^{20}$ or —$SO_3H$; wherein n is 1 to 6, and m is 0 to 4;

$R^{12}$ is hydrogen, $(C_1-C_8)$alkyl, $(C_2-C_8)$alkenyl, $(C_2-C_8)$alkynyl, $(C_3-C_8)$cycloalkyl, $(C_4-C_{16})$cycloalkylalkyl, $(C_6-C_{10})$aryl, $(C_7-C_{18})$aralkyl, hetero-cycle, or heteroaryl, wherein the $R^{12}$ group is optionally substituted with one or more substituents independently selected from the group consisting of oxo, $(C_1-C_8)$alkyl, halo$(C_1-C_6)$-alkyl, $(C_2-C_8)$alkenyl, $(C_6-C_{10})$aryl, $(C_7-C_{18})$aralkyl, heteroaryl, —$OR^{15}$, halo, —CN, —$NO_2$, —$CO_2R^{15}$, $OC(O)R^{16}$, —$C(O)R^{16}$, —$NR^{13}R^{14}$, —$N(R^{23})C(O)R^{24}$, —$C(O)NR^{17}R^{18}$, —$SR^{19}$, —$SO_2R^{20}$ or —$SO_3H$.

The $R^{13}$, $R^{14}$, $R^{15}$, $R^{16}$, $R^{17}$, $R^{18}$, $R^{19}$, $R^{20}$, $R^{23}$ and $R^{24}$ groups are independently hydrogen, $(C_1-C_8)$alkyl, $(C_2-C_8)$alkenyl, $(C_3-C_8)$cycloalkyl, $(C_6-C_{10})$aryl, $(C_7-C_{18})$aralkyl or halo$(C_1-C_6)$alkyl; and the $R^{21}$ and $R^{22}$ groups are independently hydrogen, $(C_1-C_8)$alkyl, $(C_2-C_8)$alkenyl, $(C_3-C_8)$cycloalkyl, $(C_6-C_{10})$aryl, $(C_7-C_{18})$aralkyl.

The invention also provides pharmaceutically acceptable salts of a compound of formula I. The invention also provides a pharmaceutical composition comprising a compound of formula I or a pharmaceutically acceptable salt thereof, in combination with a pharmaceutically acceptable diluent or carrier.

Additionally, the invention provides a therapeutic method for preventing or treating a pathological condition or symptom in a mammal, such as a human, wherein the activity, i.e., over-activity, of adenosine $A_{2B}$ receptors is implicated in one or more symptoms of the pathology and antagonism (i.e., blocking) of their activity is desired to ameliorate said symptoms. Such diseases or conditions include, but are not limited to, asthma, diarrheal diseases, insulin resistance, diabetes, prevention of mast cell degranulation associated with ischemia/reperfusion injuries, inhibition of angiogenesis in neoplastic tissues, and inhibition of angiogenesis in diabetic retinopathy or hyperbaric oxygen-induced retinopathy. The invention also includes a method for treating asthma, diarrheal diseases, insulin resistance, diabetes, inhibition of angiogenesis in neoplastic tissues, and inhibition of angiogenesis in diabetic retinopathy or hyperbaric oxygen-induced retinopathy in a mammal, (e.g., a human) comprising administering to the mammal in need of such therapy, an effective amount of at least one compound of formula I or pharmaceutically acceptable salt(s) thereof.

The invention provides a compound of formula I for use in medical therapy preferably for use in treating diseases or conditions associated with deleterious $A_{2B}$ receptor activation or activity, including asthma, diarrheal diseases, insulin resistance, diabetes, ischemic/reperfusion injury, inhibition of angiogenesis in neoplastic tissues, and inhibition of angiogenesis in diabetic retinopathy or hyperbaric oxygen-induced retinopathy, as well as the use of a compound of formula I for the manufacture of a medicament for the treatment of a pathological condition or symptom in a mammal, such as a human, which is associated with deleterious $A_{2B}$ receptor activation or activity, including the above-referenced diseases or pathologies.

The invention also includes a method comprising contacting a compound of formula I, optionally having a radioactive isotope (radionuclide), such as, for example, tritium, radioactive iodine (for example, $^{125}I$ for binding assays or $^{123}I$ for Spect Imaging) and the like, with target $A_{2B}$ adenosine receptor sites comprising said receptors, in vivo or in vitro, so as to bind said receptors. Cell membranes comprising bound $A_{2B}$ adenosine receptor sites can be used to measure the selectivity of test compounds for adenosine receptor subtypes or can be used as a tool to identify potential therapeutic agents for the treatment of diseases or conditions associated with $A_{2B}$-receptor mediation, by contacting said agents with said radioligands and receptors, and measuring the extent of displacement of the radioligand and/or binding of the agent.

DETAILED DESCRIPTION OF THE INVENTION

Figure 1A:
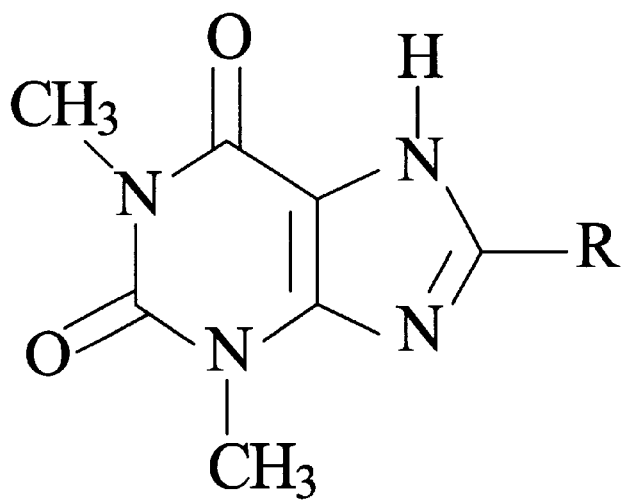
FIG. 1 illustrates structures of various xanthines that act as antagonists at $A_{2B}$ receptors.
Figure 1B:
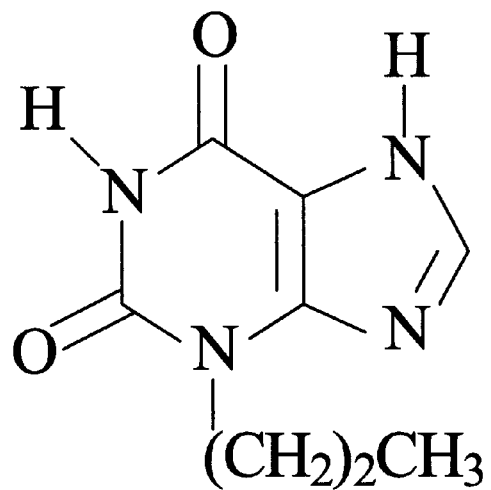
Figure 1C:
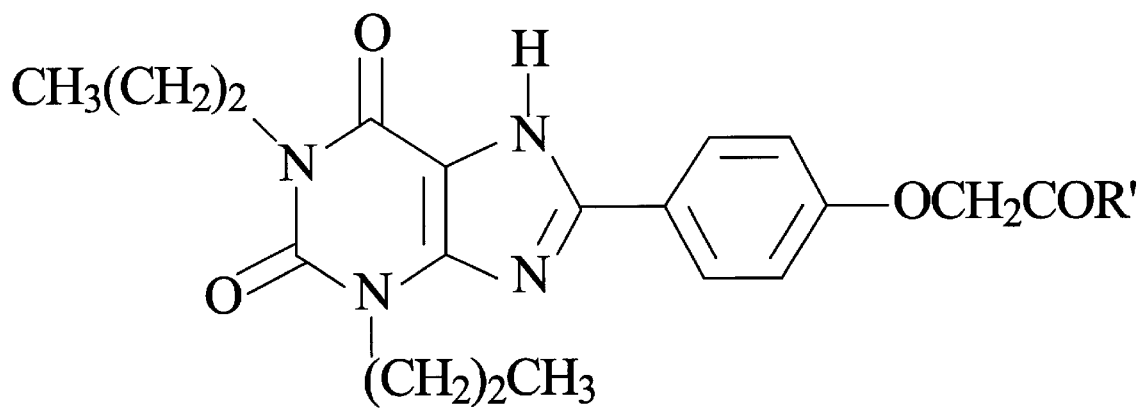
Figure 1C:
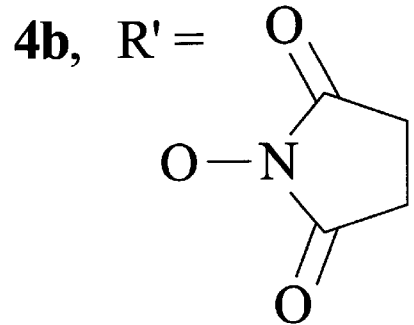
Figure 1C:
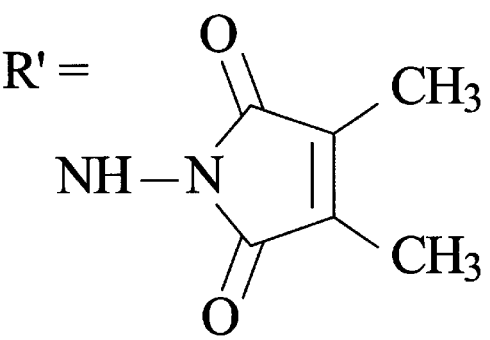

In one embodiment the present invention provides compounds of formula I:

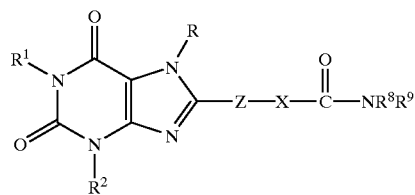

wherein R, and $R^1$ are independently hydrogen, $(C_1-C_8)$ alkyl, $(C_2-C_8)$alkenyl, $C_2-C_8)$alkynyl, $(C_1-C_8)$alkoxy, $(C_3-C_8)$cycloalkyl, $(C_4-C_{16})$cycloalkylalkyl, $C_3-C_8)$ heterocycle, $(C_6-C_{10})$aryl, $(C_7-C_{18})$aralkyl or $(C_6-C_{10})$ heteroaryl, Z is 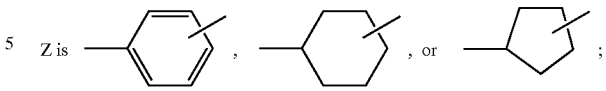

and X is $(C_1-C_8)$alkylene, $(C_2-C_8)$alkenylene, $(C_2-C_8)$ alkynylene. In the X groups one of the carbon atoms in the alkylene, alkenylene or alkynylene groups can be replaced with a group having the formula —O—, —N(R$^4$)C(O)—, —OC(O)—, —N(R$^5$)(R$^6$, —S—, —S(O)— or —SO$_2$—, wherein $R^2$ is hydrogen, $(C_1-C_8)$alkyl, $(C_2-C_8)$alkenyl, $(C_2-C_8)$ alkynyl, $(C_1-C_8)$alkoxy, $(C_3-C_8)$cycloalkyl, $(C_3-C_8)$ heterocycle, $(C_6-C_{10})$aryl, $(C_6-C_{10})$heteroaryl, $(C_4-C_{16})$cycloalkylalkyl or $(C_7-C_{18})$aralkyl; optionally substituted with one or more substituents selected from the group consisting of —OH, —SH, —NH$_2$, —NHR$^7$, —CN, —CO$_2$H, and —SO$_3$H, wherein $R^4, R^5, R^6$ and $R^7$ are independently hydrogen, $(C_1-C_8)$ alkyl, $(C_2-C_8)$alkenyl, $(C_3-C_8)$cycloalkyl, $(C_6-C_{10})$ aryl, $(C_7-C_{18})$aralkyl or halo$(C_1-C_6)$alkyl.

$R^8$ is hydrogen, $(C_3-C_8)$cycloalkyl, $(C_4-C_{16})$ cycloalkylalkyl, $(C_7-C_{18})$aralkyl, heterocycle or heteroaryl, each optionally substituted with one or more substituents, wherein the substituents independently are oxo, $(C_1-C_8)$alkyl, $(C_1-C_8)$alkoxy, halo $(C_1-C_6)$alkyl, $(C_2-C_8)$alkenyl, $(C_6-C_{10})$aryl, $(C_7-C_{18})$ aralkyl, heteroaryl, halo, —OR$^{15}$, —CN, —NO$_2$, —CO$_2$R$^{15}$, —OC(O)R$^{16}$, —C(O)R$^{16}$, —NR$^{13}$R$^{14}$, —N(R$^{23}$)C(O)R$^{24}$, —C(O)NR$^{17}$R$^{18}$, —SR$^{19}$, —SO$_2$R$^{20}$ or —SO$_3$H; or $R^8$ is $(C_1-C_8)$alkyl, substituted with one or more substituents independently selected from the group consisting of oxo, $(C_2-C_8)$alkenyl, $(C_6-C_{10})$aryl, $(C_7-C_{18})$ aralkyl, heteroaryl, —OR$^{15}$, halo, —CN, —NO$_2$, —OC(O)R$^{16}$, —C(O)R$^{16}$, —NR$^{13}$R$^{14}$, N(R$^{23}$)C(O) R$^{24}$, —C(O)NR$^{17}$R$^{18}$, —SR$^{19}$, —SO$_2$R$^{20}$ and —SO$_3$H; or $R^8$ is $(C_6-C_{10})$aryl, substituted with one or more substituents independently selected from the group consisting of $(C_1-C_8)$alkyl, halo$(C_1-C_6)$alkyl, $(C_2-C_8)$alkenyl, $(C_7-C_{18})$aralkyl, heteroaryl, —OR$^{15}$, —CN, —NO$_2$, —CO$_2$R$^{15}$, —OC(O)R$^{16}$, —C(O)R$^{16}$, —NR$^{13}$R$^{14}$, —N(R$^{23}$)C(O)R$^{24}$, —C(O)NR$^{17}$R$^{18}$, —SR$^{19}$, SO$_2$R$^{20}$ and —SO$_3$H; and wherein $R^9$ is $(C_3-C_8)$cycloalkyl, $(C_4-C_{16})$ cycloalkylalkyl, $(C_7-C_{18})$aralkyl, heterocycle or heteroaryl, each optionally substituted with one or more substituents, wherein the substituents independently are oxo, $(C_1-C_8)$alkyl, halo$(C_1-C_6)$alkyl, $(C_2-C_8)$alkenyl, $(C_6-C_{10})$aryl, $(C_7-C_{18})$aralkyl, heteroaryl, —OR$^{15}$, halo, —CN, —NO$_2$, —CO$_2$R$^{15}$, —OC(O)R$^{16}$, —C(O)R$^{16}$, —NR$^{13}$R$^{14}$, —N(R$^{23}$)C(O) R$^{24}$, —C(O)NR$^{17}$R$^{18}$, —SR$^{19}$, —SO$_2$R$^{20}$ or —SO$_3$H; or $R^9$ is $(C_1-C_8)$alkyl, substituted with one or more substituents independently selected from the group consisting of oxo, $(C_2-C_8)$alkenyl, $(C_6-C_{10})$aryl, $(C_7-C_{18})$ aralkyl, heteroaryl, —OR$^{15}$, halo, —CN, —NO$_2$, —OC(O)R$^{16}$, —C(O)R$^{16}$, —NR$^{13}$R$^{14}$, —N(R$^{23}$)C(O) R$^{24}$, —C(O)NR$^{17}$R$^{18}$, —SR$^{19}$, —SO$_2$R$^{20}$ and —SO$_3$H; or $R^9$ is $(C_6-C_{10})$aryl, substituted with one or more substituents independently selected from the group consisting of $(C_1-C_8)$alkyl, halo$(C_1-C_6)$alkyl, $(C_2-C_8)$alkenyl, $(C_7-C_{18})$aralkyl, heteroaryl, —OR$^{15}$, —CN, —NO$_2$, —CO$_2$R$^{15}$, —OC(O)R$^{16}$, —C(O)R$^{16}$, —NR$^{13}$R$^{14}$, —N(R$^{23}$)C(O)R$^{24}$, —C(O)NR$^{17}$R$^{18}$, —SR$^{19}$, —SO$_2$R$^{20}$ and —SO$_3$H.

The R$^{13}$, R$^{14}$, R$^{15}$, R$^{16}$, R$^{17}$, R$^{18}$, R$^{19}$, R$^{20}$, R$^{23}$ and R$^{24}$ groups are independently hydrogen, $(C_1-C_8)$alkyl, $(C_2-C_8)$alkenyl, $(C_3-C_8)$cycloalkyl, $(C_6-C_{10})$aryl, $(C_7-C_{18})$aralkyl or halo$(C_1-C_6)$alkyl.

In another embodiment the present invention provides compounds of formula II:

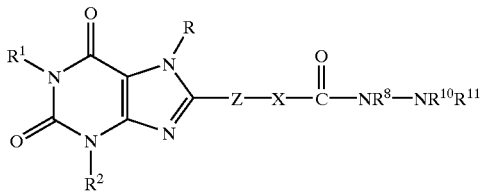

wherein R, and R$^1$ are independently hydrogen, $(C_1-C_8)$alkyl, $(C_2-C_8)$alkenyl, $(C_2-C_8)$alkynyl, $(C_1-C_8)$alkoxy, $(C_3-C_8)$cycloalkyl, $(C_4-C_6)$cycloalkylalkyl, $(C_3-C_8)$heterocycle, $(C_6-C_{10})$aryl, $(C_7-C_{18})$aralkyl or $(C_6-C_{10})$heteroaryl, Z is 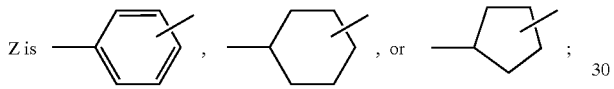

and X is $(C_{1-8})$alkylene, $(C_2-C_8)$alkenylene, $(C_2-C_8)$alkynylene. In the X groups one of the carbon atoms in the alkylene, alkenylene or alkynylene groups can be replaced with a group having the formula —O—, —N(R$^4$)C(O)—, —OC(O)—, —N(R$^5$)(R$^6$)—, —S—, —S(O)— or —SO$_2$—, wherein R$^2$ group is hydrogen, $(C_1-C_8)$alkyl, $(C_2-C_8)$alkenyl, $(C_2-C_8)$alkynyl, $(C_1-C_8)$alkoxy, $(C_3-C_8)$cycloalkyl, $(C_3-C_8)$heterocycle, $(C_6-C_{10})$aryl, $(C_6-C_{10})$heteroaryl, $(C_4-C_{16})$cycloalkylalkyl or $(C_7-C_{18})$aralkyl; optionally substituted with one or more substituents selected from the group consisting of —OH, —SH, —NH$_2$, —NHR$^7$, —CN, —CO$_2$H, and —SO$_3$H, wherein R$^4$, R$^5$, R$^6$ and R$^7$ are independently hydrogen, $(C_1-C_8)$alkyl, $(C_2-C_8)$alkenyl, $(C_3-C_8)$cycloalkyl, $(C_6-C_{10})$aryl, $(C_7-C_{18})$aralkyl or halo$(C_1-C_6)$alkyl.

R$^8$ is hydrogen, $(C_3-C_8)$cycloalkyl, $(C_4-C_{16})$cycloalkylalkyl, $(C_7-C_{18})$aralkyl, heterocycle or heteroaryl, each optionally substituted with one or more substituents, wherein the substituents independently are oxo, $(C_{1-8})$alkyl, $(C_{1-8})$alkoxy, halo$(C_1-C_6)$alkyl, $(C_2-C_8)$alkenyl, $(C_6-C_{10})$aryl, $(C_7-C_{18})$aralkyl, heteroaryl, halo, —OR$^{15}$, —CN, —NO$_2$, —CO$_2$R$^{15}$, —OC(O)R$^{16}$, —C(O)R$^{16}$, NR$^{13}$R$^{14}$, —N(R$^{23}$)C(O)R$^{24}$, —C(O)NR$^{17}$R$^{18}$, —SR$^{19}$, —SO$_2$R$^{20}$ or —SO$_3$H; or R$^8$ is $(C_1-C_8)$alkyl, substituted with one or more substituents independently selected from the group consisting of oxo, $(C_2-C_8)$alkenyl, $(C_6-C_{10})$aryl, $(C_7-C_{18})$aralkyl, heteroaryl, —OR$^{15}$, halo, —N, —NO$_2$, —OC(O)R$^{16}$, —C(O)R$^{16}$, —NR$^{13}$R$^{14}$, —N(R$^{23}$)C(O)R$^{24}$, —C(O)NR$^{17}$R$^{18}$, —SR$^{19}$, —SO$_2$R$^{20}$ and —SO$_3$H; or R$^8$ is $(C_6-C_{10})$aryl, substituted with one or more substituents independently selected from the group consisting of $(C_{1-8})$alkyl, halo$(C_1-C_6)$alkyl, $(C_2-C_8)$alkenyl, $(C_7-C_{18})$aralkyl, heteroaryl, —OR$^{15}$, —CN, —NO$_2$, —CO$_2$R$^{15}$, —OC(O)R$^{16}$, —C(O)R$^{16}$, —NR$^{13}$R$^{14}$, —N(R$^{23}$)C(O)R$^{24}$, —C(O)NR$^{17}$R$^{18}$, —SR$^{19}$, —SO$_2$R$^{20}$ and —SO$_3$H; and wherein R$^{10}$ and R$^{11}$ are independently hydrogen, $(C_1-C_8)$alkyl, $(C_2-C_8)$alkenyl, $(C_3-C_8)$cycloalkyl, $(C_6-C_{10})$aryl, $(C_7-C_{18})$aralkyl, heteroaryl, —C(O)(CH$_2$)$_n$CO$_2$R$^{12}$, —C(O)CR$^{21}$=CR$^{22}$(CH$_2$)$_m$CO$_2$R$^{12}$, —C(O)R$^{12}$, —C(O)(C$_3$-C$_8$)cycloalkyl or —C(O)(C$_3$-C$_8$)cycloalkenyl, each optionally substituted with one or more substituents, wherein the substituents independently are oxo, $(C_1-C_8)$alkyl, halo$(C_1-C_6)$alkyl, $(C_2-C_8)$alkenyl, $(C_6-C_{10})$aryl, $(C_7-C_{18})$aralkyl, heteroaryl, —OR$^{15}$, halo, —N, —NO$_2$, —CO$_2$R$^{15}$, —OC(O)R$^{16}$, —C(O)R$^{16}$, —NR$^{13}$R$^{14}$, —N(R$^{23}$)C(O)R$^{24}$, —C(O)NR$^{17}$R$^{18}$, —SR$^{19}$, —SO$_2$R$^{20}$ or —SO$_3$H; or the R$^{10}$ and R$^{11}$ groups and the nitrogen atom can be taken together to form a heterocyclic ring or a heteroaryl ring, each ring optionally substituted with one or more substituents, wherein the substituents independently are oxo, $(C_1-C_8)$alkyl, halo$(C_{1-6})$alkyl, $(C_2-C_8)$alkenyl, $(C_6-C_{10})$aryl, $(C_7-C_{18})$aralkyl, heteroaryl, —OR$^{15}$, halo, —CN, —NO$_2$, CO$_2$R$^{15}$, —OC(O)R$^{16}$, —C(O)R$^{16}$, —NR$^{13}$R$^{14}$, —N(R$^{23}$)C(O)R$^{24}$, —C(O)NR$^{17}$R$^{18}$, —SR$^{19}$, —SO$_2$R$^{20}$ or —SO$_3$H; wherein n is 1 to 6, and m is 0 to 4;

R$^{12}$ is hydrogen, $(C_1-C_8)$alkyl, $(C_2-C_8)$alkenyl, $(C_2-C_8)$alkynyl, $(C_3-C_8)$cycloalkyl, $(C_4-C_{16})$cycloalkylalkyl, $(C_6-C_{10})$aryl, $(C_7-C_{18})$aralkyl, hetero-cycle, or heteroaryl, wherein the R$^{12}$ group is optionally substituted with one or more substituents independently selected from the group consisting of oxo, $(C_1-C_8)$alkyl, halo$(C_{1-6})$-alkyl, $(C_2-C_8)$alkenyl, $(C_6-C_{10})$aryl, $(C_7-C_{18})$aralkyl, heteroaryl, —OR$^{15}$, halo, —CN, —NO$_2$, —CO$_2$R$^{15}$, —OC(O)R$^{16}$, —C(O)R$^{16}$, —NR$^{13}$R$^{14}$, —N(R$^{23}$)C(O)R$^{24}$, —C(O)NR$^{17}$R$^{18}$, —SR$^{19}$, —SO$_2$R$^{20}$ or —SO$_3$H.

The R$^{13}$, R$^{14}$, R$^{15}$, R$^{16}$, R$^{17}$, R$^{18}$, R$^{18}$, R$^{19}$, R$^{20}$, R$^{23}$ and R$^{24}$ are independently hydrogen, $(C_1-C_8)$alkyl, $(C_2-C_8)$alkenyl, $(C_3-C_8)$cycloalkyl, $(C_6-C_{10})$aryl, $(C_7-C_{18})$aralkyl or halo$(C_1-C_6)$alkyl; and the R$^{21}$ and R$^{22}$ are independently hydrogen, $(C_1-C_8)$alkyl, $(C_2-C_8)$alkenyl, $(C_3-C_8)$cycloalkyl, $(C_6-C_{10})$aryl, $(C_7-C_{18})$aralkyl.

Preferred compounds of the invention exclude compounds of formula I wherein —NR$^8$R$^9$ is aminoalkyl, aminodialkyl or hydrazino. Preferred compounds of the invention also exclude and compounds of formula I wherein R and R$^8$ are both H, and R$^1$ and R$^2$ are both alkyl, and R$^9$ is 2-hydroxyethyl, 2-thiolethyl, 2-haloethyl, 2,2-dimethoxyethyl, 2-acetoxyethyl, 1-methyl-2-phenylethyl, 4-methylphenyl or 4-hydroxyphenyl.

Specific and preferred values listed below for radicals, substituents, and ranges, are for illustration only; they do not exclude other defined values or other values within defined ranges for the radicals and substituents.

The following definitions are used, unless otherwise described: halo is fluoro, chloro, bromo or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic.

Heteroaryl encompasses a radical attached via a ring carbon of a monocyclic aromatic ring containing 5–10 ring atoms, and preferably from 5–6 ring atoms, consisting of carbon and one to four heteroatoms each selected from the group consisting of non-peroxide oxygen, sulfur, and N(Y) wherein Y is absent or is H, O, $(C_1-_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene or tetramethylene diradical thereto.

The term heterocycle encompasses a cyclic radical attached via a ring carbon or nitrogen of a monocyclic or bicyclic ring containing 3–10 ring atoms, and preferably from 5–6 ring atoms, consisting of carbon and one to four heteroatoms each selected from the group consisting of non-peroxide oxygen, sulfur, and N(Y) wherein Y is absent or is H, O, $(C_1-_4)$alkyl, phenyl or benzyl, and optionally containing 1–3 double bonds (e.g. —CH=CH— or —CH=N—). Heterocycle includes, for example, tetrahydrofuryl, dihydrofuryl, tetrahydroimidazolyl, azanorbomyl, pyrrolidinyl, piperidinyl, piperizinyl, and the like.

Specifically, $(C_1-C_8)$alkyl can be methyl, ethyl, propyl, isopropyl, butyl, iso-butyl, sec-butyl, pentyl, isopentyl, 3-pentyl, hexyl, heptyl or octyl; $(C_3-C_8)$cycloalkyl can be cyclopropyl, cyclobutyl, cyclopentyl, cyclohexyl, cycloheptyl or cyclooctyl; $(C_4-C_{12})$cycloalkylalkyl can be cyclopropylmethyl, cyclobutylmethyl, cyclopentylmethyl, cyclohexylmethyl, 2-cyclopropylethyl, 2-cyclobutylethyl, 2-cyclopentylethyl or 2-cyclohexylethyl; $(C_1-C_8)$alkoxy can be methoxy, ethoxy, propoxy, isopropoxy, butoxy, iso-butoxy, sec-butoxy, pentoxy, 3-pentoxy, hexyloxy, heptyloxy or octyloxy; $(C_2-C_8)$alkenyl can be vinyl, allyl, 1-propenyl, 2-propenyl, 1-butenyl, 2-butenyl, 3-butenyl, 1-pentenyl, 2-pentenyl, 3-pentenyl, 1-hexenyl, 2-hexenyl, 3-hexenyl, 1-heptenyl, 2-heptenyl, 3-heptenyl, 1-octenyl, 2-octenyl, 3-octenyl or 4-octenyl; $(C_2-C_8)$alkynyl can be ethynyl, 1-propynyl, 2-propynyl, 1-butynyl, 2-butynyl, 3-butynyl, 1-pentynyl, 2-pentynyl, 3-pentynyl, 1-hexynyl, 2-hexynyl, 3-hexynyl, 1-heptynyl, 2-heptynyl, 3-heptynyl, 1-octynyl, 2-octynyl or 3-octynyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl or pentafluoroethyl; $(C_6-C_{10})$aryl can be phenyl, indenyl or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

The term "amino acid," comprises the residues of the natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g., acetyl, benzyl, COCF$_3$ or benzyloxycarbonyl), as well as natural and unnatural amino acids protected at the carboxy terminus (e.g., as a $(C_1-C_6)$alkyl, phenyl or benzyl ester or amide; or as an a-methylbenzyl amide). Other suitable amino and carboxy protecting groups are known to those skilled in the art (See for example, Greene, T. W.; Wutz, P. G. M. *Protecting Groups In Organic Synthesis*, Second Edition, 1991, New York, John Wiley & sons, Inc, and references cited therein). An amino acid can be linked to the remainder of a compound of formula I through the carboxy terminus, the amino terminus or through any other convenient point of attachment, such as, for example, through the sulfur of cysteine.

The term "peptide" comprises the residues two or more of the natural amino acids, as well as unnatural amino acids or a mixture thereof, that are linked through an amide bond. The term also comprises peptides that are protected at the carboxy terminus (e.g., as a $(C_1-C_6)$alkyl, phenyl or benzyl ester or amide; or as an α-methylbenzyl amide). Other suitable amino and carboxy protecting groups are known to those skilled in the art (See for example, Greene, T. W.; Wutz, P. G. M. *Protecting Groups In Organic Synthesis*, Second Edition, 1991, New York, John Wiley & sons, Inc, and references cited therein). A peptide can be linked to the remainder of a compound of formula I through the carboxy terminus, the amino terminus or through any other convenient point of attachment, such as, for example, through the sulfur of cysteine. Preferably, the peptide has less than 30 amino acid residues, more preferably less than 20 residues, and most preferably from about 2 to about 5 residues.

The preferred alkyl groups are methyl, ethyl, propyl, isopropyl, butyl, tert-butyl, iso-butyl, and sec-butyl, 1-pentyl, 2-pentyl, 3-pentyl, 1-hexyl, 2-hexyl, and 3-hexyl. The preferred alkylene groups are methylene, ethylene, propylene, butylene, pentylene, and hexylene. The preferred alkenyl groups are vinyl, 1-propenyl, 2-propenyl (allyl), 1-butenyl, 2-butenyl, 3-butenyl, 1-pentenyl, 2-pentenyl, 3-pentenyl, 4-pentenyl, 1-hexenyl, 2-hexenyl, and 3-hexenyl. The preferred alkenylene groups are ethenylene, propenylene, butenylene, pentenylene, and hexenylene. The preferred alkynyl groups are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl. The preferred alkoxy groups are methoxy, ethoxy, propoxy, isopropoxy, butoxy, iso-butoxy, and sec-butoxy. The preferred cycloalkyl groups are cyclopentyl, and cyclohexyl. The preferred cycloalkylalkyl groups are, cyclopentylmethyl, cyclohexylmethyl, 2-cyclopentylethyl, and 2-cyclohexylethyl. The preferred aryl groups are phenyl, indenyl or naphthyl. The preferred aralkyl groups are benzyl and 2-phenylethyl. The preferred haloalkyl groups are iodomethyl, bromomethyl, chloromethyl, fluoromethyl, trifluoromethyl, 2,2,2-trifluoroethyl or pentafluoroethyl. The preferred heteroaryl groups are furyl, imidazolyl, triazolyl, triazinyl, oxazoyl, isoxazoyl, thiazolyl, isothiazoyl, thiodiazolyl, thiophenyl, pyrazolyl, pyrrolyl, pyrazinyl, tetrazolyl, pyridinyl, (or its N-oxide), thienyl, pyrimidinyl (or its N-oxide), indolyl, isoquinolyl (or its N-oxide) or quinolyl (or its N-oxide).

A specific Z substituent is:

A specific Z—X moiety is:

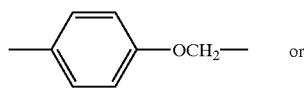

-continued

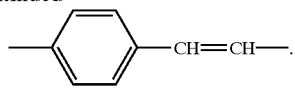

Specific $R^1$ and $R^2$ groups are each —$CH_2CH_3$, —$CH_2CH=CH_2$, $CH_2CH_2CH_3$ or cyclohexylmethyl.

Specific $R^8$ and $R^9$ groups are each hydrogen, substituted phenyl or benzyl.

Specific $R^4$, $R^5$, $R^6$, and $R^7$ groups are each hydrogen, methyl, ethyl, propyl, isopropyl, butyl, vinyl, propenyl, butenyl, cyclopentyl, cyclohexyl, trifluoromethyl, 2,2,2-trifluoroethyl, pentafluoroethyl, phenyl and benzyl.

In a preferred embodiment, when the $R^9$ groups are phenyl substituted with one two or three substituents that are independently cyclopentyl, cyclohexyl, trifluoromethyl, 2,2,2-trifluoroethyl, pentafluoroethyl, phenyl, benzyl, —OH, F, Cl, Br, I, —CN, —$NO_2$, —C(O)$OR^{15}$, —C(O)$R^{16}$, —$NR^{13}R^{14}$ or —C(O)$NR^{17}R^{18}$ or benzyl they can optionally be methyl, ethyl, propyl, isopropyl, butyl, vinyl, propenyl, butenyl, cyclopentyl, cyclohexyl, trifluoromethyl, 2,2,2-trifluoroethyl, pentafluoroethyl, phenyl, benzyl, —OH, F, Cl, Br, I, —CN, —$NO_2$, —C(O)$OR^{15}$, —C(O)$R^{16}$ or —C(O)$NR^{17}R^{18}$, wherein $R^{13}$, $R^{14}$, $R^{15}$, $R^{16}$, $R^{17}$ and $R^{18}$ are as defined above.

The preferred $R^{10}$, and $R^{11}$ groups are hydrogen, methyl, ethyl, propyl, isopropyl, butyl, vinyl, propenyl, butenyl, cyclopentyl, cyclopentenyl, cyclohexyl, cyclohexenyl, trifluoromethyl, 2,2,2-trifluoroethyl, pentafluoroethyl, phenyl and benzyl, —CO$(CH_2)_n CO_2 R^{12}$, —COC$R^{21}$=C$R^{22}$ $(CH_2)_m CO_2 R^{12}$, C(O)$R^{12}$, —C(O)($C_3$-$C_8$)cycloalkyl, —C(O)($C_3$-$C_8$)cycloalkenyl, and compounds wherein the $R^{10}$ and $R^{11}$ groups and the nitrogen atom taken together form a ring. More preferred $R^{10}$, and $R^{11}$ groups are independently hydrogen, —CO$(CH_2)_n CO_2 R^{12}$, —COC$R^{21}$=C$R^{22}(CH_2)_m CO_2 R^{12}$, —C(O)$R^{12}$, —C(O)($C_3$-$C_6$)cycloalkyl and —C(O)($C_3$-$C_6$)cycloalkenyl, each wherein the $R^{10}$ and $R^{11}$ groups and the nitrogen atom taken together form ($C_6$-$C_{10}$)heterocycle or ($C_6$-$C_{10}$)heteroaryl, n is 1 to 4 and m is 0 to 2. The most preferred $R^{10}$, and $R^{11}$ groups are independently hydrogen, —CO($CH_2)_n CO_2 R^{12}$, —COCH=CHCO$_2 R^{12}$, —C(O)$R^{12}$, or wherein the $R^{10}$ and $R^{11}$ groups and the nitrogen atom taken together form a ring or wherein n is 1 to 4 and $R^{12}$, $R^{13}$, $R^{14}$, $R^{21}$ and $R^{22}$ are defined above.

Specific values for —$NR^8R^9$ are:

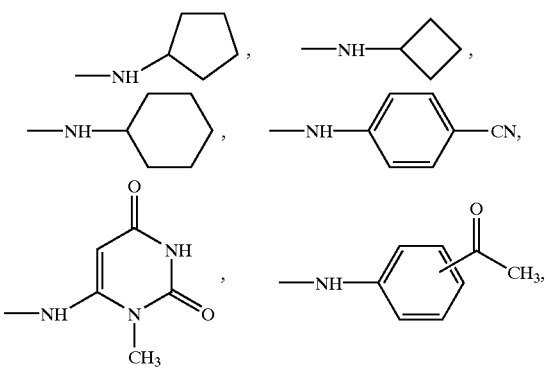

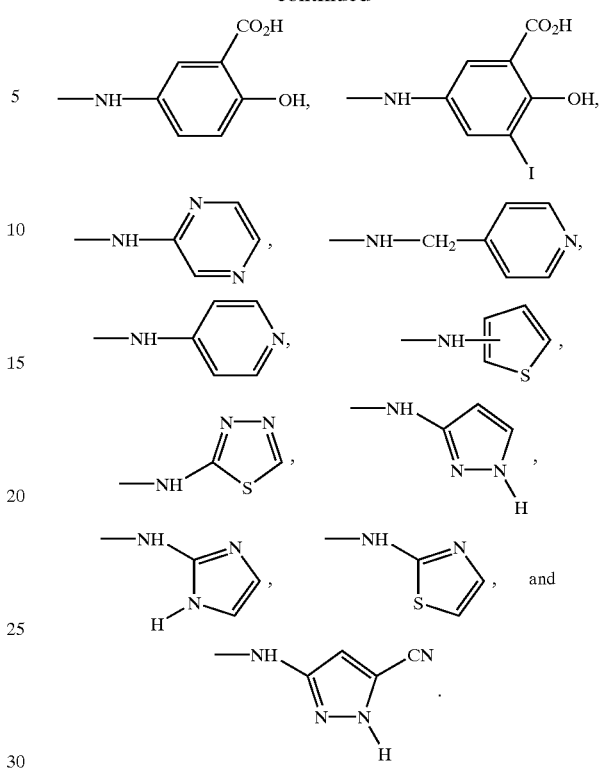

Specific values for —$NR^{10}R^{11}$ are:

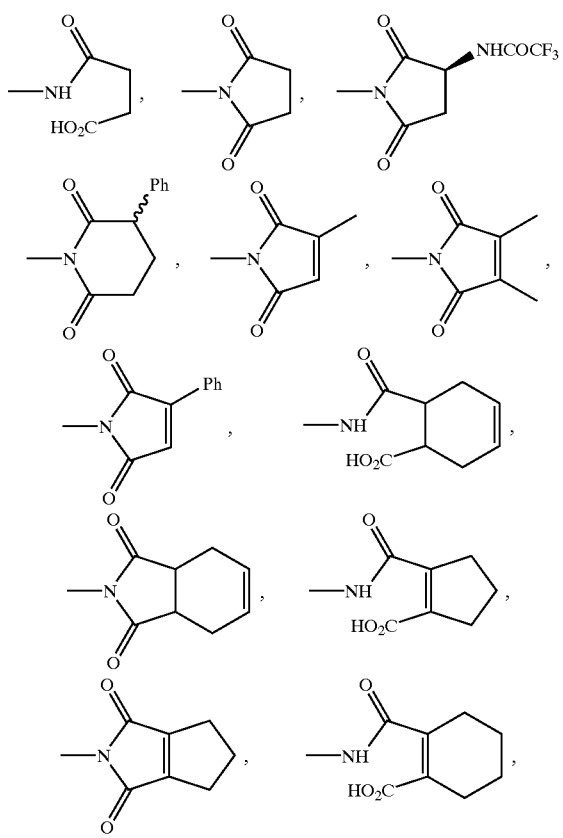

-continued

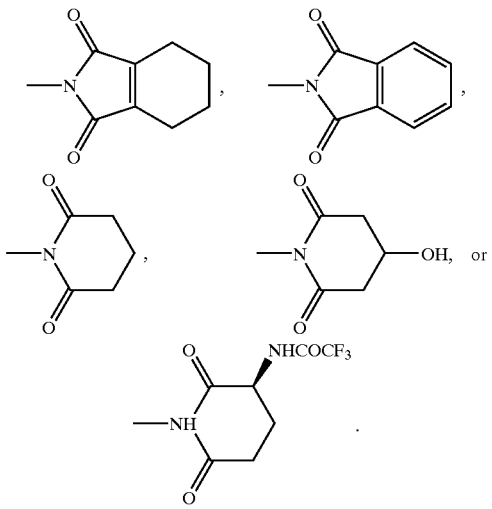

The following abbreviations have been used herein:

| | |
|---|---|
| [$^{125}$I]ABA | [$^{125}$I]N$^6$-(4-aminobenzyl)-adenosine |
| [$^{125}$I]AB-MECA | [$^{125}$I]N$^6$-(4-amino-3-iodobenzyl)-adenosine-5'-N-methyluronamide |
| $^{125}$I-ABOPX | $^{125}$I-3-(4-amino-3-iodobenzyl)-8-oxyacetate-1-propyl-xanthine |
| 8-SPT | 8-sulfophenyltheophylline |
| AR | adenosine receptor |
| Bn | benzyl |
| BOP-Cl | bis(2-oxo-3-oxazolidinyl)-phosphinic chloride |
| CGS 21680 | 2-[4-[(2-carboxyethyl)phenyl]ethyl-amino]-5'-N-ethylcarbamoyl adenosine |
| CHA | N$^6$-cyclohexyladenosine |
| CHO cells | Chinese hamster ovary cells |
| CPX | 8-cyclopentyl-1,3-dipropylxanthine |
| DIPEA | diisopropylethylamine |
| DMAP | 4-dimethylaminopyridine |
| DMEM | Dulbecco modified eagle medium |
| DMF | N,N-dimethylformamide |
| DMSO | dimethylsulfoxide |
| EDAC | 1-ethyl-3-(3-dimethlyaminopropyl)carbodiimide |
| EDTA | ethylenediaminetetraacetate |
| HEK cells | human embryonic kidney cells |
| HOBt | 1-hydroxybenzotriazole |
| K$_i$ | equilibrium inhibition constant |
| NECA | 5I-(N-ethylcarbamoyl)adenosine |
| NHS | N-hydroxysuccinimide ester |
| R-PIA | R-N$^6$-phenylisopropyladenosine |
| SAR | structure-activity relationship |
| TFA | trifluoroacetic acid |
| TFAA | trifluoroacetic anhydride |
| Tris | tris(hydroxymethyl)aminomethane |
| XAC | 8-[4-[[[[(2-aminoethyl)amino]carbonyl]methyl]oxy]phenyl]-1,3-dipropylxanthine |
| XCC | 8-[4-[[[carboxy]methyl]oxy]phenyl]-1,3-dipropylxanthine |
| ZM 241385 | 4-(2-[7-amino-2-{furyl}{1,2,4}triazolo{2,3-a}{1,3,5}triazin-5-ylaminoethyl)phenol |

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic or stereoisomeric form or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis or by chromatographic separation using a chiral stationary phase). It is also conventional to determine A$_{2B}$ adenosine antagonist activity using the standard tests described herein or using other similar tests which are well known in the art.

The compounds of formula I can be formulated as pharmaceutical compositions and administered to a mammalian host, such as a human patient in a variety of forms adapted to the chosen route of administration, i.e., orally or parenterally, by intravenous, intramuscular, topical, inhalation or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any, material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 $\mu$g/kg, e.g., from about 10 to about 75 $\mu$g/kg of body weight per day, such as 3 to about 50 $\mu$g per kilogram body weight of the recipient per day, preferably in the range of 6 to 90 $\mu$g/kg/day, most preferably in the range of 15 to 60 $\mu$g/kg/day.

The compound is conveniently administered in unit dosage form; for example, containing 5 to 1000 $\mu$g, conveniently 10 to 750 $\mu$g, most conveniently, 50 to 500 $\mu$g of active ingredient per unit dosage form.

Ideally, the active ingredient should be administered to achieve peak plasma concentrations of the active compound of from about 0.02, to about 5 $\mu$M, preferably, about 0.05 to 2 $\mu$M, most preferably, about 0.1 to about 1 $\mu$M. This may be achieved, for example, by the intravenous injection of a 0.005 to 0.5% solution of the active ingredient, optionally in saline or orally administered as a bolus containing about 1–100 $\mu$g of the active ingredient. Desirable blood levels may be maintained by continuous infusion to provide about 0.01–0.1 $\mu$g/kg/hr or by intermittent infusions containing about 1–10 $\mu$g/kg of the active ingredient(s).

The compounds of the invention can be administered by inhalation from an inhaler, insufflator, atomizer or pressurized pack or other means of delivering an aerosol spray. Pressurized packs may comprise a suitable propellant such as carbon dioxide or other suitable gas. In case of a pressurized aerosol, the dosage unit may be determined by providing a value to deliver a metered amount. The inhalers, insufflators, atomizers are fully described in pharmaceutical reference books such as Remington's Pharmaceutical Sciences Volumes 16 (1980) or 18 (1990) Mack Publishing Co.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting Examples.

EXAMPLES

Pharmacology.

The ability of a compounds of the invention to act as an $A_{2B}$ adenosine receptor antagonists may be determined using pharmacological models which are well known to the art or using test procedures described below.

The human $A_{2B}$ receptor cDNA was subcloned into the expression plasmid pDoubleTrouble as described in Robeva, A. et al., *Biochem. Pharmacol.*, 51, 545–555 (1996). The plasmid was amplified in competent JM109 cells and plasmid DNA isolated using Wizard Megaprep columns (Promega Corporation, Madison, Wis.). $A_{2B}$ adenosine receptors were introduced into HEK-293 cells by means of Lipofectin as described in Felgner, P. L. et al., *Proc. Natl. Acad. Sci. USA*, 84, 7413–7417 (1987).

Cell Culture

Transfected HEK cells were grown under 5% $CO_2$/95% $O_2$ humidified atmosphere at a temperature of 37° C. Colonies were selected by growth of cells in 0.6 mg/mL G418. Transfected cells were maintained in DMEM supplemented with Hams F12 nutrient mixture (1/1), 10% newborn calf serum, 2 mM glutamine and containing 50 IU/mL penicillin, 50 mg/mL streptomycin, and 0.2 mg/mL Geneticin (G418, Boehringer Mannheim). Cells were cultured in 10 cm diameter round plates and subcultured when grown confluent (approximately after 72 hours).

Radioligand Binding Studies.

At $A_{2B}$ receptors: COnfluent monolayers of HEK-$A_{2B}$ cells were washed with PBS followed by ice cold Buffer A (10 mM HEPES, 10 mM EDTA, pH 7.4) with protease inhibitors (10 µg/mL benzamidine, 100 µM phenyhnethane-sulfonyl fluoride, and 2 µg/mL of each aprotinin, pepstatin and leupeptin). The cells were homogenized in a Polytron (Brinkmann) for 20 s, centrifuged at 30,000×g, and the pellets washed twice with buffer HE (10 mM HEPES, 1 mM EDTA, pH 7.4 with protease inhibitors). The final pellet was resuspended in buffer HE, supplemented with 10% sucrose and frozen in aliquots at –80° C. For binding assays membranes were thawed and diluted 5–10 fold with HE to a final protein concentration of approximately 1 mg/mL. To determine protein concentrations, membranes, and bovine serum albumin standards were dissolved in 0.2% NaOH/0.01% SDS and protein determined using fluorescamine fluorescence. Stowell, C. P. et al., *Anal. Biochem.*, 572–580 (1978).

Saturation binding assays for human $A_{2B}$ adenosine receptors were performed with [$^3$H]ZM214,385 (17 Ci/mmol, Tocris Cookson, Bristol UK) (Ji, X. et al., *Drug Design Discov.*, 16, 216–226 (1999)) or $^{125}$I-ABOPX (2200 Ci/mmol). To prepare $^{125}$I-ABOPX, 10 µL of 1 mM ABOPX in methanol/1 M NaOH (20:1) was added to 50 µL of 100 mM phosphate buffer, pH 7.3. One or 2 mCi of Na$^{125}$I was added, followed by 10 µL of 1 mg/mL chloramine-T in water. After incubation, 20 minutes at room temperature, 50 µL of 10 mg/mL Na-metabisulfite in water was added to quench the reaction. The reaction mixture was applied to a C18 HPLC column, eluting with a mixture of methanol and 5 mM phosphate, pH 6.0. After 5 min at 35% methanol, the methanol concentration was ramped to 100% over 15 min. Unreacted ABOPX eluted in 11–12 minutes; $^{125}$I-ABOPX eluted at 18–19 min in a yield of 50–60% with respect to the initial $^{125}$I.

In equilibrium binding assays the ratio of $^{127}$I/$^{125}$I-ABOPX was 10–20/1. Radioligand binding experiments were performed in triplicate with 20–25 µg membrane protein in a total volume of 0.1 mL HE buffer supplemented with 1 U/mL adenosine deaminase and 5 mM $MgCl_2$. The incubation time was 3 h at 21° C. Nonspecific binding was measured in the presence of 100 µM NECA. Competition experiments were carried out using 0.6 nM $^{125}$I-ABOPX. Membranes were filtered on Whatman GF/C filters using a Brandel cell harvester (Gaithersburg, Md.) and washed 3 times over 15–20 seconds with ice cold buffer (10 mM Tris, 1 mM $MgCl_2$, pH 7.4). $B_{max}$ and $K_D$ values were calculated by Marquardt's nonlinear least squares interpolation for single a site binding models. Marquardt, D. M., *J. Soc. Indust. Appl. Math.*, 11, 431–441.21 (1963). $K_i$ values for different compounds were derived from $IC_{50}$ values as described. Linden, J., *J. Cycl. Nucl. Res.*, 8, 163–172 (1982). Data from replicate experiments are tabulated as means±SEM.

At other Adenosine Receptors: [$^3$H]CPX. Bruns, R. F. et al., *Naunyn-Schmiedeberg's Arch. Pharmacol.*, 335, 59–63 (1987). $^{125}$I-ZM241385 and $^{125}$I-ABA were utilized in radioligand binding assays to membranes derived from HEK-293 cells expressing recombinant human $A_1$, $A_{2A}$ and $A_3$ ARs, respectively. Binding of [$^3$H]R-N$^6$-phenylisopropyladenosine. Schwabe, U. et al., *Naunyn-Schmiedeberg's Arch. Pharmacol.*, 313, 179–187 (1980). ([$^3$H]R-PIA, Amersham, Chicago, Ill.) to $A_1$ receptors from rat cerebral cortical membranes and of [$^3$H]CGS 21680. Jarvis, M. F. et al., *J. Pharmacol. Exp. Therap.*, 251, 888–893 (1989). (Dupont NEN, Boston, Mass.) to $A_{2A}$ receptors from rat striatal membranes was performed as described. Adenosine deaminase (3 units/mL) was present during the preparation of the brain membranes, in a pre-incubation of 30 min at 30° C., and during the incubation with the radioligands. All non-radioactive compounds were initially dissolved in DMSO, and diluted with buffer to the final concentration, where the amount of DMSO never exceeded 2%. Incubations were terminated by rapid filtration over Whatman GF/B filters, using a Brandell cell harvester (Brandell, Gaithersburg, Md.). The tubes were rinsed three times with 3 mL buffer each.

At least six different concentrations of competitor, spanning 3 orders of magnitude adjusted appropriately for the $IC_{50}$ of each compound, were used. $IC_{50}$ values, calculated with the nonlinear regression method implemented in (Graph-Pad Prism, San Diego, Calif.), were converted to apparent $K_i$ values as described. Linden, J., *J. Cycl. Nucl. Res.*, 8:163–172 (1982). Hill coefficients of the tested compounds were in the range of 0.8 to 1.1.

Functional Assay:

HEK-$A_{2B}$ cells from one confluent T75 flask were rinsed with $Ca^{2+}$ and $Mg^{2+}$-free Dulbecco's phosphate buffered saline (PBS) and then incubated in $Ca^{2+}$ and $Mg^{2+}$-free HBSS with 0.05% trypsin and 0.53 mM EDTA until the cells detached. The cells were rinsed twice by centrifugation at 250×g in PBS and resuspended in 10 mL of HBSS composed of 137 mM NaCl, 5 mM KCl, 0.9 mM $MgSO_4$, 1.4 mM $CaCl_2$, 3 mM $NaHCO_3$, 0.6 mM $Na_2HPO_4$, 0.4 mM $KH_2PO_4$, 5.6 mM glucose, and 10 mM HEPES, pH 7.4 and the $Ca^{2+}$-sensitive fluorescent dye indo-1-AM (5 µM) 37° for 60 min. The cells were rinsed once and resuspended in 25 mL dye-free HBSS supplemented with 1 U/ml adenosine deaminase and held at room temperature. Adenosine receptor antagonists prepared as 100×stocks in DMSO or vehicle was added and the cells and transferred to a 37° bath for 2 minutes. Then the cells (1 million in 2 ml) were transferred to a stirred cuvette maintained at 37° within an Aminco SLM 8000 spectrofluorometer (SML instruments, Urbana Ill.). The ratios of indo-1 fluorescence obtained at 400 and 485 nm (excitation, 332 nm) was recorded using a slit width of 4 nm. NECA was added after a 100 s equilibration period.

Cyclic AMP Accumulation

Cyclic AMP generation was performed in DMEM/HEPES buffer (DMEM containing 50 mM HEPES, pH 7.4, 37° C.). Each well of cells was washed twice with DMEM/HEPES buffer, and then 100 µL adenosine deaminase (final concentration 10 IU/mL) and 100 μL of solutions of rolipram and cilostamide (each at a final concentration of 10 μM) were added, followed by 50 μL of the test compound (appropriate concentration) or buffer. After 15 minutes, incubation at 37° C. was terminated by removing the medium and adding 200 μL of 0.1 M HCl. Acid extracts were stored at −20° C. until assay. The amounts of cyclic AMP were determined following a protocol which utilized a cAMP binding protein (PKA) [van der Wenden et al., 1995], with the following minor modifications. The assay buffer consisted of 150 mM $K_2HPO_4$/10 mM EDTA/0.2% BSA FV at pH 7.5. Samples (20 mL) were incubated for 90 minutes at 0° C. Incubates were filtered over GF/C glass microfiber filters in a Brandel M-24 Cell Harvester. The filters were additionally rinsed with 4 times 2 mL 150 mM $K_2HPO_4$/10 mM EDTA (pH 7.5, 4° C.). Punched filters were counted in Packard Emulsifier Safe scintillation fluid after 2 hours of extraction.

The data from the affinity testing for the compounds of the invention are reported in Tables 1, 2, 3 and 4. The data are reported as Ki in nM or % displacement of specific binding at the designated concentration (where "r" indicates rat cell receptors and "h" indicates human cell receptors).

The data reported for the $A_1$ term indicates the level of displacement of specific [$^3$H]R-PIA binding in rat brain membranes ($rA_1$) or recombinant human $A_1$ receptors ($hA_1$) in HEK 293 cells, expressed as $K_i \pm S.E.M.$ (n=3–5). The data reported for the $A_{2A}$ term is the level of displacement of specific [$^3$H]CGS 21680 binding in rat striatal membranes ($rA_{2A}$) or recombinant human $A_{2A}$ receptors ($hA_{2A}$) in HEK 293 cells, expressed as $K_i \pm S.E.M.$ (n=3–5). The data reported for the $A_{2B}$ term is the level of displacement of specific [$^{125}$I]ABOPX binding at human $A_{2B}$ receptors ($hA_{2B}$) expressed in HEK-293 cells, expressed as $K_i \pm S.E.M.$ (n=3–4). The $A_3$ term is the level of displacement of specific [$^{125}$I]ABA binding at human $A_3$ receptors ($hA_3$) expressed in HEK-293 cells, in membranes, expressed as $K_i \pm S.E.M.$ (n=3–4).

In Table 4 the data reported for the $A_{2A}$ term is the level of displacement of specific [$^3$H]CGS 21680 binding to rat striatal membranes ($rA_{2A}$) or [$^{125}$I]ABOPX binding to recombinant human $A_{2B}$ receptors ($hA_{2B}$) in HEK 293 cells, expressed as $K_i \pm S.E.M.$ in μm (n=3–6) or as a percentage of specific binding displaced by a solution of test compound, at the the designated concentration. In Table 4 the data reported for the $hA_3$ term is the level of displacement of specific [$^{125}$I]AB-MECA binding at human $A_3$ receptors expressed in HEK-293 cells, in membranes, expressed as $K_i \pm S.E.M.$ in μM (n=3–4).

TABLE 1

Affinities or antagonistic activities of xanthine derivatives in radioligand binding assays at $A_1$, $A_{2A}$, $A_{2B}$ and $A_3$ receptors.

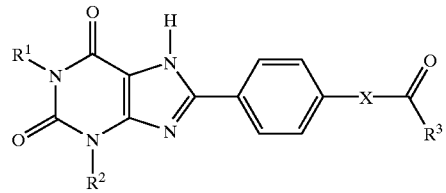

$K_i$ or $IC_{50}$ (nM)

| Compound | $R^1$, $R^2$ | X | $R^3$ | $rA_1$ | $rA_{2A}$ | $hA_{2B}$ | $hA_3$ | $hA_1/hA_{2B}$ | $hA_{2A}/hA_{2B}$ | $hA_3/hA_{2B}$ |
|---|---|---|---|---|---|---|---|---|---|---|
| 4a | n-Pr | $OCH_2$ | OH | 58<br>175 ± 57(h) | 2,200<br>595 ± 128(h) | 40 ± 4 | 3,910 ± 2,140<br>75,700 ±<br>6,500(r) | 4.4 | 15 | 98 |
| 4b | n-Pr | $OCH_2$ | O-Succinimide | 153 | 127 | 9.75 ± 4.80 | 227 | | | |
| 4c | n-Pr | $OCH_2$ | NHN-dimethylmaleiyl | 11.1 ± 2.4<br>3,030 ± 1,110(h) | 126 ± 41<br>1,970 ± 550(h) | 26.6 ± 4.0 | 670 ± 154 | 110 | 74 | 25 |
| 4d | n-Pr | $OCH_2$ | $NH(CH_2)_2NH_2$ | 1.2<br>6.82 ± 1.57(h) | 63<br>18.4 ± 0.03(h) | 7.75 ± 0.14 | 25.6 ± 5.0 | 0.9 | 2.4 | 3.3 |
| 5 | allyl | $OCH_2$ | OH | 756 ± 147<br>1,660 ± 580(h) | 4,290 ± 570<br>2,370 ± 290(h) | 141 ± 29(h) | 816 ± 91<br>173,000 ±<br>18,000(r) | 12 | 17 | 5.8 |
| 6 | n-butyl | $OCH_2$ | OH | 43.1 ± 9.9<br>149 ± 83(h) | 874 ± 107<br>2,540 ±<br>1,250(h) | 48.0 ± 16.9 | 90.3 ± 14.2<br>27,500 ±<br>2,500(r) | 3.1 | 53 | 1.9 |
| 7 | Bn | $OCH_2$ | OH | 679 ± 190 | 25 ± 3%<br>(100,000 nM)$^a$ | 1,760 ± 110 | | | | |
| 8 | n-Pr | CH=CH | OH | 15<br>140 ± 3(h) | 800<br>190 ± 71(h) | 60 ± 2 | 30 ± 14<br>15,000 ±<br>1,700(r) | 2.3 | 3.2 | 0.5 |
| 9 | c-HexylCH$_2$ | CH=CH | OH | 602 ± 24<br>4,890 ± 530(h) | <10%<br>(10,000 nM)$^a$<br>1,518 ± 980(h) | 199 ± 52 | 922 ± 399 | 25 | 7.6 | 4.6 |
| 10 | Bn | CH=CH | OH | 201 ± 23 | 4,450 ± 1,230 | 469 ± 23 | | | | |
| 71 | CH—CH=CH$_2$ | $OCH_2$ | NH—Ph(4-CN) | 61,200 ± 43,000 | 4,230 ± 340 | 9.53 ± 1.9 | 2680 ± 1810 | | | |

$^a$% Displacement of specific binding at the the designated concentration of test compound.

TABLE 2

Affinities or antagonistic activities of xanthine amide derivatives in radioligand binding assays[a] at $A_1$, $A_{2A}$, $A_{2B}$ and $A_3$ receptors.

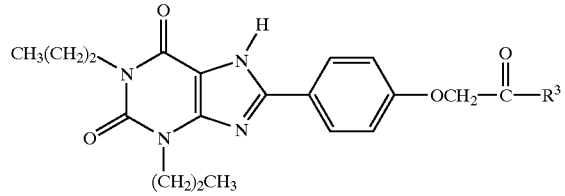

$K_i$ or $IC_{50}$ (nM)

| Compound | $R^3$ | $rA_1$ | $rA_{2A}$ | $hA_1$ | $hA_{2A}$ | $hA_{2B}$ | $hA_3$ | $hA_3/hA_{2B}$ | $hA_1/hA_{2B}$ | $hA_{2A}/hA_{2B}$ |
|---|---|---|---|---|---|---|---|---|---|---|
| 11 | NH$_2$ | 20.0 ± 3.8 | 76.3 ± 14.0 | | | 16.3 ± 4.2 | | | | |
| 12 | NH—Ph | 4.22 ± 0.88 | 45.6 ± 1.4 | 40.1 ± 5.1 | 25.8 ± 4.5 | 1.48 ± 0.63 | 137 ± 54 | 27 | 17 | 93 |
| 13 | NH—CH$_2$Ph | 5.02 ± 0.55 | 25.9 ± 7.6 | 54.7 ± 21.2 | 23.8 ± 5.71 | 2.04 ± 0.17 | 79.2 ± 17.8 | 27 | 12 | 39 |
| 14 | NH—CH(Ph)$_2$ | 120 ± 21 | 20 ± 8% (1000)[b] | | | 33.7 ± 17.0 | | | | |
| 15 | N(CH$_2$Ph)$_2$ | 167 ± 49 | 2,750 ± 800 | 690 ± 98 | 642 ± 198 | 9.88 ± 1.05 | 284 ± 14 | 70 | 65 | 29 |
| 16 | N(CH$_3$)Ph | 218 ± 80 | 497 ± 250 | | | 5.42 ± 1.71 | | | | |
| 17 | N(CH$_2$COOEt)$_2$ | 26.8 ± 2.4 | 999 ± 144 | | | 43.4 ± 8.4 | | | | |
| 18 | NH—Ph-(2-COCH$_3$) | 27.9 ± 1.6 | 434 ± 129 | 335 ± 64 | 431 ± 176 | 2.74 ± 1.01 | 61.9 ± 3.4 | 120 | 160 | 23 |
| 19 | NH—Ph-(3-COCH$_3$) | 439 ± 111 | 949 ± 394 | 234 ± 28 | 58.9 ± 7.1 | 4.92 ± 0.55 | 352 ± 69 | 48 | 12 | 72 |
| 20 | NH—Ph-(4-COCH$_3$) | 37.6 ± 4.0 | 548 ± 183 | 157 ± 8 | 112 ± 37 | 1.39 ± 0.30 | 230 ± 23 | 110 | 81 | 170 |
| 21 | NH—Ph-(4-COOCH$_3$) | 38.4 ± 3.9 | 541 ± 128 | 225 ± 9 | 3,100 ± 1540 | 3.93 ± 1.35 | 363 ± 148 | 57 | 790 | 92 |
| 22 | NH—Ph-(4-CONH$_2$) | 10.2 ± 2.5 | 683 ± 167 | | | 7.75 ± 1.11 | | | | |
| 23 | NH—Ph-(4-CONHCH$_3$) | 24.8 ± 1.8 | 98.1 ± 49.6 | | | 3.34 ± 0.51 | | | | |
| 24 | NH—Ph-(4-COOH) | 145 ± 28 | 220 ± 79 | | | 16.1 ± 4.7 | | | | |
| 25 | NH—Ph-(4-CH$_3$) | 17.5 ± 5.0 | 126 ± 38 | | | 1.88 ± 0.76 | | | | |
| 26 | NH—Ph-(4-OH) | 5.88 ± 1.06 | 63.3 ± 20.4 | | | 3.71 ± 0.76 | | | | |
| 27 | NH—Ph-(4-CN) | 16.8 ± 3.6 | 612 ± 287 | 403 ± 194 | 503 ± 10.8 | 1.97 ± 0.31 | 570 ± 184 | 210 | 260 | 290 |
| 28 | NH—Ph-(4-NO$_2$) | 13.1 ± 3.9 | 1,180 ± 360 | 57.0 ± 3.1 | 70.0 ± 10.7 | 1.52 ± 0.24 | 138 ± 17.1 | 38 | 46 | 91 |
| 29 | NH—Ph-(4-CF$_3$) | 44.6 ± 6.5 | 917 ± 258 | 61.2 ± 8.2 | 238 ± 28 | 2.14 ± 0.47 | 213 ± 94 | 29 | 110 | 100 |
| 30 | NH—Ph-(4-F) | 2.72 ± 0.51 | 988 ± 518 | 17.9 ± 4.5 | 16.6 ± 3.6 | 2.22 ± 0.19 | 391 ± 147 | 8.1 | 7.5 | 176 |
| 31 | NH—Ph-(4-Cl) | 6.35 ± 1.47 | 995 ± 550 | 49.7 ± 14.2 | 187 ± 38 | 2.47 ± 0.71 | 1,870 ± 370 | 20 | 400 | 760 |
| 32 | NH—Ph-(4-Br) | 7.46 ± 2.66 | 221 ± 36 | 73.5 ± 23.3 | 1,640 ± 660 | 2.35 ± 0.01 | 2,300 ± 420 | 31 | 700 | 980 |
| 33 | NH—Ph-(4-I) | 15.7 ± 4.2 | 152 ± 47 | 293 ± 67 | 5,140 ± 540 | 2.13 ± 0.12 | 1,270 ± 130 | 140 | 2,400 | 600 |

[a]The methods of each binding assay are described above.

TABLE 3

Affinities or antagonistic activities of miscellaneous xanthine derivatives in radioligand binding assays[a] at $A_1$, $A_{2A}$, $A_{2B}$ and $A_3$ receptors.

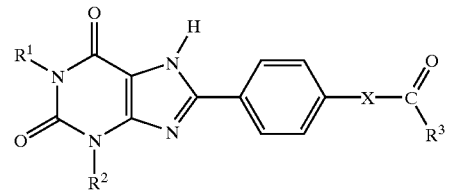

$K_i$ or $IC_{50}$ (nM)

| Compound | $R^1$, $R^2$ | X | $R^3$ | $rA_1$ | $rA_{2A}$ | $hA_{2B}$ | $hA_3$ |
|---|---|---|---|---|---|---|---|
| 34 | n-Pr | CH=CH | NHN-dimethylmalelyl | 3.94 ± 1.20 105 ± 5(h) | 406 ± 105 223 ± 55(h) | 16.7 ± 3.0 | 31.0 ± 3.1 |
| 35 | n-Pr | CH=CH | NH—Ph-(2-COCH$_3$) | 7.67 ± 2.20 | 143 ± 50 | 3.65 ± 0.98 | 121 ± 138 |
| 36 | c-HexMe | CH=CH | NH—Ph-(2-COCH$_3$) | (10,000 nM)[b] | (10,000 nM)[b] | (10,000 nM)[b] | |
| 37 | Bn | CH=CH | NH—Ph-(2-COCH$_3$) | 34,300 | (10,000 nM)[b] | (10,000 nM)[b] | |

TABLE 3-continued

Affinities or antagonistic activities of miscellaneous xanthine derivatives in radioligand binding assays[a] at $A_1$, $A_{2A}$, $A_{2B}$ and $A_3$ receptors.

$K_i$ or $IC_{50}$ (nM)

| Compound | $R^1$, $R^2$ | X | $R^3$ | $rA_1$ | $rA_{2A}$ | $hA_{2B}$ | $hA_3$ |
|---|---|---|---|---|---|---|---|
| 38 | Bn | $OCH_2$ | NH—Ph-(2-$COCH_3$) | (10,000 nM)[b] | (10,000 nM)[b] | (10,000 nM)[b] | |
| 39 | Et | $OCH_2$ | NH—Ph-(4-$CH_3$) | 34.9 ± 0.3 | 71.1 ± 7.7 | 1.78 ± 0.43 | (1000 nM)[b] |
| 40 | Et | $OCH_2$ | NH—Ph-(4-$CH_2$CONH—$(CH_2)_2NH_2$) | 65.0 ± 15.4 | 1370 ± 490 | 15.2 ± 6.8 | |

[a]The methods of each binding assay are as described above.
[b]<10% displacement of specific binding at the the designated concentration of test compound.

TABLE 4

Affinities of xanthine derivatives in radioligand binding assays[b] at rat $A_1$, rat $A_{2A}$, human $A_{2B}$, and human $A_3$ receptors, unless noted[a].

Ki (nM) or % displacement

| Compound | $R^9$ | $R^1$ | $rA_1$ | $rA_{2A}$ | $hA_{2B}$ | $hA_3$ | $rA_1/hA_{2B}$ |
|---|---|---|---|---|---|---|---|
| 4e | — | Pr | 51.6 ± 8.0, 230 ± 59(h)[a] | 128 ± 15, 342 ± 10(h)[a] | 18.7 ± 0.5, 34.5 ± 6.3[a] | 48.5 ± 0.8[a] | 2.8 |
| 4f | —$NH_2$ | Pr | 16.0 ± 0.5 | 63.8 ± 21.3 | 13.2 ± 5.9 | 498 ± 139 | 1.2 |
| 4l | —NH—$COCH_3$ | Pr | 6.51 ± 1.24, 125 ± 14(h)[a] | 227 ± 64, 186 ± 9(h)[a] | 65.4 ± 6.5, 33.8 ± 13.7[a] | 30.9 ± 8.2[a] | 0.10 |
| 42 | —NH—CH$_2$CH$_2$—CO—OH (succinamide) | Pr | 73.3 ± 22.0, 219 ± 3(h)[a] | 174 ± 32, 795 ± 98(h)[a] | 116 ± 10, 97.8 ± 3.3[a] | 173 ± 27 | 1.6 |
| 43 | succinimide-N— | Pr | 55.9 ± 25.1, 75.2 ± 5.5(h)[a] | 805 ± 44, 27.2 ± 8.6(h)[a] | 18.6 ± 6.1 | 766 ± 176 | 3.0 |
| 44 | 3-(NHCOCF$_3$)-succinimide-N— | Pr | 74.3 ± 6.6 | 139 ± 32 | 30.2 ± 0.5 | 1560 | 2.5 |

TABLE 4-continued

Affinities of xanthine derivatives in radioligand binding assays[b] at rat $A_1$, rat $A_{2A}$, human $A_{2B}$, and human $A_3$ receptors, unless noted[a].

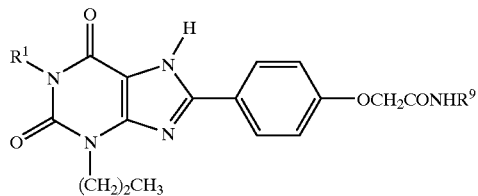

| | | | Ki (nM) or % displacement | | | | |
|---|---|---|---|---|---|---|---|
| Compound | R[9] | R[1] | rA$_1$ | rA$_{2A}$ | hA$_{2B}$ | hA$_3$ | rA$_1$/hA$_{2B}$ |
| 45 | (3-Ph-glutarimide) | Pr | 3.87 ± 1.20 | 21.4 ± 6.1 | 3.86 ± 0.7 | 151 ± 99 | 1.0 |
| 46 | (3-methylmaleimide) | Pr | 203 ± 41 | 1230 ± 270 | 144 ± 11 | 551 ± 106 | 1.4 |
| 47 | (3,4-dimethylmaleimide) | Pr | 11.1 ± 2.4, 3030 ± 1110(h)[a] | 126 ± 41, 1970 ± 550(h)[a] | 19.4 ± 6.2, 33.8 ± 1.9[a] | 670 ± 154[a] | 0.57 |
| 48 | (3,4-dimethylmaleimide) | H | 3590 ± 920, 8080 ± 720(h)[a] | 36 ± 4% (100,000 nM)[c], 5480 ± 920(h)[a] | 1800 ± 0, 1900 ± 280[a] | 14,200 ± 11,500[a] | 2.0 |
| 49 | (3-Ph-maleimide) | Pr | 225 ± 76 | 1540 ± 280 | 66.7 ± 37.0 | 748 ± 234 | 3.4 |
| 50 | (3,4-diPh-maleimide) | Pr | 95.8 ± 25.1 | 2100 ± 630 | 27.9 ± 8.5 | 3450 ± 1470 | 3.4 |
| 51 | (cyclohex-3-ene-1,2-dicarboxamide with HO$_2$C) | Pr | 134 ± 19 | 813 ± 299 | 51.0 ± 7.0 | 1060 ± 150 | 2.6 |

TABLE 4-continued

Affinities of xanthine derivatives in radioligand binding assays[b] at rat $A_1$, rat $A_{2A}$, human $A_{2B}$, and human $A_3$ receptors, unless noted[a].

[Structure: xanthine core with $R^1$ at N1, H at N7, $(CH_2)_2CH_3$ at N3, and 8-aryl group = phenyl-OCH$_2$CONHR$^9$]

| Compound | R⁹ | R¹ | rA₁ | rA₂ₐ | hA₂ᵦ | hA₃ | rA₁/hA₂ᵦ |
|---|---|---|---|---|---|---|---|
| 52 | N-methyl-4,5-dihydrophthalimide | Pr | 36.4 ± 6.2<br>129 ± 20(h)[a] | 689 ± 477<br>301 ± 31(h)[a] | 10.0 ± 3.0 | 370 ± 190 | 3.6 |
| 53 | —NH-cyclopentane-1,2-dicarboxyl (HO₂C) | Pr | 81.7 ± 31.2 | 708 ± 169 | 78.5 ± 20.5 | 1180 ± 700 | 1.0 |
| 54 | N-methyl-bicyclic imide (cyclopentane-fused) | Pr | 41.3 ± 6.4 | 1160 ± 337 | 21.5 ± 1.5 | 309 ± 88 | 1.9 |
| 55 | —NH-cyclohexene-1,2-dicarboxyl (HO₂C) | Pr | 47.2 ± 6.8<br>145 ± 11(h)[a] | 422 ± 136<br>95.6 ± 16.8(h)[a] | 17.3 ± 6.3 | 438 ± 109 | 2.7 |
| 56 | N-methyl-tetrahydrophthalimide | Pr | 61.9 ± 11.3 | 415 ± 157 | 35.8 ± 0.7 | 245 ± 45 | 1.7 |
| 57 | N-methyl-phthalimide | Pr | 26.3 ± 2.3,<br>210 ± 42(h)[a] | 392 ± 117,<br>359 ± 21(h)[a] | 64.4 ± 0.8,<br>46.4 ± 14.5[a] | 147 ± 21[a] | 0.41 |
| 58 | N-methyl-glutarimide | Pr | 14.0 ± 2.3 | 135 ± 39 | 22.0 ± 5.5 | 200 ± 45 | 0.6 |

TABLE 4-continued

Affinities of xanthine derivatives in radioligand binding assays[b] at rat $A_1$, rat $A_{2A}$, human $A_{2B}$, and human $A_3$ receptors, unless noted[a].

[Structure: xanthine core with $R^1$ at N1, H at N7, (CH$_2$)$_2$CH$_3$ at N3, and 8-aryl-OCH$_2$CONHR$^9$ substituent]

| Compound | R$^9$ | R$^1$ | rA$_1$ | rA$_{2A}$ | hA$_{2B}$ | hA$_3$ | rA$_1$/hA$_{2B}$ |
|---|---|---|---|---|---|---|---|
| 59 | [glutarimide-OH] | Pr | 41.2 ± 16.6 | 164 ± 61 | 25.7 ± 5.5 | 290 ± 88 | 1.6 |
| 60 | [—NH-CH(CH$_2$-CO$_2$H)-CO-NHCOCF$_3$ (S)] | Pr | 70.8 ± 30.9 | 872 ± 412 | 24.8 ± 7.3 | 430 ± 44 | 2.9 |
| 61 | [glutarimide-NHCOCF$_3$ (S)] | Pr | 53.5 ± 6.5<br>149 ± 6(h)[a] | 440 ± 106<br>178 ± 20(h)[a] | 13.0 ± 3.5 | 726 ± 245 | 4.1 |
| 62 | [—NH-CO-CH(NHCOO(CH$_3$)$_3$)-CH$_2$CH(CH$_2$)$_2$ (S)] | Pr | 197 ± 67 | 2750 ± 950 | 47.5 ± 2.5 | 195 ± 84 | 4.1 |
| 63 | [—NH-CO-CH(NHCOO(CH$_3$)$_3$)-(CH$_2$)$_2$SCH$_3$ (S)] | Pr | 113 ± 27 | 524 ± 285 | 39.7 ± 13.6 | 690 ± 570 | 2.8 |
| 64 | Cbz-(Gly)$_2$-NH— | Pr | 36.0 ± 6.6<br>200 ± 22(h)[a] | 609 ± 95<br>830 ± 84(h)[a] | 10.8 ± 5.0 | 323 ± 47 | 3.3 |

[a]$K_i$ values were determined in radioligand binding assays at recombinant human $A_1$ and $A_{2A}$ receptors expressed in HEK-293 cells vs [$^3$H]CPX and [$^{125}$I]ZM241385, respectively. Affinity of xanthine derivatives at human $A_{2B}$ receptors expressed in HEK-293 cells was determined using [$^{125}$I]-ABOPX. Affinity at recombinant human $A_3$ receptors expressed in HEK-293 cells was determined using [$^{125}$I]ABA.
[b]The methods of each binding assay are as described above.
[c]% Displacement of specific binding at the the designated concentration of test compound.

Figure 2A:
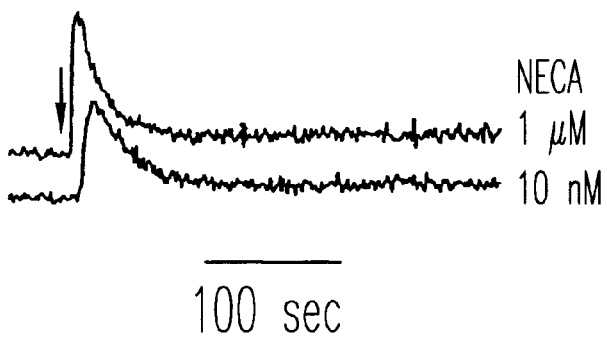
FIG. 2 is a graphic illustration of the inhibition by several selective $A_{2B}$ AR antagonists of NECA-stimulated calcium mobilization in HEK-$A_{2B}$ cells. Cells were loaded with Indo 1 for 1 hour. The A) curves indicate calcium mobilization in response to 10 nM and 1 μM NECA added at the arrow. The B) curves indicate calcium mobilization in response to 10 nM NECA added at the arrow in cells pretreated for two minutes with 1% DMSO (control) or with 100 nM of the indicated antagonists. The results are typical of replicate experiments.
Figure 2B:
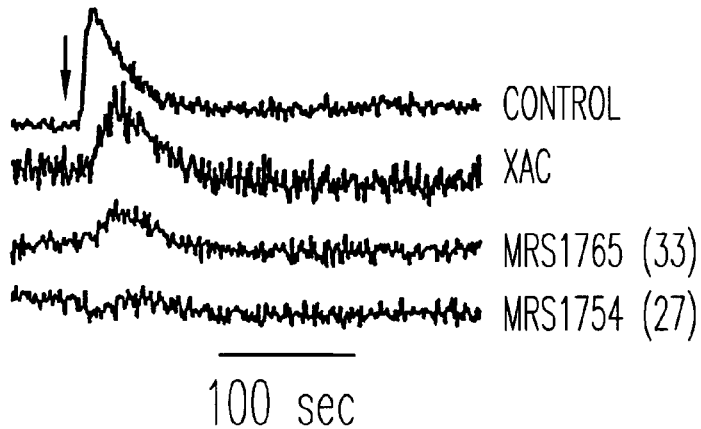
Figure 3:
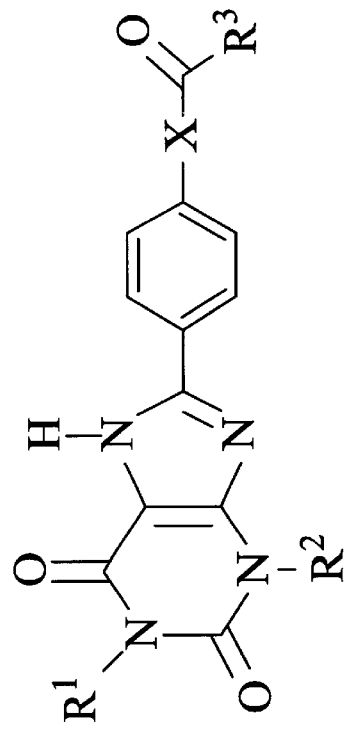
FIG. 3 illustrates the synthesis of amide derivatives of xanthine carboxylic acid congeners of the invention.
Figure 3:
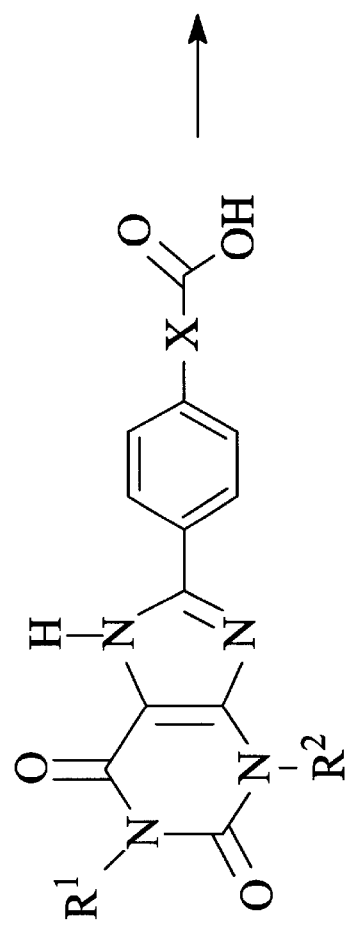

The potency of the xanthine derivatives at human $A_{2B}$ receptors was evaluated using two binding assays. Tables 1, 2 and 3 illustrate the results from the anilide compounds. Table 4 illustrates the results from the hydrazide compounds. FIG. 2 shows functional inhibiton by anilide compounds. The $K_i$ values of the xanthine derivatives were determined in displacement of binding of two non-selective radioligands 4-(2-[7-amino-2-{furyl}{1,2,4}triazolo{2,3-a}{1,3,5}triazin-5-ylaminoethyl)-phenol ([$^3$H]ZM241385), and $^{125}$I-3-(4-amino-3-iodobenzyl)-8-phenyloxyacetate-1-propyl-xanthine ($^{125}$I-ABOPX), at human $A_{2B}$ receptors stably expressed in HEK-293 cell membranes. The results obtained with these two radioligands were nearly identical. In order to determine selectivity, the xanthines were evaluated using standard binding assays at $A_1$, $A_{2A}$, and $A_3$ receptors. The initial screening utilized rat brain $A_1/A_{2A}$ receptors (with radioligands [$^3$H]R-PIA and [$^3$H]CGS21680), and selected compounds were examined at the recombinant human subtypes, using [$^3$H]8-cyclopentyl-1,3-dipropylxanthine ([$^3$H]CPX) ($A_1$, See Bruns, R. F., et al., Naunyn-Schmiedeberg's Arch. Pharmacol. 1987, 335, 59–63.) and $^{125}$I-4-(2-[7-amino-2-[2-furyl]-[1,2,4]triazolo[2,3-α][1,3,5]-triazin-5-yl-amino]-ethyl)phenol ($^{125}$I-ZM241385) ($A_2$). Affinity at cloned human $A_3$ receptors expressed in HEK-293 cells was determined using $N^6$-(4-amino-3-[$^{125}$I]iodobenzyl)-adenosine ($^{125}$I-ABA) or $N^6$-(4-amino-3-iodobenzyl)-adenosine-5'-N-methyluronamide ($^{125}$I-AB-MECA).

The 8-(4-Phenylacrylic) acid derivatives, 8–10, tended to be more potent at $A_1$ receptors and less potent at $A_{2B}$ receptors than the 8-(4-carboxymethyloxy-phenyl) derivatives. The 1,3-dicyclohexylmethyl derivative, 9, for example, was more selective for $A_{2B}$ receptors. A primary carboxamide, 11, was more potent than the carboxylic acid, 4a, at $A_1$ (3-fold) and $A_{2A}$ (29-fold) receptors, and equipotent at $A_{2B}$ receptors.

The adenosine receptor affinities of aryl, compounds 12 and 18–33, alkyl, compound 17, and aralkyl, compounds 13–16, amides of 4a were compared. A benzyl amide, compound 13, and simple anilides had the highest affinity of binding, in the nanomolar range, to human $A_{2B}$ receptors. Selectivities for the human $A_{2B}$ versus rat $A_1$ receptors ranged from 1-(compound 30) to 27-(compound 20) fold, while comparisons within the same species (human) generally led to greater selectivities. Anilides substituted in the p-position with groups such as nitro, cyano, and acetyl, displayed the highest selectivity. An N-methyl anilide of 4a, compound 16, was 40- and 92-fold selective for human $A_{2B}$ receptors versus rat $A_1/A_{2A}$ receptors, thus the N-methylation reduced affinity by 3.7-fold but increased selectivity. An o-substituted acetophenone, compound 18 was 120-, 160-, and 23-fold selective for human $A_{2B}$ receptors versus human $A_1/A_{2A}/A_3$ receptors and 10-, and 160-fold selective versus rat $A_1/A_{2A}$ receptors. The p-substituted acetophenone, compound 20, was more potent at $A_{2B}$ receptors than the corresponding o- and m-isomers. Other highly potent and moderately selective $A_{2B}$ antagonists were a p-trifluoromethyl derivative, compound 29 ($K_i$ value 2.14 nM), and a p-cyanoanilide, compound 27 ($K_i$ value 1.97 nM), which was highly selective versus the other human subtypes, but only 8.5-fold selective versus rat $A_1$ receptors. The p-cyanoanilide, 27, was tritiated on the 1,3-dipropyl groups and serves as a selective radio ligand for $A_{2B}$ receptors. A p-nitro derivative, compound 28, bound to human $A_{2B}$ receptors with a $K_i$ of 1.52 nM but was only 35-fold selective versus human $A_1$ receptors. A p-iodo derivative, compound 33 ($K_i$ value 2.13 nM), was 140-, 2400-, and 600-fold selective for human $A_{2B}$ receptors versus human $A_1/A_{2A}/A_3$ receptors. Substitution of the 1,3-dipropyl groups with ethyl, as in compounds 40 and 41, offered no disadvantage for selectivity, but high affinities were maintained.

The functional effects of several selective $A_{2B}$ antagonists in inhibiting the effects of NECA in HEK-$A_{2B}$ cells were examined (FIG. 2). Several selective $A_{2B}$ adenosine receptor antagonists at 100 nM nearly completely inhibited NECA-stimulated calcium mobilization. In comparison, XAC (8-[4-[[[[(2-aminoethyl)amino]carbonyl]methyl]oxy]phenyl]-1,3-dipropylxanthine), which has a $K_i$ value of 12.3 nM in binding to human $A_{2B}$, (See de Zwart, M.; et al., Nucleos. Nucleot. 1998, 17, 969–986.) inhibited the NECA-stimulated calcium mobilization effect by about half. Thus, the potency of the xanthines in the functional assay was parallel to results from the binding assay. The 1,2-dimethylmaleimide derivative, 47, bound to human $A_{2B}$, receptors with a $K_i$ of 19 nM and proved to be selective vs. human $A_1/A_{2A}/A_3$ receptors by 160-, 100-, and 35-fold, respectively Other potent and selective $A_{2B}$ antagonists were a tetrahydrophthaloyl derivative 52 ($K_i$ value 10 nM) and amino acid conjugates of the XCC-hydrazide, i.e., the glutarimide 61 ($K_i$ value 13 nM) and protected dipeptide 64 ($K_i$ value 11 nM). Compound 55 displayed a $K_i$ value of 17 nM. Other derivatives displaying selectivity for $A_{2B}$ receptors, but with less potency ($K_i$ values in nM) were compounds: 44 (30), 49 (67), 50 (28), 60 (25), 62 (48), and 63 (40).

Synthesis and Characterization

Compounds 4a, 4b, 4c, 11, 25, and 26 were synthesized as reported in Jacobson, et al., J. Med. Chem. 1985, 28, 1334–1340. Compound 5, 6, 7 and 10 were synthesized as reported in Kim, H. O.; et al., J. Med. Chem. 1994, 37, 3373–3382. Compound 39 and 40 were synthesized as reported in Jacobson, K. A et al., J. Med. Chem. 1987, 30, 211–214. R-PIA, NECA, XAC, and 2-chloroadenosine were purchased from Research Biochemicals International (Natick, Mass.). All other agents were purchased from Aldrich (St. Louis, Mo.).

Proton nuclear magnetic resonance spectroscopy was performed on a Varian GEMINI-300 spectrometer and spectra were taken in DMSO-$d_6$ or $CDCl_3$. Unless noted, chemical shifts are expressed as ppm downfield from tetramethylsilane or relative ppm from DMSO (2.5 ppm). Chemical-ionization (CI) mass spectrometry was performed with a Finnigan 4600 mass spectrometer, and Electron-impact (EI) mass spectrometry with a VG7070F mass spectrometer at 6 kV for high resolution mass. FAB (fast atom bombardment) mass spectrometry was performed with a JEOL SX102 spectrometer using 6-kV Xe atoms.

Elemental analysis (±0.4% acceptable) was performed by Atlantic Microlab Inc. (Norcross, Ga.). All melting points were determined with a Unimelt capillary melting point apparatus (Arthur H. Thomas Co., PA) and were uncorrected. All xanthine derivatives were homogeneous as judged using TLC (MK6F silica, 0.25 mm, glass backed, Whatman Inc., Clifton, N.J.). All xanthine derivatives tested in binding assays were shown to be homogeneous by TLC (MK6F silica, 0.25 mm, glass backed, Whatman Inc., Clifton, N.J.). NMR and mass spectra were shown to be consistent with the assigned structure.

Example 1

General Procedure for the Preparation of Amide Derivatives of 8-[4-[[[Carboxyl]methyl]oxy] phenyl]-1,3-dipropylxanthine Analogs 4a, 7–10 (Collectively "XCC")

Method A (Carbodiimide)

A solution of XCC (0.0517 mmole), the desired amine compound (0.103 mmole), EDAC (20 mg, 0.103 mmole), and DMAP (4 mg, 0.032 mmole) in 2 mL of anhydrous DMF/$CH_2Cl_2$ (1:1 v/v) was stirred at room temperature for 24 hours. The mixture was evaporated to dryness under reduced pressure. The residue was purified by preparative silica gel TLC ($CHCl_3$:MeOH=20:1) and crystallization in MeOH/ether or MeOH/$CH_2Cl_2$ to afford the desired compounds (12–14, 18, 36).

Method B (BOP-Cl)

A solution of XCC (0.0517 mmole), the desired amine compound (0.103 mmole), BOP-Cl (14 mg, 0.0517 mmole), and triethylamine (20 μl, 0.206 mmole) in 2 mL of anhydrous $CH_2Cl_2$ was stirred at room temperature for 24 hours. The mixture was treated according to the same procedure as Method A for purification of the desired compounds. (15, 17, 19, 20, 38)

Method C (Acid Chloride)

A solution of XCC (0.0517 mmole) in 1 mL of thionyl chloride was stirred at 70° C. for 4 hours. The excess thionyl chloride was removed with a nitrogen stream. To the residue was added a solution of the desired amine compound (0.103 mmole) in 1 mL of anhydrous pyridine and 1 mL of anhydrous $CH_2Cl_2$. The mixture was stirred at room temperature for 24 hours. The mixture was subjected to the same procedure as described in Method A for purification of the desired compounds. (16, 21, 22, 27–35, 37)

Example 2

General Procedure for the Preparation of Xanthine Hydrazide Derivatives

Figure 4:
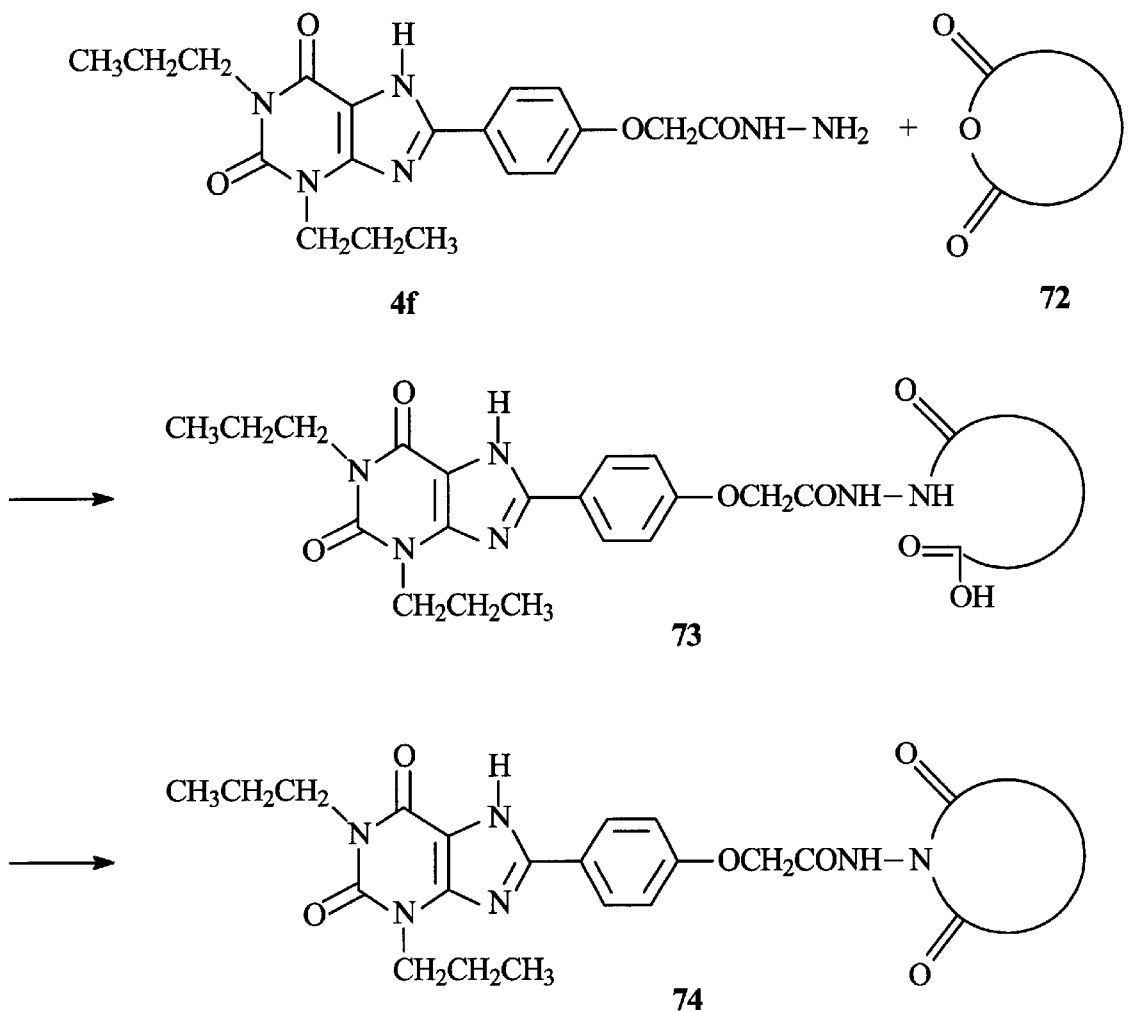
FIG. 4 illustrates the synthesis of hydrazide derivatives of xanthine carboxylic acid congeners of the invention.
Figure 5:
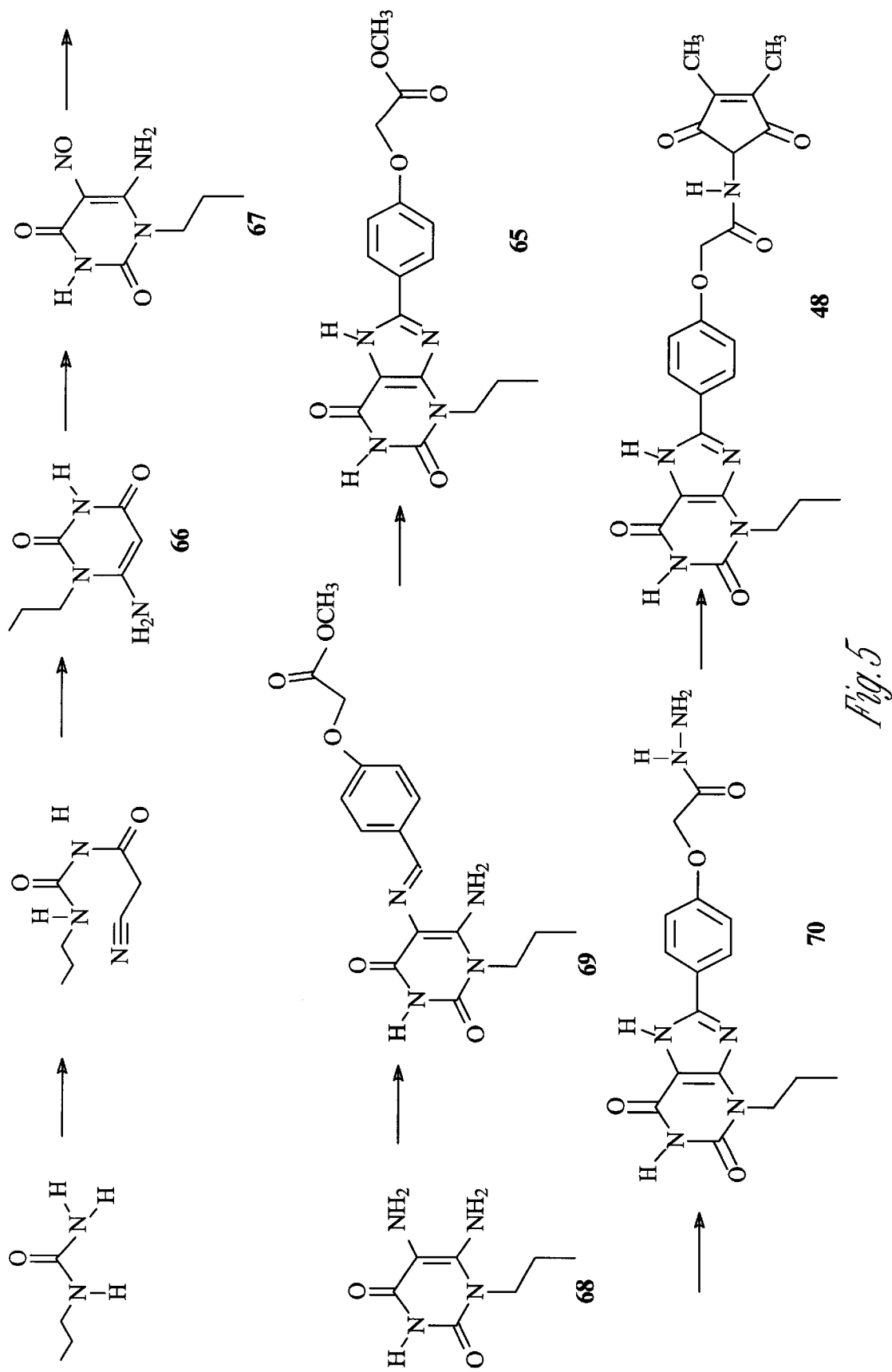
FIG. 5 illustrates the synthesis of hydrazide derivatives of xanthine carboxylic acid congeners of the invention.

The hydrazide of XCC, 4f, was acylated with a variety of mono- and dicarboxylic acids. Cyclization reactions were carried out for dicarboxylic acids, in two steps using an anhydride, (compound 72, FIG. 4), for acylation, leading to imide (5- or 6-membered ring) derivatives. The final step of ring-closure of 73 to 74 was effected at 50° C., using excess carbodiimide and 1-hydroxybenzo-triazole as catalyst. In some cases, where symmetric dicarboxylic acids were used, it was possible to isolate both the open structure, 73, and the cyclized imide form, 74. Pairs of open and cyclized derivatives of symmetric dicarboxylic acids prepared include compounds 51–56. Also, the glutamic acid derivative 60, was prepared using orthogonal protecting and the corresponding imide, 61. An 8-phenyl analogue, 48, of enprofylline was synthesized by standard methods from the asymmetric urea, (FIG. 5).

A. Carboxyalkyl Amide Derivatives

A mixture of compound 4f (10 mg, 0.025 mmol), and 2 equivalents of anhydride were stirred in 1 mL of DMF for 6–24 hours. The reaction mixture was concentrated to dryness, and the residue was purified on preparative TLC (CHCl$_3$:MeOH=10:1) to afford the corresponding carboxyalkylamide derivative as a white solid with 40–70% yield. (compounds 41, 42, 51, 53, 55)

B. Cyclic Imide Derivatives

A mixture of compound 4f (10 mg, 0.025 mmol), 1.5–2.0 equivalents of anhydride and 1 equivalent of DIPEA were stirred in 1 mL of DMF at room temperature. When the starting material 4f disappeared, as judged by TLC, a mixture of 2–3 equivalents of HOBt, EDAC, and DIPEA, dissolved in 0.5 mL of DMF, was added. The mixture was stirred at room temperature or at 50° C. for 6–24 hours. The reaction mixture was concentrated to dryness, and the residue was purified on preparative TLC (CHCl$_3$:MeOH=10:1) to afford the cyclic imide derivative as a white solid, 40–70% yield. (compounds 43, 44, 45, 46, 47, 48, 49, 50, 52, 54, 56, 57, 58, and 59)

C. Coupling with Activated N-protected Amino Acids

A mixture of compound 4f (10 mg, 0.025 mmol), 1.5–2.0 equivalents of activated (hydroxy-succinimide or 4-nitrophenyl ester) N-protected amino acid and 1 equivalent of DIPEA and DMAP, in 1 mL of DMF, was stirred at 25–50° C. for 8–24 hours. The reaction mixture was concentrated to dryness. The residue was purified by preparative TLC (CHCl$_3$:MeOH=10: 1) to afford the product as a white solid, 40–70% yield. (compounds 62, 63 and 64)

Example 3

8-[4-[(Carboxymethyl)oxy]phenyl]-1,3-dibenzyl-xanthine (7)

$^1$H NMR (DMSO-d$_6$) 4.23 (s, 2H, —OCH$_2$—), 5.10 (s, 2H, —NCH$_2$—), 5.23 (s, 2H, —NCH$_2$—), 6.88 (d, 2H, J=8.8 Hz, Ar), 7.22–7.41 (m, 10H, 2×-Ph), 8.01 (d, 2H, J=8.8 Hz, Ar).

Example 4

8-(4-(2-Carboxy-trans-vinyl)phenyl)-1,3-dibenzyl-xanthine (10)

$^1$H NMR (DMSO-d$_6$) 5.12 (s, 2H, —NCH$_2$—), 5.26 (s, 2H, —NCH$_2$—), 6.63 (d, 1H, J=15.6 Hz, —CH=), 7.22–7.43 (m, 10H, 2×-Ph), 7.63 (d, 1H, J=15.6 Hz, —CH=), 7.84 (d, 2H, J=8.8 Hz, Ar), 8.17 (d, 2H, J=8.8 Hz, Ar).

Example 5

8-[4-[(Phenylcarbamoylmethyl)oxy]phenyl]-1,3-di-(n-propyl)-xanthine (12)

$^1$H NMR (DMSO-d$_6$). 0.89 (2t, 6H, J=7.8 Hz, 2×—CH$_3$), 1.58 and 1.74 (2m, 4H, 2×—CH$_2$—), 3.87 and 4.02 (2t, 4H, J=6.8 Hz, 2×—NCH$_2$—), 4.80 (s, 2$_{H, \text{—OCH2}}$—), 7.06–7.12 (m, 1H, -Ph), 7.14 (d, 2H, J=8.8 Hz, Ar), 7.33 (t, 2H, J=7.8 Hz, -Ph), 7.64 (d, 2H, J=7.8 Hz, -Ph), 8.09 (d, 2H, J=8.8 Hz, Ar), 10.13 (s, 1H, —NH).

Example 6

8-[4-[(Benzylcarbamoylmethyl)oxy]phenyl]-1,3-di-(n-propyl)-xanthine (13)

$^1$H NMR (DMSO-d$_6$). 0.89 (2t, 6H, J=7.8 Hz, 2×—CH$_3$), 1.58 and 1.74 (2m, 4H, 2×—CH$_2$—), 3.87 and 4.02 (2t, 4H, J=6.8 Hz, 2×—NCH$_2$—), 4.36 (d, 2H, J=5.9 Hz, —NH—CH$_2$—), 4.80 (s, 2H, —OCH$_2$—), 7.12 (d, 2H, J=8.8 Hz, Ar), 7.22–7.34 (m, 5H, -Ph), 8.08 (d, 2H, J=8.8 Hz, Ar), 8.70 (t, 1H, J=5.9 Hz, —NH—).

Example 7

8-[4-[(Diphenylmethylcarbamoylmethyl)oxy]phenyl]-1,3-di-(n-propyl)xanthine (14)

$^1$H NMR (DMSO-d$_6$). 0.89 (2t, 6H, J=7.8 Hz, 2×—CH$_3$), 1.58 and 1.74 (2m, 4H, 2×—CH$_2$—), 3.87 and 4.02 (2t, 4H, J=6.8 Hz, 2×—NCH$_2$—), 4.73 (s, 2H, —OCH$_2$—), 6.20 (d, 1H, J=8.8 Hz, —NH—CH$_2$—), 7.08 (d, 2H, J=8.8 Hz, Ar), 7.23–7.37 (m, 10H, 2×-Ph), 8.07 (d, 2H, J=8.8 Hz, Ar), 9.06 (d, 1H, J=8.8 Hz, —NH—).

Example 8

8-[4-[(Dibenzylcarbamoylmethyl)oxy]phenyl]-1,3-di-(n-propyl)-xanthine (15)

$^1$H NMR (DMSO-d$_6$). 0.89 (2t, 6H, J=7.8 Hz, 2×—CH$_3$), 1.58 and 1.74 (2m, 4H, 2×—CH$_2$—), 3.87 and 4.02 (2t, 4H, J=6.8 Hz, 2×—NCH$_2$—), 4.52 (s, 2H, —NCH$_2$—), 4.59 (s, 2H, —NCH$_2$—), 5.03 (s, 2H, —OCH$_2$—), 6.99 (d, 2H, J=8.8 Hz, Ar), 7.22–7.44 (m, 10H, 2×-Ph), 8.05 (d, 2H, J=8.8 Hz, Ar).

Example 9

8-[4-[(N-Methyl-N-phenylcarbamoylmethyl)oxy]phenyl]-1,3-di-(n-propyl)xanthine (16)

$^1$H NMR (DMSO-d$_6$). 0.89 (2t, 6H, J=7.8 Hz, 2×—CH$_3$), 1.58 and 1.74 (2m, 4H, 2×—CH$_2$—), 3.22 (s, 3H, —NCH$_3$), 3.88 and 4.01 (2t, 4H, J=6.8 Hz, 2×—NCH$_2$—), 4.54 (s, 2H, —OCH$_2$—), 6.91 (bs, 2H, Ar), 7.30–7.55 (m, 5H, -Ph), 8.03 (d, 2H, J=8.8 Hz, Ar).

Example 10

8-[4-[(N,N-bis(Ethoxycarbonylmethyl)carbamoylmethyl)oxy]-phenyl]-1,3-di-(n-propyl)xanthine (17)

$^1$H NMR (DMSO-d$_6$). 0.89 (2t, 6H, J=7.8 Hz, 2×—CH$_3$), 1.20 (2t, 6H, J=6.8 Hz, 2×—CH$_3$), 1.58 and 1.74 (2m, 4H, 2×—CH$_2$—), 3.87 and 4.02 (2t, 4H, J=6.8 Hz, 2×—NCH$_2$—), 4.06–4.20 (m, 4H, —OCH$_2$—), 4.11 (s, 2H, —NCH$_2$—), 4.38 (s, 2H, —NCH$_2$—), 4.94 (s, 2H, —OCH$_2$—), 7.00 (d, 2H, J=8.8 Hz, Ar), 8.05 (d, 2H, J=8.8 Hz, Ar).

Example 11

8-[4-[((2-Acetylphenyl)carbamoylmethyl)oxy]phenyl]-1,3-di-(n-propyl)xanthine (18)

$^1$H NMR (DMSO-d$_6$). 0.89 (2t, 6H, J=7.8 Hz, 2×—CH$_3$), 1.59 and 1.74 (2m, 4H, 2×—CH$_2$—), 3.87 and 4.02 (2t, 4H, J=6.8 Hz, 2×—NCH$_2$—), 4.70 (s, 3H, —COCH$_3$), 4.72 (s, 2H, —OCH$_2$—), 7.15 (d, 2H, J=8.8 Hz, Ar), 7.56 (t, 1H, J=6.8 Hz, Ar), 7.69 (t, 1H, J=6.8 Hz, Ar), 8.02 (d, 2H, J=6.8 Hz, Ar), 8.11 (d, 2H, J=8.8 Hz, Ar), 8.48 (m, 1H, —NH—).

Example 12

8-[4-[((3-Acetylphenyl)carbamoylmethyl)oxy]phenyl]-1,3-di-(n-propyl)xanthine (19)

$^1$H NMR (DMSO-d$_6$). 0.89 (2t, 6H, J=7.8 Hz, 2×—CH$_3$), 1.59 and 1.74 (2m, 4H, 2×—CH$_2$—), 2.57 (s, 3H, —COCH$_3$), 3.87 and 4.02 (2t, 4H, J=6.8 Hz, 2×—NCH$_2$—), 4.82 (s, 2H, —OCH$_2$—), 7.16 (d, 2H, J=8.8 Hz, Ar), 7.50 (t, 1H, J=7.8 Hz, Ar), 7.71 (d, 1H, J=7.8 Hz, Ar), 7.92 (d, 1H, J=7.8 Hz, Ar), 8.10 (d, 2H, J=8.8 Hz, Ar), 8.24 (s, 1H, Ar), 10.36 (s, 1H, —NH—).

Example 13

8-[4-[((4-Acetylphenyl)carbamoylmethyl)oxy]phenyl]-1,3-di-(n-propyl)xanthine (20)

$^1$H NMR (DMSO-d$_6$). 0.89 (2t, 6H, J=7.8 Hz, 2×—CH$_3$), 1.58 and 1.74 (2m, 4H, 2×—CH$_2$—), 2.54 (s, 3H, —COCH$_3$), 3.87 and 4.02 (2t, 4H, J=6.8 Hz, 2×—NCH$_2$—), 4.85 (s, 2H, —OCH$_2$—), 7.15 (d, 2H, J=8.8 Hz, Ar), 7.79 (d, 2H, J=7.8 Hz, Ar), 7.96 (d, 2H, J=7.8 Hz, Ar), 8.09 (d, 2H, J=8.8 Hz, Ar), 10.48 (s, 1H, —NH—).

Example 14

8-[4-[((4-Methoxycarbonyl)phenylcarbamoylmethyl)oxy]phenyl]-1,3-di-(n-propyl)xanthine (21)

$^1$H NMR (DMSO-d$_6$). 0.89 (2t, 6H, J=7.8 Hz, 2×—CH$_3$), 1.58 and 1.74 (2m, 4H, 2×—CH$_2$—), 3.83 (s, 3H, —OCH$_3$), 3.86 and 4.02 (2t, 4H, J=6.8 Hz, 2×—NCH$_2$—), 4.85 (s, 2H, —OCH$_2$—), 7.14 (d, 2H, J=8.8 Hz, Ar), 7.79 (d, 2H, J=7.8 Hz, Ar), 7.96 (d, 2H, J=7.8 Hz, Ar), 8.09 (d, 2H, J=8.8 Hz, Ar), 10.50 (s, 1H, —NH—).

Example 15

8-[4-[((4-Carbamoyl)phenylcarbamoylmethyl)oxy]phenyl]-1,3-di-(n-propyl)xanthine (22)

$^1$H NMR (DMSO-d$_6$). 0.89 (2t, 6H, J=7.8 Hz, 2×—CH$_3$), 1.58 and 1.74 (2m, 4H, 2×—CH$_2$—), 3.87 and 4.02 (2t, 4H, J=6.8 Hz, 2×—NCH$_2$—), 4.82 (s, 2H, —OCH$_2$—), 7.14 (d, 2H, J=8.8 Hz, Ar), 7.26 (bs, 1H, —NH$_2$), 7.70 (d, 2H, J=7.8 Hz, Ar), 7.85 (m, 3H, Ar and —NH$_2$), 8.10 (d, 2H, J=8.8 Hz, Ar), 10.35 (s, 1H, —NH—).

Example 16

8-[4-[((4-Methylcarbamoyl)phenylcarbamoylmethyl)oxy]phenyl]-1,3-di-(n-propyl)xanthine (23)

A solution of 20 mg of compound 21 (0.0358 mmole) in 1 mL of 40% aqueous methylamine was stirred at room temperature for 1 hour. The mixture was evaporated to dryness under reduced pressure, and the residue was purified by preparative silica gel TLC (CHCl$_3$:MeOH=20:1) and re-crystallized in MeOH/CH$_2$Cl$_2$ to afford 9 mg of compound 23. $^1$H NMR (DMSO-d$_6$). 0.89 (2t, 6H, J=7.8 Hz, 2×—CH$_3$), 1.58 and 1.73 (2m, 4H, 2×—CH$_2$—), 2.76 (s, 3H, —NHCH$_3$) 3.86 and 4.01 (2t, 4H, J=6.8 Hz, 2×—NCH$_2$—), 4.82 (s, 2H, —OCH$_2$—), 7.14 (d, 2H, J=8.8 Hz, Ar), 7.71 (d, 2H, J=7.8 Hz, Ar), 7.81 (d, 2H, J=7.8 Hz, Ar), 8.09 (d, 2H, J=8.8 Hz, Ar), 8.33 (m, 1H, —NHCH$_3$), 10.34 (s, 1H, —NH—).

Example 17

8-[4-[((4-Carboxy)phenylcarbamoylmethyl)oxy]phenyl]-1,3-di-(n-propyl)xanthine (24)

A suspension of 20 mg of compound 21 (0.0385 mmole) in 1 mL of 1 N NaOH solution was stirred for 2 hours to turn to a clear solution. The mixture was neutralized by adding 1 mL of 1 N HCl solution. The precipitate was collected by filtration, and purified by low pressure (C18) column chromatography using linear gradient elution of 1 M triethylammonium acetate buffer (pH=7.0) and CH$_3$CN (90/10 to 40/60) to afford 10 mg of compound 24. $^1$H NMR (DMSO-d$_6$). 0.89 (2t, 6H, J=7.8 Hz, 2×—CH$_3$), 1.58 and 1.74 (2m, 4H, 2×—CH$_2$—), 3.87 and 4.01 (2t, 4H, J=6.8 Hz, 2×—NCH$_2$—), 4.84 (s, 2H, —OCH$_2$—), 7.14 (d, 2H, J=8.8 Hz, Ar), 7.77 (d, 2H, J=8.8 Hz, Ar), 7.92 (d, 2H, J=8.8 Hz, Ar), 8.09 (d, 2H, J=8.8 Hz, Ar), 10.45 (s, 1H, —NH—).

Example 18

8-[4-[((4-Cyano)phenylcarbamoylmethyl)oxy]phenyl]-1,3-di-(n-propyl)xanthine (27)

$^1$H NMR (DMSO-d$_6$). 0.89 (2t, 6H, J=7.8 Hz, 2×—CH$_3$), 1.58 and 1.74 (2m, 4H, 2×—CH$_2$—), 3.86 and 4.01 (2t, 4H, J=6.8 Hz, 2×—NCH$_2$—), 4.85 (s, 2H, —OCH$_2$—), 7.13 (d, 2H, J=8.8 Hz, Ar), 7.80 (d, 2H, J=7.8 Hz, Ar), 7.84 (d, 2H, J=7.8 Hz, Ar), 8.09 (d, 2H, J=8.8 Hz, Ar), 10.58 (s, 1H, —NH—).

Example 19

8-[4-[((4-Nitro)phenylcarbamoylmethyl)oxy]phenyl]-1,3-di-(n-propyl)xanthine (28)

$^1$H NMR (DMSO-d$_6$). 0.89 (2t, 6H, J=7.8 Hz, 2×—CH$_3$), 1.58 and 1.74 (2m, 4H, 2×—CH$_2$—), 3.87 and 4.02 (2t, 4H, J=6.8 Hz, 2×—NCH$_2$—), 4.89 (s, 2H, —OCH$_2$—), 7.15 (d, 2H, J=8.8 Hz, Ar), 7.91 (d, 2H, J=8.8 Hz, Ar), 8.10 (d, 2H, J=8.8 Hz, Ar), 8.26 (d, 2H, J=8.8 Hz, Ar), 10.76 (s, 1H, —NH—).

Example 20

8-[4-[((4-Trifluoromethyl)phenylcarbamoylmethyl)oxy]phenyl]-1,3-di-(n-propyl)xanthine (29)

$^1$H NMR (DMSO-d$_6$). 0.89 (2t, 6H, J=7.8 Hz, 2×—CH$_3$), 1.58 and 1.74 (2m, 4H, 2×—CH$_2$—), 3.87 and 4.02 (2t, 4H, J=6.8 Hz, 2×—NCH$_2$—), 4.85 (s, 2H, —OCH$_2$—), 7.15 (d, 2H, J=8.8 Hz, Ar), 7.71 (d, 2H, J =7.8 Hz, Ar), 7.87 (d, 2H, J=7.8 Hz, Ar), 8.09 (d, 2H, J=8.8 Hz, Ar), 10.51 (s, 1H, —NH—).

Example 21

8-[4-[((4-Fluoro)phenylcarbamoylmethyl)oxy]phenyl]-1,3-di-(n-propyl)xanthine (30)

$^1$H NMR (DMSO-d$_6$). 0.89 (2t, 6H, J=7.8 Hz, 2×—CH$_3$), 1.58 and 1.74 (2m, 4H, 2×—CH$_2$—), 3.87 and 4.02 (2t, 4H, J=6.8Hz, 2×—NCH$_2$—), 4.79 (s, 2H, —OCH$_2$—), 7.15 (d, 2H, J=8.8 Hz, Ar), 7.19 (d, 2H, J=8.8 Hz, Ar), 7.66 (dd, 2H, J=5.9, 8.8 Hz, Ar), 8.10 (d, 2H, J=8.8 Hz, Ar), 10.20 (s, 1H, —NH—).

Example 22

8-[4-[((4-Chloro)phenylcarbamoylmethyl)oxy]phenyl]-1,3-di-(n-propyl)xanthine (31)

$^1$H NMR (DMSO-d$_6$). 0.89 (2t, 6H, J=7.8 Hz, 2×—CH$_3$), 1.58 and 1.74 (2m, 4H, 2×—CH$_2$—), 3.87 and 4.02 (2t, 4H, J=6.8 Hz, 2×—NCH$_2$—), 4.80 (s, 2H, —OCH$_2$—), 7.14 (d, 2H, J=7.8 Hz, Ar), 7.39 (d, 2H, J=7.8 Hz, Ar), 7.68 (d, 2H, J=7.8 Hz, Ar), 8.09 (d, 2H, J=7.8 Hz, Ar), 10.27 (s, 1H, —NH—).

Example 23

8-[4-[((4-Bromo)phenylcarbamoylmethyl)oxy]phenyl]-1,3-di-(n-propyl)xanthine (32)

$^1$H NMR (DMSO-d$_6$). 0.89 (2t, 6H, J=7.8 Hz, 2×—CH$_3$), 1.58 and 1.74 (2m, 4H, 2×—CH$_2$—), 3.87 and 4.02 (2t, 4H, J=6.8 Hz, 2×—NCH$_2$—), 4.80 (s, 2H, —OCH$_2$—), 7.14 (d, 2H, J=8.8 Hz, Ar), 7.52 (d, 2H, J=8.8 Hz, Ar), 7.63 (d, 2H, J=8.8 Hz, Ar), 8.09 (d, 2H, J=8.8 Hz, Ar), 10.27 (s, 1H, —NH—).

Example 24

8-[4-[((4-Iodo)phenylcarbamoylmethyl)oxy]phenyl]-1,3-di-(n-propyl)xanthine (33)

$^1$H NMR (D)MSO-d$_6$). 0.89 (2t, 6H, J=7.8 Hz, 2×—CH$_3$), 1.58 and 1.74 (2m, 4H, 2×—CH$_2$—), 3.87 and 4.02 (2t, 4H, J=6.8 Hz, 2×—NCH$_2$—), 4.79 (s, 2H, —OCH$_2$—), 7.14 (d, 2H, J=7.8 Hz, Ar), 7.49 (d, 2H, J=7.8 Hz, Ar), 7.68 (d, 2H, J=7.8 Hz, Ar), 8.09 (d, 2H, J=7.8 Hz, Ar), 10.24 (s, 1H, —NH—).

Example 25

8-(4-(2-Carboxy-trans-vinyl)phenyl)-1,3-di-(n-propyl)xanthine N',N'-[(1,2-Dimethyl)maleyl]hydrizide (34)

$^1$H NMR (CDCl$_3$). 1.01 (2t, 6H, J=7.8 Hz, 2×—CH$_3$), 1.72 and 1.89 (2m, 4H, 2×—CH$_2$—), 2.05 (s, 6H, 2×—CH$_3$), 4.02 and 4.17 (2t, 4H, J=6.8 Hz, 2×—NCH$_2$—), 6.67 (d, 1H, J=15.6 Hz, —CH═), 7.63 (d, 2H, J=8.8 Hz, Ar), 7.74 (d, 1H, J=15.6 Hz, —CH═), 8.09 (d, 2H, J=8.8 Hz, Ar), 9.43 (s, 1H, —NH—).

Example 26

8-[4(2-(2-Acetylphenyl)carbamoyl-trans-vinyl)phenyl]-1,3-di-(n-propyl)xanthine (35)

$^1$H NMR (DMSO-d$_6$). 0.89 (2t, 6H, J=7.8 Hz, 2×—CH$_3$), 1.59 and 1.76 (2m, 4H, 2×—CH$_2$—), 3.88 and 4.04 (2t, 4H, J=6.8 Hz, 2×—NCH$_2$—), 4.79 (d, 3H, J=4.9 Hz, —COCH$_3$), 6.93 (d, 1H, J=15.6 Hz, —CH═), 7.51 (d, 1H, J=15.6 Hz, —CH═), 7.57 (t, 1H, J=7.8 Hz, Ar), 7.69 (t, 1H, J=7.8 Hz, Ar), 7.75 (d, 2H, J=7.8 Hz, Ar), 8.03 (d, 2H, J=7.8 Hz, Ar), 8.18 (d, 2H, J=7.8 Hz, Ar), 8.53 (t, 1H, J=5.8 Hz, —NH—).

Example 27

8-[4-(2-(2-Acetylphenyl)carbamoyl-trans-vinyl)phenyl]-1,3-di-(cyclohexylmethyl)xanthine (36)

$^1$H NMR (CDCl$_3$). 1.02–1.27 (m, 8H, c-Hex.), 1.45–1.72 (m, 14H, c-Hex.), 4.00 and 4.08 (2d, 4H, J=6.8 Hz, 2×—NCH$_2$—), 4.96 (d, 3H, J=3.9 Hz, —COCH$_3$), 6.66 (d, 1H, J=15.6 Hz, —CH═), 6.86 (bs, 1H, —NH—), 7.54 (t, 2H, J=7.8 Hz, Ar), 7.64–7.78 (m, 3H, —CH═and Ar), 8.06 (d, 2H, J=7.8 Hz, Ar), 8.24 (d, 2H, J=8.8 Hz, Ar).

Example 28

8-[4-(2-(2-Acetylphenyl)carbamoyl-trans-vinyl)phenyl]-1,3-dibenzylxanthine (37)

$^1$H NMR (DMSO-d$_6$) 4.79 (d, 3H, J=5.8 Hz, —COCH$_3$), 5.13 (s, 2H, —NCH$_2$—), 5.27 (s, 2H, —NCH$_2$—), 6.93 (d, 1H, J=15.6 Hz, —CH═), 7.24–7.41 (m, 10H, 2×-Ph), 7.46 (d, 1H, J=15.6 Hz, —CH═), 7.57 (t, 1H, J=8.8 Hz, Ar), 7.69 (t, 1H, J=7.8 Hz, Ar), 7.75 (d, 2H, J=8.8 Hz, Ar), 8.03 (d, 2H, J=7.8 Hz, Ar), 8.20 (d, 2H, J=7.8 Hz, Ar), 8.54 (t, 1H, J=5.8 Hz, —NH—).

Example 29

8-[4-[((2-Acetylphenyl)carbamoylmethyl)oxy]phenyl]-1,3-dibenzyl-xanthine (38)

$^1$H NMR (DMSO-d$_6$) 4.68 (s, 3H, —COCH$_3$), 4.71 (s, 2H, —OCH$_2$—), 5.12 (s, 2H, —NCH$_2$—), 5.26 (s, 2H, —NCH$_2$—), 7.15 (d, 2H, J=8.8 Hz, Ar), 7.23–7.42 (m, 10H, 2×-Ph), 7.55 (t, 1H, J=7.8 Hz, Ar), 7.68 (t, 1H, J=7.8 Hz, Ar), 8.02 (d, 2H, J=7.8 Hz, Ar), 8.11 (d, 2H, J=8.8 Hz, Ar), 8.48 (t, 1H, J=4.8 Hz, —NH—).

Example 30

8-[4-[(Carboxymethyl)oxy]phenyl]-1,3-di-(n-propyl)xanthine N-Acetylhydrazide (41)

$^1$H NMR (DMSO-d$_6$). 0.89 (2t, 6H, J=7.8 Hz, 2×—CH$_3$), 1.58 and 1.74 (2m, 4H, 2×—CH$_2$—), 1.88 (s, 3H, CH$_3$CO—), 3.87 and 4.02 (2t, 4H, J=6.8 Hz, 2×—NCH$_2$—), 4.68 (s, 2H, —OCH$_2$—), 7.11 (d, 2H, J=8.8 Hz, Ar), 8.08 (d, 2H, J=8.8 Hz, Ar); MS-FAB (M+H$^+$) 443.

Example 31

8-[4-[(Carboxymethyl)oxy]phenyl]-1,3-di-(n-propyl)xanthine N-[(3-Carboxy)-n-propionyl]hydrazide (42)

$^1$H NMR (DMSO-d$_6$). 0.89 (2t, 6H, J=7.8 Hz, 2×—CH$_3$), 1.58 and 1.74 (2m, 4H, 2×—CH$_2$—), 2.43 (m, 4H, —COCH$_2$CH$_2$CO—), 3.87 and 4.02 (2t, 4H, J=6.8 Hz, 2×—NCH$_2$—), 4.67 (s, 2H, —OCH$_2$—), 7.11 (d, 2H,J=8.8 Hz, Ar), 8.08 (d, 2H, J=8.8 Hz, Ar); MS-FAB (M+H$^+$) 501.

Example 32

8-[4-[(Carboxymethyl)oxy]phenyl]-1,3-di-(n-propyl)xanthine N,N-Succinylhydrazide (43)

$^1$H NMR (DMSO-d$_6$). 0.89 (2t, 6H, J=7.8 Hz, 2×—CH$_3$), 1.59 and 1.73 (2m, 4H, 2×—CH$_2$—), 2.81 (s, 4H, CH$_2$CH$_2$), 3.87 and 4.03 (2t, 4H, J=6.8 Hz, 2×—NCH$_2$—), 4.85 (s, 2H, —OCH$_2$—), 7.15 (d, 2H,J=8.8 Hz, Ar), 8.10 (d, 2H,J=8.8 Hz, Ar); MS-FAB (M+H$^+$) 483.

Example 33

8-[4-[(Carboxymethyl)oxy]phenyl]-1,3-di-(n-propyl)xanthine N,N-[((2S)-Trifluoroacetamido)succinyl]hydrazide (44)

$^1$H NMR (DMSO-d$_6$). 0.89 (2t, 6H, J=7.8 Hz, 2×—CH$_3$), 1.58 and 1.74 (2m, 4H, 2×—CH$_2$—), 2.70–2.90 (m, 2H, —CH$_2$—), 3.81 and 3.98 (2t, 4H, J=6.8 Hz, 2×—NCH$_2$—), 4.69 (s, 2H, —OCH$_2$—), 4.95 (s, 1H, —CH—), 7.15 (d, 2H, J=8.8 Hz, Ar), 8.10 (d, 2H, J=8.8Hz, Ar); MS-FAB (M+H$^+$) 594.

Example 34

8-[4-[(Carboxymethyl)oxy]phenyl]-1,3-di-(n-propyl) xanthine N,N-[(2-Phenyl)glutaryl]hydrazide (45)

$^1$H NMR (CDCl$_3$). 1.05 (2t, 6H, J=7.8 Hz, 2×—CH$_3$), 1.75 and 1.90 (2m, 4H, 2×—CH$_2$—), 2.3–2.5 and 2.8–3.1 (m, 5H, —CH— and 2×—CH$_2$—), 4.04 and 4.12 (2t, 4H, J=6.8 Hz, 2×—NCH$_2$—), 4.70–4.90 (m, 2H, —OCH$_2$—), 6.6 (d, 2H, J=8.8 Hz, Ar), 7.08 (m, 2H, -Ph), 7.43 (m, 5H, -Ph and Ar); MS-FAB (M+H$^+$) 573.

Example 35

8-[4-[(Carboxymethyl)oxy]phenyl]-1,3-di-(n-propyl) xanthine N,N-Citraconylhydrazide (46)

$^1$H NMR (DMSO-d$_6$). 0.89 (2t, 6H, J=7.8 Hz, 2×—CH$_3$), 1.59 and 1.73 (2m, 4H, 2×—CH$_2$—), 2.07 (s, 3H, CH$_3$), 3.87 and 4.03 (2t, 4H, J=6.8 Hz, 2×—NCH$_2$—), 4.86 (s, 2H, —OCH$_2$—), 6.83 (s, 1H, =CH—), 7.15 (d, 2H, J=8.8 Hz, Ar), 8.10 (d, 2H, J=8.8 Hz, Ar); MS-FAB (M+H$^+$) 495.

Example 36

8-[4-[(Carboxymethyl)oxy]phenyl]-1,3-di-(n-propyl) xanthine N,N-[(1,2-Dimethyl)maleyl]hydrazide (47)

$^1$H NMR (DMSO-d$_6$). 0.89 (2t, 6H, J=7.8 Hz, 2×—CH$_3$), 1.58 and 1.74 (2m, 4H, 2×—CH$_2$—), 1.97 (s, 6H, 2×—CH$_3$), 3.87 and 4.03 (2t, 4H, J=6.8 Hz, 2×—NCH$_2$—), 4.86 (s, 2H, —OCH$_2$—), 7.14 (d, 2H, J=8.8 Hz, Ar), 8.10 (d, 2H, J=8.8 Hz, Ar); MS-FAB (M+H$^+$) 509.

Example 37

8-[4-[(Carboxymethyl)oxy]phenyl]-1H-3-(n-propyl) xanthine N,N-1(1,2-Dimethyl)maleyl]hydrazide (48)

$^1$H NMR (DMSO-d$_6$). 0.91 (t, 3H, J=7.8 Hz, 2×—CH$_3$), 1.73 (m, 2H, —CH$_2$—), 1.97 (s, 6H, 2×—CH$_3$), 3.96 (t, 2H, J=6.8 Hz, 2×—NCH$_2$—), 4.85 (s, 2H, —OCH$_2$—), 7.14 (d, 2H, J=8.8 Hz, Ar), 8.09 (d, 2H, J=8.8 Hz, Ar); MS-EI (M$^+$) 509, Calcd. for C$_{22}$H$_{22}$N$_6$O$_6$ 466.1601; Found 466.1580.

Example 38

8-[4-[(Carboxymethyl)oxy]phenyl]-1,3-di-(n-propyl) xanthine N,N-[(2-Phenyl)maleyl]hydrazide (49)

$^1$H NMR (DMSO-d$_6$). 0.89 (2t, 6H, J=7.8 Hz, 2×—CH$_3$), 1.59 and 1.73 (2m, 4H, 2×—CH$_2$—), 3.87 and 4.03 (2t, 4H, J =6.8 Hz, 2×—NCH$_2$—), 4.91 (s, 2H, —OCH$_2$—), 7.15 (d, 2H, J=8.8 Hz, Ar), 7.51 (s, 1H, =CH—), 7.55–7.57 (m, 3H, -Ph), 8.04–8.06 (m, 2H, -Ph), 8.11 (d, 2H, J=8.8 Hz, Ar); MS-FAB (M+H$^+$) 557.

Example 39

8-[4-[(Carboxymethyl)oxy]phenyl]-1,3-di-(n-propyl) xanthine N,N-[(1,2-Diphenyl)maleyl]hydrazide (50)

$^1$H NMR (DMSO-d$_6$). 0.89 (2t, 6H, J=7.8 Hz, 2×—CH$_3$), 1.59 and 1.73 (2m, 4H, 2×—CH$_2$—), 3.87 and 4.03 (2t, 4H, J=6.8 Hz, 2×—NCH$_2$—), 4.94 (s, 2H, —OCH$_2$—), 7.15 (d, 2H, J=8.8 Hz, Ar), 7.45 (bs, 10H, 2×-Ph), 8.10 (d, 2H, J=8.8 Hz, Ar); MS-FAB (M+H$^+$) 633.

Example 40

8-[4-[(Carboxymethyl)oxy]phenyl]-1,3-di-(n-propyl) xanthine N-[2-((1-Carboxy)-cis-4-cyclohexene)-carbonyl]hydrazide (51)

$^1$H NMR (DMSO-d$_6$). 0.89 (2t, 6H, J=7.8 Hz, 2×—CH$_3$), 1.58 and 1.74 (2m, 4H, 2×—CH$_2$—), 2.30–2.50 (m, 4H, 2×—CH$_2$—), 2.80–2.95 (m, 2H, 2×—CH—), 3.83 and 3.90 (2t, 4H, J=6.8 Hz, 2×—NCH$_2$—), 4.66 (s, 2H, —OCH$_2$—), 5.63 (s, 2H, 2×=CH—), 7.09 (d, 2H, J=8.8 Hz, Ar), 8.06 (d, 2H, J=8.8 Hz, Ar); MS-FAB (M+H$^+$) 553.

Example 41

8-[4-[(Carboxymethyl)oxy]phenyl]-1,3-di-(n-propyl) xanthine N,N-(cis-1,2,3,6-Tetrahydrophthaloyl) hydrazide (52)

$^1$H NMR (DMSO-d$_6$). 0.89 (2t, 6H, J=7.8 Hz, 2×—CH$_3$), 1.58 and 1.74 (2m, 4H, 2×—CH$_2$—), 2.20–2.50 (m, 4H, 2×—CH$_2$—), 3.56 (m, 2H, 2×—CH—), 3.83 and 3.90 (2t, 4H, J=6.8 Hz, 2×—NCH$_2$—), 4.66 (s, 2H, —OCH$_2$—), 5.89 (s, 2H, 2×=CH—), 7.09 (d, 2H, J=8.8 Hz, Ar), 8.06 (d, 2H, J=8.8 Hz, Ar); MS-FAB (M+H$^+$) 535.

Example 42

8-[4-[(Carboxymethyl)oxy]phenyl]-1,3-di-(n-propyl) xanthine N-[2-((1-Carboxy)-1-cyclopentene)-carbonyl]hydrazide (53)

$^1$H NMR (DMSO-d$_6$). 0.89 (2t, 6H, J=7.8 Hz, 2×—CH$_3$), 1.58 and 1.74 (2m, 4H, 2×—CH$_2$—), 1.87 (m, 2H, —CH$_2$—), 2.70 (m, 4H, 2×—CH$_2$—), 3.83 and 3.90 (2t, 4H, J=6.8 Hz, 2×—NCH$_2$—), 4.71 (s, 2H, —OCH$_2$—), 7.09 (d, 2H, J=8.8 Hz, Ar), 8.06 (d, 2H, J=8.8 Hz, Ar); MS-FAB (M+H$^+$) 539.

Example 43

8-[4-[(Carboxymethyl)oxy]phenyl]-1,3-di-(n-propyl) xanthine N,N-(1-Cyclopentene-1,2-dicarbonyl) hydrazide (54)

$^1$H NMR (DMSO-d$_6$). 0.89 (2t, 6H, J=7.8 Hz, 2×—CH$_3$), 1.58 and 1.74 (2m, 4H, 2×—CH$_2$—), 2.40 (m, 2H, —CH1$_2$—), 2.67(4H, m, 2×—CH$_2$—), 3.81 and 3.98 (2t, 4H, J=6.8 Hz, 2×—NCH$_2$—), 4.85 (s, 2H, —OCH$_2$—), 7.15 (d, 2H, J=8.8 Hz, Ar), 8.1 (d, 2H, J 8.8 Hz, Ar); MS-FAB (M+H$^+$) 521.

Example 44

8-[4-[(Carboxymethyl)oxy]phenyl]-1,3-di-(n-propyl) xanthine N-[2-((1-Carboxy)-1-cyclohexene)-carbonyl]hydrazide (55)

$^1$H NMR (DMSO-d$_6$). 0.89 (2t, 6H, J=7.8 Hz, 2×—CH$_3$), 1.59 (m, 6H, 3×—CH$_2$—), 1.74 (m, 2H, —CH$_2$—), 2.27 (m, 4H, 2×—CH$_2$—), 3.87 and 4.02 (2t, 4H, J=6.8 Hz, 2×—NCH$_2$—), 4.68 (s, 2H, —OCH$_2$—), 7.09 (d, 2H, J=8.8 Hz, Ar), 8.06 (d, 2H, J=8.8 Hz, Ar); MS-FAB (M+H$^+$) 553.

Example 45

8-[4-[(Carboxymethyl)oxy]phenyl]-1,3-di-(n-propyl) xanthine N,N-(3,4,5,6-Tetrahydrophthaloyl) hydrazide (56)

$^1$H NMR (DMSO-d$_6$). 0.89 (2t, 6H, J=7.8 Hz, 2×—CH$_3$), 1.58 (m, 2H, —CH$_2$—), 1.72 (m, 6H, 3×—CH$_2$—), 2.30 (m, 4H, 2×—CH$_2$—) 3.83 and 3.90 (2t, 4H, J=6.8 Hz, 2×—NCH$_2$—), 4.86 (s, 2H, —OCH$_2$—), 7.15 (d, 2H, J=8.8 Hz, Ar), 8.12 (d, 2H, J=8.8 Hz, Ar); MS-FAB (M+H$^+$) 535.

Example 46

8-[4-[(Carboxymethyl)oxy]phenyl]-1,3-di-(n-propyl) xanthine N,N-Phthaloylhydrazide (57)

$^1$H NMR (DMSO-d$_6$). 0.89 (2t, 6H, J=7.8 Hz, 2×—CH$_3$), 1.58 and 1.74 (2m, 4H, 2×—CH$_2$—), 3.87 and 4.02 (2t, 4H, J=6.8 Hz, 2×—NCH$_2$—), 4.75 (s, 2H, —OCH$_2$—), 7.14 (d, 2H, J=8.8 Hz, Ar), 7.57 (m, 4H, Ar), 8.09 (d, 2H, J=8.8 Hz, Ar); MS-FAB (M+H$^+$) 531.

Example 47

8-[4-[(Carboxymethyl)oxy]phenyl]-1,3-di-(n-propyl) xanthine N,N-Glutarylhydrazide (58)

$^1$H NMR (CDCl$_3$). 1.05 (2t, 6H, J=7.8 Hz, 2×—CH$_3$), 1.75 and 1.90 (2m, 4H, 2×—CH$_2$—), 2.10–2.30 (m, 2H, —CH$_2$—), 2.80–3.10 (m, 4H, 2×—CH$_2$—), 4.05 and 4.16 (2t, 4H, J=6.8 Hz, 2×—NCH$_2$—), 4.80 (s, 2H, —OCH$_2$—), 6.75 (d, 2H, J=8.8 Hz, Ar), 7.70 (d, 2H, J=8.8 Hz, Ar); MS-FAB (M+H$^+$) 497.

Example 48

8-[4-[(Carboxymethyl)oxy]phenyl]-1,3-di-(n-propyl) xanthine N,N-(3-Hydroxy)glutarylhydrazide (59)

$^1$H NMR (DMSO-d$_6$). 0.89 (2t, 6H, J=7.8 Hz, 2×—CH$_3$), 1.59 and 1.73 (2m, 4H, 2×—CH$_2$—), 2.70–3.10 (m, 4H, 2×—CH$_2$—), 3.87 and 4.03 (2t, 4H, J=6.8 Hz, —NCH$_2$—), 4.21 (bs, 1H, —CHOH—), 4.77 (s, 2H, —OCH$_2$—), 7.15 (d, 2H, J=8.8 Hz, Ar), 8.1 (d, 2H, J=8.8 Hz, Ar); MS-FAB (M+H$^+$) 513.

Example 49

8-[4-[(Carboxymethyl)oxy]phenyl]-1,3-di-(n-propyl) xanthine N-[(4-Carboxy-(2S)-Trifluoroacetamido)-n-butanoyl]hydrazide (60)

A mixture of compound 4f (10 mg, 0.025 mmol), 7.6 mg of L-N-Boc-glutamic acid 5-tert-butyl ester (0.025 mmole), 7 mg of HOBt (0.05 mmole), 19 mg of DIPEA (0.15 mmole) and 15 mg of EDAC (0.078 mmole) in 1 mL of dry DMF was stirred for 8 hours at 25° C. The DMF was removed by nitrogen stream. The residue was washed with 1 mL of 1 M NaHCO$_3$ solution and dried overnight. The crude product was suspended in 0.5 mL of CHCl$_3$ and 0.5 mL of TFA added. After stirring for 30 minutes at 25° C., the mixture was concentrated to dryness and dried under high vacuum. The residue was dissolved in 0.5 mL of TFAA and the solution was stirred for 30 minutes at 25° C. The reaction mixture was concentrated to dryness, and the residue was purified by preparative TLC (CHCl$_3$:MeOH=10:1) to afford 6 mg of compound 60 as a white solid (yield 40%). $^1$H NMR (DMSO-d$_6$). 0.89 (2t, 6H, J=7.8 Hz, 2×—CH$_3$), 1.59 and 1.73 (2m, 4H, —CH$_2$—), 1.90–2.30 (m, 4H, 2×—CH$_2$—), 3.87 and 4.02 (2t, 4H, J=6.8 Hz, 2×—NCH$_2$—), 4.12 (m, 1H, —CH—), 4.68 (s, 2H, —OCH$_2$—), 7.08 (d, 2H, J=8.8 Hz, Ar), 8.06 (d, 2H, J=8.8 Hz, Ar); MS-FAB (M+H$^+$) 626.

Example 50

8-[4-[(Carboxymethyl)oxy]phenyl]-1,3-di-(n-propyl) xanthine N,N-((2S)-Trifluoroacetamido)glutaryl] hydrazide (61)

A mixture of compound 60 (10 mg, 0.016 mmol), 7 mg of HOBt (0.05 mmole), 19 mg of DIPEA (0.15 mmole) and 15 mg of EDAC (0.078 mmole) in 1 mL of dry DMF was stirred overnight at 25° C. The reaction mixture was concentrated to dryness, and the residue was purified by preparative TLC (CHCl$_3$:MeOH=10:1) to afford 5 mg of compound 61 as a white solid (yield 53%). $^1$H NMR (DMSO-d$_6$). 0.89 (2t, 6H, J=7.8 Hz, 2×—CH$_3$), 1.59 and 1.73 (2m, 4H, 2×—CH$_2$—), 1.90–2.30 (m, 4H, 2×—CH$_2$—), 3.87 and 4.02 (2t, 4H, J=6.8 Hz, 2×—NCH$_2$—), 4.81 (s, 2H, —OCH$_2$—), 4.18 (m, 1H, —CH—), 7.15 (d, 2H, J=8.8 Hz, Ar), 8.1 (d, 2H, J=8.8 Hz, Ar); MS-FAB (M+H$^+$) 608.

Example 51

8-[4-[(Carboxymethyl)oxy]phenyl]-1,3-di-(n-propyl) xanthine N-(N-tert-Butoxycarbonyl-L-leucinyl) hydrazide 62)

$^1$H NMR (DMSO-d$_6$). 0.89 (m, 13H, 2×—CH$_3$ and (CH$_3$)$_2$CH—), 1.35 (s, 9H, Boc), 1.42 (m, 2H, —CH$_2$—), 1.58 and 1.74 (2m, 4H, 2×—CH$_2$—), 3.85 and 4.0 (2t, 4H, J=6.8 Hz, 2×—NCH$_2$—), 4.12 (m, 1H, —CH—), 4.64 (s, 2H, —OCH$_2$—), 7.06 (d, 2H, J=8.8 Hz, Ar), 8.05 (d, 2H, J=8.8 Hz, Ar); MS-FAB (M+H$^+$) 614.

Example 52

8-[4-[(Carboxymethyl)oxy]phenyl]-1,3-di-(n-propyl) xanthine N-(N-tert-Butoxycarbonyl-L-methionyl) hydrazide (63)

$^1$H NMR (DMSO-d$_6$). 0.89 (2t, 6H, J=7.8 Hz, 2×—CH$_3$), 1.25 (m, 2H, —CH$_2$—), 1.37 (s, 9H, Boc), 1.58 and 1.74 (2m, 4H, 2×—CH$_2$—), 1.88 (m, 2H, —CH$_2$—, 2.03 (s, 3H, —SCH$_3$), 3.81 and 3.98 (2t, 4H, J=6.8 Hz, 2×—NCH$_2$—), 4.15 (m, 1H, —CH—), 4.68 (s, 2H, —OCH$_2$—), 7.03 (d, 2H, J=8.8 Hz, Ar), 8.03 (d, 2H, J=8.8 Hz, Ar); MS-FAB (M+H$^+$) 632.

Example 53

8-[4-[(Carboxymethyl)oxy]phenyl]-1,3-di-(n-propyl) xanthine N-(N-Benzyloxycarbonyl-glycylglycinyl) hydrazide (64)

$^1$H NMR (DMSO-d$_6$). 0.89 (2t, 6H, J=7.8 Hz, 2×—CH$_3$), 1.58 and 1.74 (2m, 4H, 2×—CH$_2$—), 3.67 (m, 1H, —CH$_2$— in glycine), 3.81 (m, 3H, —NCH$_2$— and —CH$_2$— in glycine), 3.98 (t, 2H, J=6.8 Hz, —NCH$_2$—), 4.64 (s, 2H, —OCH$_2$—), 5.03(s, 2H, —OCH$_2$-Ph), 7.03 (d, 2H, J=8.8 Hz, Ar), 7.3–7.5 (m, 5H, -Ph), 8.03 (d, 2H, J=8.8 Hz, Ar); MS-FAB (M+H$^+$) 649.

Example 54

8-[4-[(Carboxymethyl)oxy]phenyl]-1H-3-(n-propyl) xanthine Methyl Ester (65)

To a suspension of 3.2 g of 2,5-dioxo-4-amino-3-propyl tetrahydro pyrimidine, 66 [prepared according to the method described in Papesch et al., *J. Org. Chem.*, 16, 1879–1890 (1951)] (18.9 mmole), 1.5 mL of glacial acetic acid and 3.4 mL of 6 N HCl in 50 mL of water was added dropwise a solution of 1.38 g of sodium nitrite (20 mmole) in 5 mL of water at 0° C. The mixture was stirred for 1 hour and the pink precipitate was collected by filtration to afford 3.17 g of nitro-amine, 67 (yield 78%). $^1$H NMR (DMSO-d$_6$) 0.87 (t, 3H, J=7.8 Hz, —CH$_3$), 1.51 (m, 2H, —CH$_2$—), 3.72 (t, 2H, J=6.8 Hz, —NCH$_2$—), 9.12 (s, 11H, —NH$_2$).

0.086 g of nitro-amine, 67 (0.4 mmole) was hydrogenated with 10% Pd/C in 5 mL of MeOH under H$_2$ atmosphere (1 atm) at 25° C. until the pink color disappeared (30 min). After the removal of the balloon of $H_2$, 5 mL of DMF was added and the mixture was stirred for 10 min and filtered through a Celite bed.

To the solution of crude diamine, 68 was added 0.078 g of methyl 4-formylphenyloxyacetate (0.4 mmole) and 0.5 mL of acetic acid. The mixture was heated at 50° C. for 30 min, evaporated under reduced pressure and suspended in 20 mL of ether. The yellow precipitate (mixture of 69 and 65) was collected by filtration, dissolved in 5 mL of DMF and treated with 1 mL of aqueous solution of 0.085 g of sodium periodate (0.4 mmole) for 2 hours. After evaporation, the product was purified by crystallization in MeOH/$H_2O$ to afford 0.048 g of xanthine, 65 (yield 34%). 1H NMR (DMSO-$d_6$). 0.90 (t, 3H, J=7.8 Hz, —$CH_3$), 1.72 (m, 2H, —$CH_2$—), 3.71 (s, 3H, —$OCH_3$), 3.95 (t, 2H, J=6.8 Hz, —$NCH_2$—), 4.89 (s, 2H, —$OCH_2$—), 7.08 (d, 2H, J=8.8 Hz, Ar), 8.05 (d, 2H, J=8.8 Hz, Ar), 11.07 (s, 1H, —NH); MS-EI (M+) 358, Calcd. for $C_{17}H_{18}N_4O_5$ 358.1277; Found 358.1269.

Example 55

8-[4-[(Carboxymethyl)oxy]phenyl]-1H-3-(n-propyl) xanthine Hydrazide (70)

A solution of 0.05 g of xanthine 65 (0.14 mmole) and 0.5 mL of hydrazine anhydrous in 2 mL of dry DMF was heated overnight at 50° C. After evaporation, the residue was suspended in MeOH and the white precipitate was collected by filtration to give 0.025 g of 70 (yield 50%). m.p.=267° C.; $^1$H NMR (DMSO-$d_6$). 0.90 (t, 3H, J=7.8 Hz, —$CH_3$), 1.72 (m, 2H, —$CH_2$—), 3.71 (s, 3H, —$OCH_3$), 3.95 (t, 2H, J=6.8 Hz, —$NCH_2$—), 4.34 (bs, 2H, $NH_2$), 4.56 (s, 2H, —$OCH_2$—), 7.08 (d, 2H, J=8.8 Hz, Ar), 8.05 (d, 2H, J=8.8 Hz, Ar), 9.39 (s, 1H, —NH); MS-EI (M+) 358, Calcd. for $C_{16}H_{18}N_6O_4$ 358.1389; Found 358.1389.

Table 5 contains data for yields and characterization of the xanthine compounds of the invention. Table 6 contains data for elemental analysis of the xanthine compounds of the invention.

TABLE 5

The yields and chemical characterization of xanthine derivatives.

| Compound | % yield | m.p. (° C.) | MS | Formula | Analysis |
|---|---|---|---|---|---|
| 7 | 13 | >310 | EI:482 | $C_{27}H_{22}N_4O_5$ | HRMS[a] |
| 10 | 40 | >310 | FAB:479 | $C_{28}H_{22}N_4O_4$ | C,H,N |
| 12 | 71 | 301–302 | CI:462 | $C_{25}H_{27}N_5O_4$ | C,H,N |
| 13 | 41 | 268 | CI:476 | $C_{26}H_{29}N_5O_4$ | C,H,N |
| 14 | 46 | 269–270 | EI:551 | $C_{32}H_{33}N_5O_4$ | C,H,N |
| 15 | 55 | 230 | EI:565 | $C_{33}H_{35}N_5O_4$ | C,H,N |
| 16 | 49 | 215 | FAB:476 | $C_{26}H_{29}N_5O_4$ | C,H,N |
| 17 | 13 | 225 | CI:558 | $C_{27}H_{35}N_5O_8$ | C,H,N |
| 18 | 68 | 294 | EI:503 | $C_{27}H_{29}N_5O_5$ | C,H,N |
| 19 | 29 | 269–270 | EI:503 | $C_{27}H_{29}N_5O_5$ | HRMS[a] |
| 20 | 29 | 309–310 | EI:503 | $C_{27}H_{29}N_5O_5 \cdot 0.23H_2O$ | C,H,N |
| 21 | 56 | >310 | CI:520 | $C_{27}H_{29}N_5O_6$ | C,H,N |
| 22 | 19 | >310 | CI:505 | $C_{26}H_{28}N_6O_5$ | C,H,N |
| 23 | 45 | >310 | FAB:519 | $C_{27}H_{30}N_6O_5 \cdot 1.8CH_2Cl_2$ | C,H,N |
| 24 | 51 | >310 | FAB:506 | $C_{26}H_{27}N_5O_6 \cdot 0.60CH_2Cl_2$ | C,H,N |
| 27 | 44 | >310 | CI:487 | $C_{26}H_{26}N_6O_4$ | C,H,N |
| 28 | 31 | 307 | CI:507 | $C_{25}H_{26}N_6O_6 \cdot 0.43CH_3OH$ | C,H,N |
| 29 | 44 | >310 | CI:530 | $C_{26}H_{26}F_3N_5O_4 \cdot 0.26CH_3OH$ | C,H,N |
| 30 | 48 | 298 | CI:480 | $C_{25}H_{26}FN_5O_4$ | C,H,N |
| 31 | 31 | 309 | CI:496 | $C_{25}H_{26}ClN_5O_4 \cdot 0.26(CH_3)_2CO$ | C,H,N |
| 32 | 36 | >310 | CI:540 | $C_{25}H_{26}BrN_5O_4$ | C,H,N |
| 33 | 13 | >310 | CI:588 | $C_{25}H_{26}IN_5O_4 \cdot 0.60CH_3OH$ | C,H,N |
| 4c | 79 | >310 | FAB:509 | $C_{25}H_{28}N_6O_6$ | C,H,N |
| 34 | 49 | 302–303 | EI:504 | $C_{26}H_{28}N_6O_5$ | C,H,N |
| 35 | 42 | 281–283 | CI:500 | $C_{28}H_{29}N_5O_4 \cdot 0.27MeOH$ | C,H,N |
| 36 | 33 | 305 | FAB:608 | $C_{36}H_{41}N_5O_4$ | HRMS[a] |
| 37 | 76 | 308–309 | CI:596 | $C_{36}H_{29}N_5O_4 \cdot 0.60H_2O$ | C,H,N |
| 38 | 18 | 284 | EI:599 | $C_{35}H_{29}N_5O_5$ | HRMS[a] |

[a]) High-resolution mass in EI or FAB+ mode (m/z) determined to be within acceptable limits: 7: calcd, 482.1590; found, 482.1597, 19: calcd, 503.2169; found, 503.2169, 36: calcd, 608.3237; found, 608.3251; 38: calcd, 599.2169; found, 599.2171.

TABLE 6

Elemental Analysis of Xanthine Derivatives

| Compound No. | Formula | MW (anhyd) | Calculated (% or HRMS) | Found (% or HRMS) |
|---|---|---|---|---|
| 7 | $C_{27}H_{22}N_4O_5$ | 482.49 | 482.1590 | 482.1597 |
| 10 | $C_{28}H_{22}N_4O_4$ | 478.50 | C70.28, H4.63, N11.70 | C70.16, H4.72, N11.72 |
| 12 | $C_{25}H_{27}N_5O_4$ | 461.52 | C65.06, H5.90, N15.17 | C65.04, H5.93, N15.20 |
| 13 | $C_{26}H_{29}N_5O_4$ | 475.54 | C65.66, H6.15, N14.72 | C65.70, H6.22, N14.72 |
| 14 | $C_{32}H_{33}N_5O_4$ | 551.64 | C69.67, H6.03, N12.69 | C69.60, H6.08, N12.66 |
| 15 | $C_{33}H_{35}N_5O_4$ | 565.67 | C70.06, H6.24, N12.38 | C70.01, H6.33, N12.35 |
| 16 | $C_{26}H_{29}N_5O_4$ | 475.54 | C65.66, H6.15, N14.72 | C65.45, H6.23, N14.68 |
| 17 | $C_{27}H_{33}N_5O_8$ | 557.60 | C58.15, H6.33, N12.56 | C57.93, H6.38, N12.41 |

TABLE 6-continued

Elemental Analysis of Xanthine Derivatives

| Compound No. | Formula | MW (anhyd) | Calculated (% or HRMS) | Found (% or HRMS) |
|---|---|---|---|---|
| 18 | $C_{27}H_{29}N_5O_5$ | 503.55 | C64.40, H5.81, N13.90 | C64.24, H5.83, N13.87 |
| 19 | $C_{27}H_{29}N_5O_5$ | 503.55 | 503.2169 | 503.2169 |
| 20 | $C_{27}H_{29}N_5O_5$ | 503.55 | C64.40, H5.81, N13.90 | |
| | $C_{27}H_{29}N_5O_5 \cdot 0.23H_2O$ | 507.70 | C63.88, H5.85, N13.79 | C63.74, H5.77, N13.80 |
| 21 | $C_{27}H_{29}N_5O_6$ | 519.55 | C62.41, H5.63, N13.48 | C62.58, H5.67, N13.36 |
| 22 | $C_{26}H_{28}N_6O_5$ | 504.54 | C61.89, H5.59, N16.65 | C60.64, H5.66, N15.58 |
| 23 | $C_{27}H_{30}N_6O_5$ | 518.57 | C62.53, H5.83, N16.20 | |
| | $C_{27}H_{30}N_6O_5 \cdot 1.80CH_2Cl_2$ | 671.45 | C51.51, H5.04, N12.51 | C51.75, H4.92, N12.77 |
| 24 | $C_{26}H_{27}N_5O_6$ | 505.53 | C61.77, H5.38, N13.85 | |
| | $C_{26}H_{27}N_5O_6 \cdot 0.60CH_2Cl_2$ | 556.49 | C57.41, H5.11, N12.58 | C57.12, H5.18, N12.46 |
| 27 | $C_{26}H_{26}N_6O_4$ | 486.53 | C64.18, H5.39, N17.27 | C64.27, H5.47, N17.03 |
| 28 | $C_{25}H_{26}N_6O_5$ | 506.51 | C59.28, H5.17, N16.59 | |
| | $C_{25}H_{26}N_6O_6 \cdot 0.43CH_3OH$ | 520.30 | C58.70, H5.37, N16.15 | C58.63, H5.26, N15.98 |
| 29 | $C_{26}H_{26}F_3N_5O_4$ | 529.51 | C58.97, H4.95, N13.22 | |
| | $C_{26}H_{26}F_3N_5O_4 \cdot 0.26CH_3OH$ | 537.85 | C58.64, H5.07, N13.02 | C58.74, H5.07, N12.96 |
| 30 | $C_{25}H_{26}FN_5O_4$ | 479.51 | C62.62, H5.47, N14.60 | C62.39, H5.49, N14.31 |
| 31 | $C_{25}H_{26}ClN_5O_4$ | 495.96 | C60.54, H5.28, N14.12 | |
| | $C_{25}H_{26}ClN_5O_{4 \cdot 0.26(CH3)_2CO}$ | 511.07 | C60.59, H5.44, N13.70 | C60.59, H5.40, N13.62 |
| 32 | $C_{25}H_{26}BrN_5O_4$ | 540.41 | C55.56, H4.85, N12.95 | C55.28, N4.89, N12.70 |
| 33 | $C_{25}H_{26}IN_5O_4$ | 587.41 | C51.11, H4.46, N11.92 | |
| | $C_{25}H_{26}IN_5O_4 \cdot 0.60CH_3OH$ | 606.64 | C50.68, H4.72, N11.54 | C50.48, H4.40, N11.28 |
| 4c | $C_{25}H_{28}N_6O_6$ | 508.53 | C59.04, H5.55, N16.52 | C58.79, H5.50, N16.48 |
| 34 | $C_{26}H_{28}N_6O_5$ | 504.54 | C61.89, H5.59, N16.65 | C62.18, H5.86, N16.31 |
| 35 | $C_{28}H_{29}N_5O_4$ | 499.56 | C67.31, H5.85, N14.01 | |
| | $C_{28}H_{29}N_5O_4 \cdot 0.27MeOH$ | 508.22 | C66.81, H5.97, N13.78 | C66.73, H5.87, N13.61 |
| 36 | $C_{36}H_{41}N_5O_4$ | 607.75 | 608.3237 (M + H) | 608.3251 |
| 37 | $C_{36}H_{29}N_5O_4$ | 595.65 | C72.59, H4.91, N11.75 | |
| | $C_{36}H_{29}N_5O_4 \cdot 0.60H_2O$ | 606.47 | C71.30, H5.02, N11.55 | C71.48, H4.98, N11.45 |
| 38 | $C_{35}H_{29}N_5O_5$ | 599.64 | 599.2169 | 599.2171 |

Example 56

Prevention of Myocardial Necrosis Following Ninety Minute LAD Occlusion by 8-[4-[((4-Cyano)phenylcarbamoylmethyl)oxy]phenyl]-1,3-di-(n-propyl)xanthine (27)

The compounds of the invention were tested for their ability to block $A_{2B}$ receptors to show that mast cell degranulation can be reduced or prevented. In addition, this example shows that these antagonists could prevent or markedly attenuate the extent of myocardial infarction that occurred during coronary artery occlusion.

Figure 6:
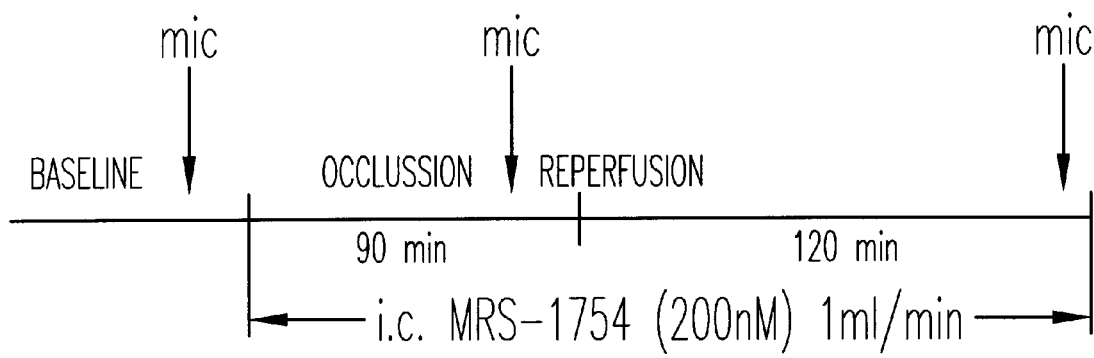
FIG. 6 illustrates the experimental protocol for the ninety minute cardiac left anterior descending (LAD) coronary artery occlusion/reperfusion test. Regional myocardial blood flow was measured at 30 second, 90 second, 3 minute, 5 minute, 8 minute, 13 minute, 23 minute, 38 minute, and 68 minute, intervals, using radioactive microspheres (mic), administered at the times indicated.

The left anterior descending (LAD) coronary artery of a group of dogs was isolated and encircled with a snare occluder. The dogs LAD artery blood supply was occluded for 90 minutes. The test solutions were administered intracoronary beginning immediately prior to the 90 minute occlusion interval and continued for two hours post-reperfusion (FIG. 6). One group of three dogs were administered a solution containing the (4-cyano)phenyl compound, prepared in Example 18, infused at a concentration of 200 nM at a rate of 1.0 mL/min. by intracoronary (i.c.) infusion into the LAD. A second group of four dogs were administered a solution containing the vehicle (carrier). Regional myocardial blood flow was measured at baseline, during LAD occlusion and for 2 hrs after reperfusion using radiolabeled microspheres (mic).

Figure 7:
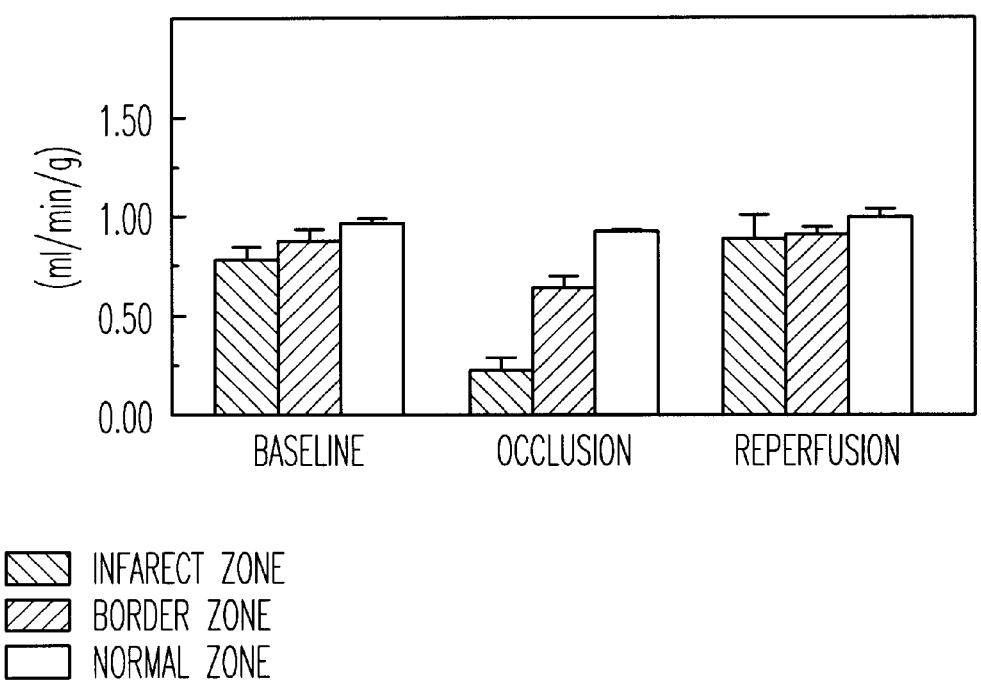
FIG. 7 illustrates the regional myocardial transmural blood flow in the central infarct (solid bar), border (open bar), and normal (striped bar) zones at baseline, during the LAD occlusion, and 2 hrs after reperfusion. During the total LAD occlusion, mean flow of test solution was <0.2 ml/min/g for 90 min.
Figure 8:
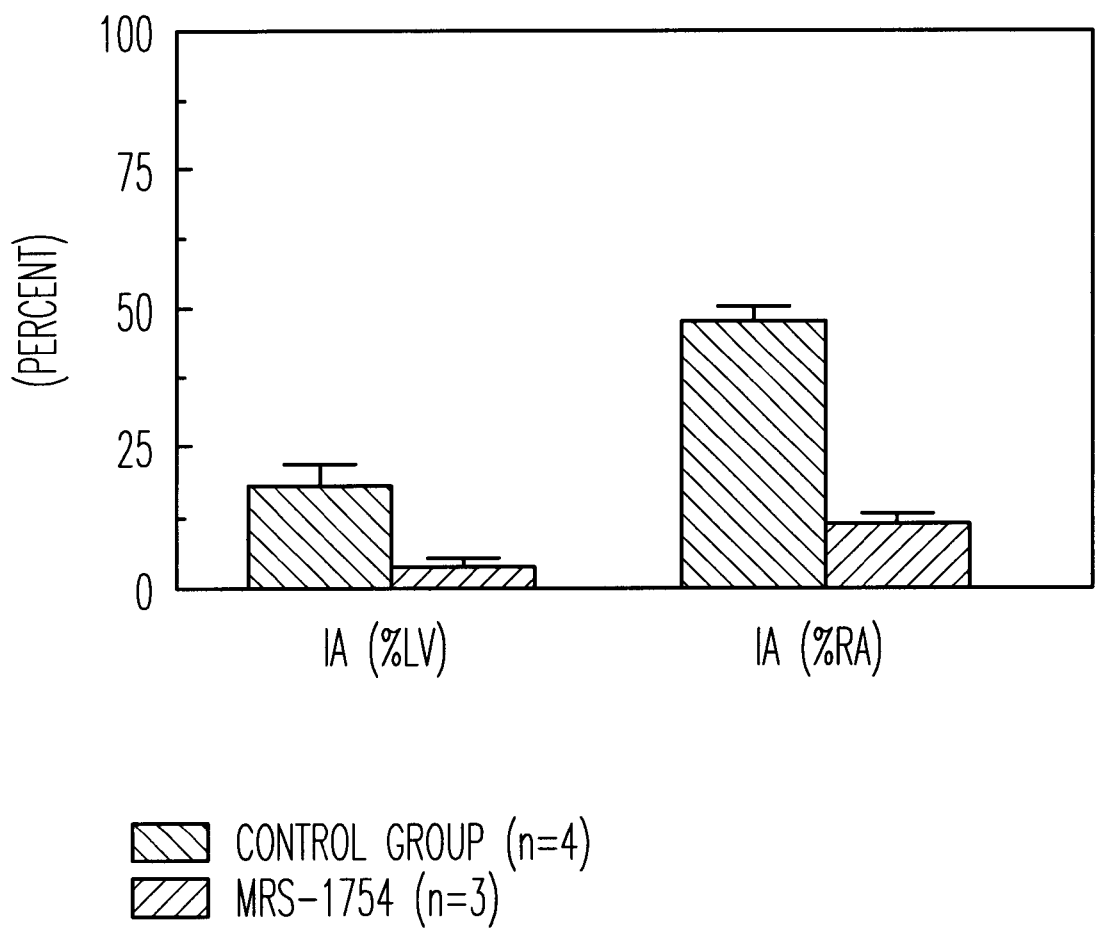
FIG. 8 illustrates the mean infarct size measured using triphenyl tetrazolium chloride (TTC) staining in vehicle-treated (control) dogs and in dogs treated with 8-[4-[((4-cyano)phenylcarbamoylmethyl)oxy]phenyl]-1,3-di-(n-propyl)xanthine (27). The p-cyanoanilide, 27, (200 nm) was infused intracoronary at a rate of 1 ml/min during occlusion and reperfusion. The treatment prevented or markedly attenuate the extent of myocardial infarction and significantly reduced the infarct area (IA), measured as % left ventricle area (%LV) or % area at risk (%RA).

The results are illustrated in FIGS. 7 and 8. These figures show that the infusion of the test compound during the 90 minute occlusion dramatically attenuated infarct size compared with dogs that were untreated.

All patents, patent applications, books and literature cited in the specification are hereby incorporated by reference in their entirety. In the case of any inconsistencies, the present disclosure, including any definitions therein will prevail.

The invention has been described with reference to various specific and preferred embodiments and techniques. However, it should be understood that many variations and modifications may be made while remaining within the spirit and scope of the invention.

What is claimed is:

1. A compound of formula I:

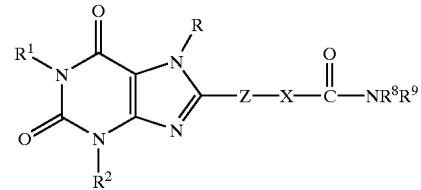

wherein R, and $R^1$ are independently hydrogen, $(C_1-C_8)$alkyl, $(C_2-C_8)$alkenyl, $(C_2-C_8)$alkynyl, $(C_1-C_8)$alkoxy, $(C_3-C_8)$cycloalkyl, $(C_4-C_{16})$cycloalkylalkyl, heterocycle, $(C_6-C_{10})$aryl, $(C_7-C_{18})$aralkyl or heteroaryl;

Z is 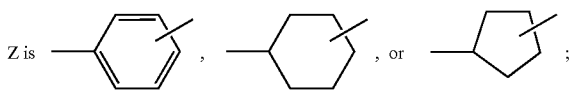

X is $(C_1-C_8)$alkylene, $(C_2-C_8)$alkenylene, $(C_2-C_8)$alkynylene, wherein one of the carbon atoms in the alkylene, alkenylene or alkynylene groups is optionally replaced with a group having the formula —O—, —N(R$^4$)C(O)—, —OC(O)—, —S—, —S(O)— or —SO$_2$—, $R^2$ is hydrogen, $(C_1-C_8)$alkyl, $(C_2-C_8)$alkenyl, $(C_2-C_8)$alkynyl, $(C_1-C_8)$alkoxy, $(C_3-C_8)$cycloalkyl, $(C_4-C_{16})$cycloalkylalkyl, $(C_6-C_{10})$aryl, $(C_7-C_{18})$aralkyl, heterocycle or heteroaryl; wherein $R^2$ is optionally substituted with one or more substituents selected from the group consisting of —OH, —SH, —NH$_2$, —NHR$^7$, —CN, —COOH and —SO$_3$H, wherein $R^4$, and $R^7$ are independently hydrogen, $(C_1-C_8)$alkyl, $(C_2-C_8)$alkenyl, $(C_3-C_8)$cycloalkyl, $(C_6-C_{10})$aryl, $(C_7-C_{18})$aralkyl or halo$(C_1-C_6)$alkyl; and wherein $R^8$ is hydrogen, $(C_3-C_8)$cycloalkyl, $(C_4-C_{16})$cycloalkylalkyl, $(C_7-C_{18})$aralkyl, heterocycle or heteroaryl, each optionally substituted with one or more substituents, wherein the substituents independently are oxo, $(C_1-C_8)$alkyl, halo$(C_1-C_6)$alkyl, $(C_2-C_8)$alkenyl, $(C_6-C_{10})$aryl, $(C_7-C_{18})$aralkyl, heteroaryl, halo, —OR$^{15}$, —CN, —NO$_2$, —CO$_2$R$^{15}$, —OC(O)R$^{16}$, —C(O)R$^{16}$, —NR$^{13}$R$^{14}$, —N(R$^{23}$)C(O)R$^{24}$, —C(O)NR$^{17}$R$^{18}$, —SR$^{19}$, —SO$_2$R$^{20}$ or —SO$_3$H; or $R^8$ is $(C_6-C_{10})$aryl, substituted with one or more substituents independently selected from the group consisting of $(C_1-C_8)$alkyl, halo$(C_1-C_6)$alkyl, $(C_2-C_8)$alkenyl, $(C_7-C_{18})$aralkyl, heteroaryl, —OR$^{15}$, —CN, —NO$_2$, —CO$_2$R$^{15}$, —OC(O)R$^{16}$, —C(O)R$^{16}$, —NR$^{13}$R$^{14}$, —N(R$^{23}$)C(O)R$^{24}$, —C(O)NR$^{17}$R$^{18}$, —SR$^{19}$, —SO$_2$R$^{20}$ and —SO$_3$H; and wherein $R^9$ is $(C_3-C_8)$cycloalkyl, $(C_4-C_{16})$cycloalkylalkyl, heterocycle or heteroaryl, each optionally substituted with one or more substituents, wherein the substituents independently are oxo, $(C_1-C_8)$alkyl, halo$(C_1-C_6)$alkyl, $(C_2-C_8)$alkenyl, $(C_6-C_{10})$aryl, $(C_7-C_{18})$aralkyl, heteroaryl, —OR$^{15}$, halo, —CN, —NO$_2$, CO$_2$R$^{15}$, —OC(O)R$^{16}$, —C(O)R$^{16}$, —NR$^{13}$R$^{14}$, —N(R$^{23}$)C(O)R$^{24}$, —C(O)NR$^{17}$R$^{18}$, —SR$^{19}$, —SO$_2$R$^{20}$ or —SO$_3$H; or $R^9$ is $(C_6-C_{10})$aryl, substituted with one or more substituents independently selected from the group consisting of $(C_1-C_8)$alkyl, halo$(C_1-C_6)$alkyl, $(C_2-C_8)$alkenyl, $(C_7-C_{18})$aralkyl, heteroaryl, —OR$^{15}$, —CN, —NO$_2$, O$_2$R$^{15}$, —OC(O)R$^{16}$, —C(O)R$^{16}$, —NR$^{13}$R$^{14}$, —N(R$^{23}$)C(O)R$^{24}$, —C(O)NR$^{17}$R$^{18}$, —SR$^{19}$, and —SO$_2$R$^{20}$, and wherein $R^{13}$, $R^{14}$, $R^{15}$, $R^{16}$, $R^{17}$, $R^{18}$, $R^{19}$, $R^{20}$, $R^{23}$ and $R^{24}$ are independently hydrogen $(C_1-C_8)$alkyl, $(C_2-C_8)$alkenyl, $(C_3-C_8)$cycloalkyl, $(C_6-C_8)$aryl, $(C_7-C_{18})$aralkyl or halo$(C_1-C_6)$alkyl;

provided that when R and $R^8$ are both H, and $R^1$ and $R^2$ are both alkyl, $R^9$ is not methylphenyl or hydroxyphenyl; or a pharmaceutically acceptable salt thereof.

2. The compound according to claim 1, wherein R and $R^1$ are independently hydrogen, $(C_1-C_6)$alkyl, $(C_2-C_6)$alkenyl, $(C_2-C_6)$alkynyl, $(C_1-C_6)$alkoxy, $(C_5-C_6)$cycloalkyl, $(C_6-C_{10})$cycloalkylalkyl, heterocycle, $(C_6)$aryl, $(C_7-C_{10})$aralkyl or heteroaryl;

X is $(C_{1-6})$alkylene, $(C_2-C_6)$alkenylene, $(C_2-C_6)$alkynylene, wherein one of the carbon atoms in the alkylene, alkenylene or alkynylene groups is optionally replaced with a group having the formula —O—, —N(R$^4$)C(O)—, —OC(O)—, —S—, —S(O)— or —SO$_2$—;

$R^2$ is hydrogen, $(C_1-C_4)$alkyl, $(C_2-C_4)$alkenyl, $(C_2-C_4)$alkynyl, $(C_1-C_4)$alkoxy, $(C_5-C_6)$cycloalkyl, $(C_6-C_{10})$cycloalkylalkyl, $(C_6)$aryl, $(C_7-C_{10})$aralkyl or a heterocycle;

wherein $R^4$, and $R^7$ are independently hydrogen, $(C_1-C_4)$alkyl, $(C_2-C_4)$alkenyl, $(C_5-C_6)$cycloalkyl, $(C_6)$aryl, $(C_7-C_{10})$aralkyl or halo$(C_1-C_6)$alkyl groups; and wherein $R^8$ is hydrogen, $(C_3-C_6)$cycloalkyl, $(C_3-C_{10})$cycloalkylalkyl, $(C_7-C_{10})$aralky heterocycle or heteroaryl, each optionally substituted with one or more substituents, wherein the substituents independently are oxo, $(C_1-C_6)$alkyl, halo$(C_1-C_6)$alkyl, $(C_2-C_6)$alkenyl, $(C_6)$aryl, $(C_7-C_{10})$aralkyl, heteroaryl, halo, —OR$^{15}$, —CN, —NO$_2$, —CO$_2$R$^{15}$, —OC(O)R$^{16}$, —C(O)R$^{16}$, —NR$^{13}$R$^{14}$, —N(R$^{23}$)C(O)R$^{24}$, —C(O)NR$^{17}$R$^{18}$, —SR$^{19}$, —SO$_2$R$^{20}$ or —SO$_3$H; or $R^8$ is $(C_6-C_{10})$aryl, substituted with one or more substituents independently selected from the group consisting of $(C_1-C_6)$alkyl, halo$(C_1-C_6)$alkyl, $(C_2-C_6)$alkenyl, $(C_7-C_{10})$aralkyl, heteroaryl, halo, —OR$^{15}$, —CN, —NO$_2$, —CO$_2$R$^{15}$, —OC(O)R$^{16}$, —C(O)R$^{16}$, —NR$^{13}$R$^{14}$, —N(R$^{23}$)C(O)R$^{24}$, —C(O)NR$^{17}$R$^{18}$, —SR$^{19}$, —SO$_2$R$^{20}$ and —SO$_3$H; or $R^9$ is $(C_3-C_6)$cycloalkyl, $(C_4-C_{10})$cycloalkylalkyl, heterocycle or heteroaryl, each optionally substituted with one or more substituents, wherein the substituents independently are oxo, $(C_1-C_6)$alkyl, halo$(C_1-C_6)$alkyl, $(C_2-C_6)$alkenyl, $(C_6)$aryl, $(C_7-C_{10})$aralkyl, heteroaryl, halo, —OR$^{15}$, —CN, —NO$_2$, —CO$_2$R$^{15}$, —OC(O)R$^{16}$, —C(O)R$^{16}$, —NR$^{13}$R$^{14}$, —N(R$^{23}$)C(O)R$^{24}$, —C(O)NR$^{17}$R$^{18}$, —SR$^{19}$, —SO$_2$R$^{20}$ or —SO$_3$H; or $R^9$ is $(C_6-C_{10})$aryl, substituted with one or more substituents independently selected from the group consisting of $(C_1-C_6)$alkyl, halo$(C_1-C_6)$alkyl, $(C_2-C_6)$alkenyl, $(C_7-C_{10})$aralkyl, heteroaryl, halo, —OR$^{15}$, —CN, —NO$_2$, —CO$_2$R$^{15}$, —OC(O)R$^{16}$, —C(O)R$^{16}$, —NR$^{13}$R$^{14}$, —N(R$^{23}$)C(O)R$^{24}$, —C(O)NR$^{17}$R$^{18}$, —SR$^{19}$, and —SO$_2$R$^{20}$.

3. The compound according to claim 2, wherein R, $R^1$ and $R^2$ are independently hydrogen, $(C_1-C_4)$alkyl, $(C_2-C_4)$alkenyl, $(C_2-C_4)$alkynyl, $(C_1-C_4)$alkoxy, $(C_5-C_6)$cycloalkyl, $(C_6-C_{10})$cycloalkylalkyl, $(C_6)$aryl, or $(C_7-C_{10})$aralkyl;

Z is 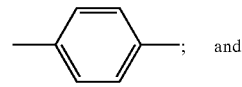 ; and

X is O—$(C_1-C_7)$alkylene, O—$(C_2-C_7)$alkenylene, $(C_1-C_8)$alkylene or $(C_2-C_8)$alkenylene;

wherein $R^9$ is $(C_3-C_6)$cycloalkyl, $(C_4-C_{10})$cycloalkylalkyl, heterocycle or heteroaryl, each optionally substituted with one or more substituents, wherein the substituents independently are oxo, $(C_1-C_6)$alkyl, halo$(C_1-C_6)$alkyl, $(C_2-C_6)$alkenyl, $(C_6)$aryl, $(C_7-C_{10})$aralkyl, heteroaryl, halo, —OR$^{15}$, —CN, —NO$_2$, —CO$_2$R$^{15}$, —OC(O)R$^{16}$, —C(O)R$^{16}$, —NR$^{13}$R$^{14}$, —N(R$^{23}$)C(O)R$^{24}$, —C(O)NR$^{17}$R$^{18}$, —SR$^{19}$, —SO$_2$R$^{20}$ or —SO$_3$H; or $R^9$ is $(C_6-C_{10})$aryl, substituted with one or more substituents independently selected from the group consisting of $(C_1-C_6)$alkyl, halo$(C_1-C_6)$alkyl, $(C_2-C_6)$alkenyl, $(C_7-C_{10})$aralkyl, heteroaryl, halo, —OR$^{15}$, —CN, —NO$_2$, —CO$_2$R$^{15}$, —OC(O)R$^{16}$, —C(O)R$^{16}$, —NR$^{13}$R$^{14}$, —N(R$^{23}$)C(O)R$^{24}$, —C(O)NR$^{17}$R$^{18}$, —SR$^{19}$, and —SO$_2$R$^{20}$.

4. A compound of formula I:

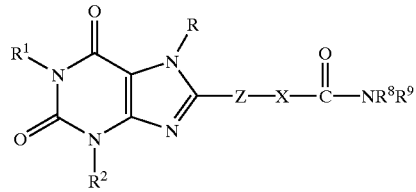

I

R is hydrogen, (C$_1$–C$_4$)alkyl, (C$_2$–C$_4$)alkenyl, (C$_2$–C$_4$) alkynyl, (C$_1$–C$_4$)alkoxy, (C$_5$–C$_6$)cycloalkyl, (C$_6$–C$_{10}$) cycloalkylalkyl, (C$_6$)aryl, or (C$_7$–C$_{10}$)aralkyl;

R$^1$ and R$^2$ are independently —CH$_2$CH$_3$, —CH$_2$CH=CH$_2$, —CH$_2$CH$_2$CH$_3$ or cyclohexylmethyl; and wherein —Z—X— is

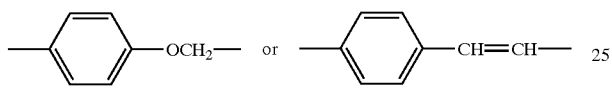

R$^8$ is hydrogen or (C$_7$–C$_{18}$)aralkyl, optionally substituted with one or more substituents, wherein the substituents independently are oxo, (C$_1$–C$_8$)alkyl, halo(C$_1$–C$_6$) alkyl, (C$_2$–C$_8$)alkenyl, (C$_6$–C$_{10}$)aryl, (C$_7$–C$_{18}$)aralkyl, heteroaryl, halo, —OR$^{15}$, —CN, —NO$_2$, —CO$_2$R$^{15}$, —OC(O)R$^{16}$, —C(O)R$^{16}$, —NR$^{13}$R$^{14}$, —N(R$^{23}$)C(O) R$^{24}$, —C(O)NR$^{17}$R$^{18}$, —SR$^{19}$, —SO$_2$R$^{20}$ or —SO$_3$H; or R$^8$ is (C$_6$–C$_{10}$)aryl: wherein the aryl is substituted with one or more substituents independently selected from the group consisting of (C$_1$–C$_8$)alkyl, halo(C$_1$–C$_6$) alkyl, (C$_2$–C$_8$)alkenyl, (C$_7$–C$_{18}$)aralkyl, heteroaryl, —OR$^{15}$, —CN, —NO$_2$, —CO$_2$R$^{15}$, —OC(O)R$^{16}$, —C(O)R$^{16}$, —NR$^{13}$R$^{14}$, —N(R$^{23}$)C(O)R$^{24}$, —C(O) R$^{17}$R$^{18}$, —SR$^{19}$, —SO$_2$R$^{20}$ and —SO$_3$H;

R$^9$ is

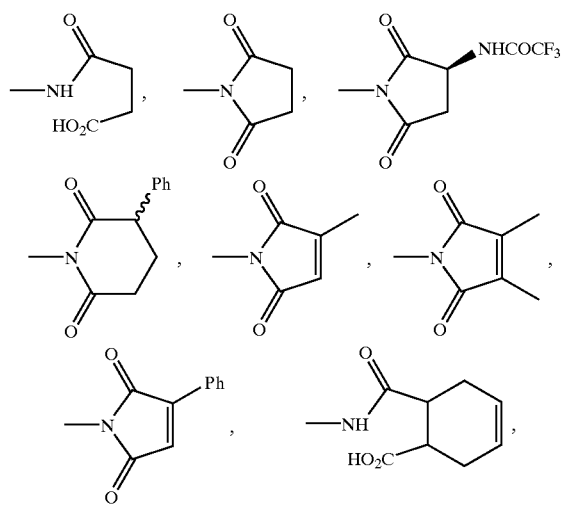

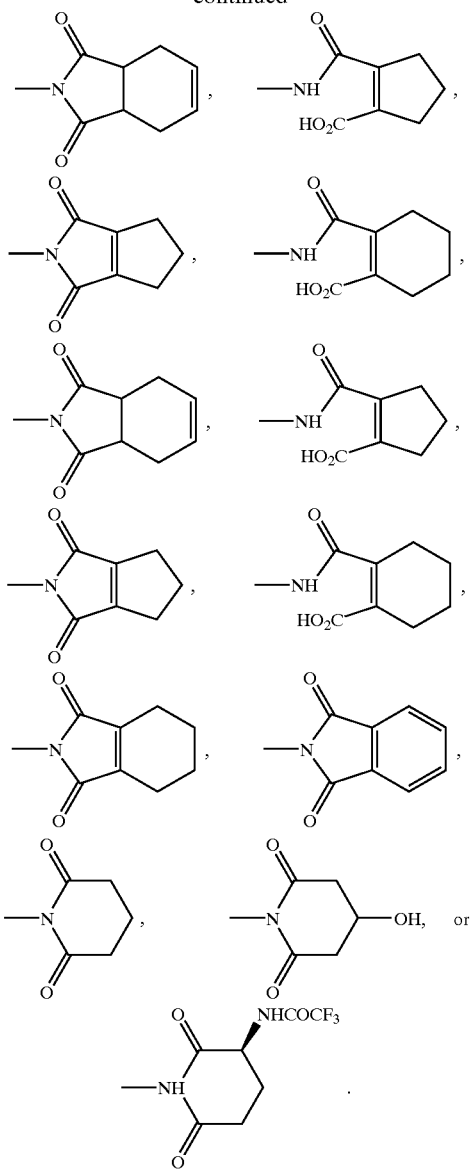

5. The compound according to claim 3, wherein —Z—X— is

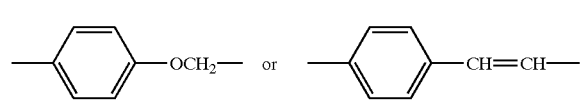

R$^1$ and R$^2$ are independently —CH$_2$CH$_3$, —CH$_2$CH=CH$_2$, —CH$_2$CH$_2$CH$_3$ or cyclohexylmethyl.

6. The compound according to claim 5, wherein aryl is phenyl and aralkyl is benzyl.

7. The compound according to claim 6, wherein R$^9$ is phenyl substituted with 1–3 substituents that are independently trifluoromethyl, 2,2,2-trifluoroethyl, pentafluoroethyl, (C$_1$–C$_4$)alkyl, (C$_2$–C$_4$)alkenyl, benzyl, F, Cl, Br, I, —CN, —NO$_2$, —CO$_2$R$^{15}$, —C(O)R$^{16}$, —NR$^{13}$R$^{14}$ or —C(O)NR$^{17}$R$^{18}$.

8. The compound according to claim 7, wherein R$^8$ is hydrogen and R$^9$ is phenyl substituted with 1–3 substituents that are independently F, Cl, Br, I, —CN, —COOH, —C(O)OCH₃, —C(O)CH₂CH₃, —C(O)CH₃, —C(O)NH₂ or —C(O)NHCH₃.

9. The compound according to claim 5, wherein —NR⁸R⁹ is

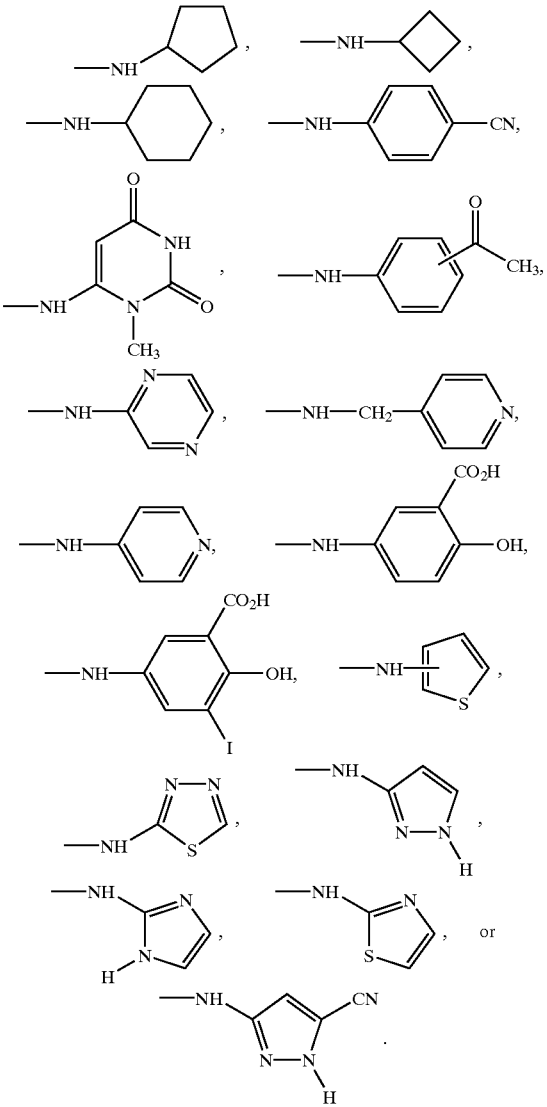

10. The compound according to claim 9, wherein R is H, R¹ and R² are each —CH₂CH=CH₂, and R⁹ is 4-cyanophenyl.

11. The compound according to claim 9, wherein R is H, R¹ and R² are each —CH₂CH₂CH₃, and R⁹ is 3-carboxy-4-hydroxyphenyl or 3-acetylphenyl.

12. A pharmaceutical composition comprising a compound of formula I:

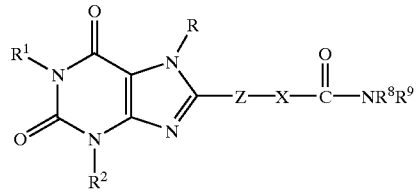

wherein R, is hydrogen, (C₁–C₄)alkyl, (C₂–C₄)alkenyl, (C₂–C₄)alkynyl, (C₁–C₄)alkoxy, (C₅–C₆)cycloalkyl, (C₆–C₁₀)cycloalkylalkyl, (C₆)aryl, or (C₇–C₁₀)aralkyl;
wherein —Z—X— is

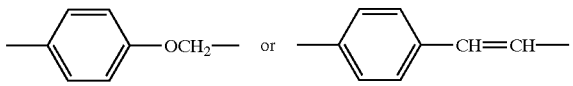

R⁸ is hydrogen or (C₇–C₁₈)aralkyl, optionally substituted with one or more substituents, wherein the substituents independently are oxo, (C₁–C₈)alkyl, halo(C₁–C₆)alkyl, (C₂–C₈)alkenyl, (C₆–C₁₀)aryl, (C₇–C₁₈)aralkyl, heteroaryl, halo, —OR¹⁵, —CN, —NO₂, —CO₂R¹⁵, —OC(O)R¹⁶, —C(O)R¹⁶, —NR¹³R¹⁴, —N(R²³)C(O)R²⁴, —C(O)NR¹⁷R¹⁸, —SR¹⁹, —SO₂R²⁰ or —SO₃H; or R⁸ is (C₆–C₁₀)aryl: wherein the aryl is substituted with one or more substituents independently selected from the group consisting of (C₁–C₈)alkyl, halo(C₁–C₆)alkyl, (C₂–C₈)alkenyl, (C₇–C₁₈)aralkyl, heteroaryl, —OR¹⁵, —CN, —NO₂, —CO₂R¹⁵, —OC(O)R¹⁶, —C(O)R¹⁶, —NR¹³R¹⁴, —N(R²³)C(O)R²⁴, —C(O)NR¹⁷R¹⁸, —SR¹⁹, —SO₂R²⁰ and —SO₃H;

R⁹ is

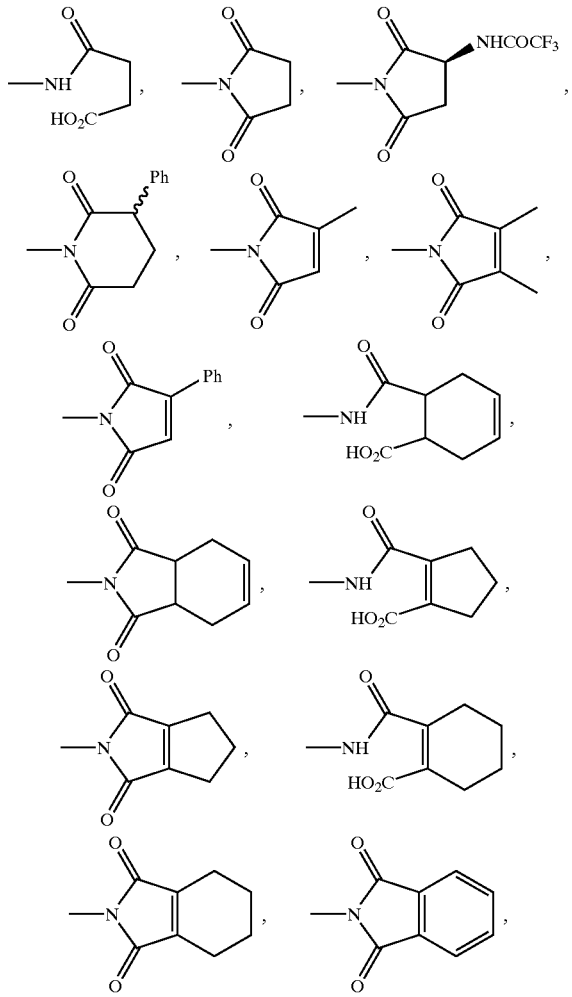

-continued

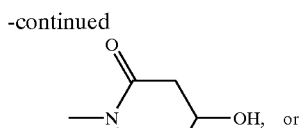

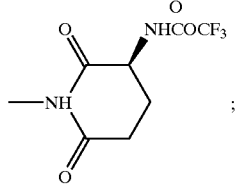

or a pharmaceutically acceptable salt thereof in combination with a pharmaceutically acceptable carrier.

13. A method for treating diarrhea, insulin resistance, diabetes, ischemia/reprefusion injuries, diabetic retinopathy or hyperbaric oxygen-induced retinopathy, comprising administering an effective amount of a compound of formula I:

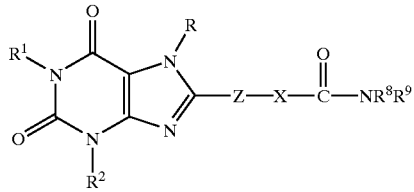

wherein R, and $R^1$ are independently hydrogen, $(C_1–C_8)$alkyl, $(C_2–C_8)$alkenyl, $(C_2–C_8)$alkynyl, $(C_{1-8})$alkoxy, $(C_3–C_8)$cycloalkyl, $(C_4–C_6)$cycloalkylalkyl, heterocycle, $(C_6–C_{10})$aryl, $(C_7–C_{18})$aralkyl or heteroaryl;

Z is 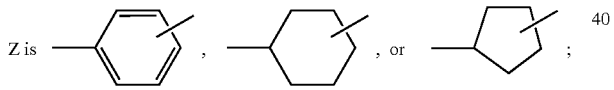

X is $(C_1–C_8)$alkylene, $(C_2–C_8)$alkenylene, $(C_2–C_8)$alkynylene, wherein one of the carbon atoms in the alkylene, alkenylene or alkynylene groups is optionally replaced with a group having the formula —O—, —N(R⁴)C(O)—, —OC(O)—, —S—, —S(O)— or —SO₂—, $R^2$ is hydrogen, $(C_1–C_8)$alkyl, $(C_2–C_8)$alkenyl, $(C_2–C_8)$alkynyl, $(C_1–C_8)$alkoxy, $(C_3–C_8)$cycloalkyl, $(C_4–C_{16})$cycloalkylalkyl, $(C_6–C_{10})$aryl, $(C_7–C_{18})$aralkyl, heterocycle or heteroaryl; wherein $R^2$ is optionally substituted with one or more substituents selected from the group consisting of —OH, —SH, —NH₂, —NHR⁷, —CN, —COOH and —SO₃H, wherein $R^4$, and $R^7$ are independently hydrogen, $(C_1–C_8)$alkyl, $(C_2–C_8)$alkenyl, $(C_3–C_8)$cycloalkyl, $(C_6–C_{10})$aryl, $(C_7–C_{18})$aralkyl or halo$(C_1–C_6)$alkyl; and wherein $R^8$ is hydrogen, $(C_3–C_8)$cycloalkyl, $(C_4–C_{16})$cycloalkylalkyl, $(C_7–C_{18})$aralkyl, heterocycle or heteroaryl, each optionally substituted with one or more substituents, wherein the substituents independently are oxo, $(C_1–C_8)$alkyl, halo$(C_1–C_6)$alkyl, $(C_2–C_8)$alkenyl, $(C_6–C_{10})$aryl, $(C_7–C_{18})$aralkyl, heteroaryl, halo, —OR¹⁵, —CN, —NO₂, —CO₂R¹⁵, —OC(O)R¹⁶, —C(O)R¹⁶, —NR¹³R¹⁴, —N(R²³)C(O)R²⁴, —C(O)NR¹⁷R¹⁸, —SR¹⁹, —SO₂R²⁰ or —SO₃H; or $R^8$ is $(C_6–C_{10})$aryl, substituted with one or more substituents independently selected from the group consisting of $(C_1–C_8)$alkyl, halo$(C_1–C_6)$alkyl, $(C_2–C_8)$alkenyl, $(C_7–C_{18})$aralkyl, heteroaryl, —OR¹⁵, —CN, —NO₂, —CO₂R¹⁵, —OC(O)R¹⁶, —OC(O)R¹⁶, —NR¹³R¹⁴, —N(R²³)C(O)R²⁴, —C(O)NR¹⁷R¹⁸, —SR¹⁹, —SO₂R²⁰ and —SO₃H; and wherein $R^9$ is $(C_3–C_8)$cycloalkyl, $(C_4–C_{16})$cycloalkylalkyl, heterocycle or heteroaryl, each optionally substituted with one or more substituents, wherein the substituents independently are oxo, $(C_1–C_8)$alkyl, halo$(C_1–C_6)$alkyl, $(C_2–C_8)$alkenyl, $(C_6–C_{10})$aryl, $(C_7–C_{18})$aralkyl, heteroaryl —OR¹⁵, halo, —CN, —NO₂, —CO₂R¹⁵, —OC(O)R¹⁶, —C(O)R¹⁶, —NR¹³R¹⁴, —N(R²³)C(O)R²⁴, —C(O)NR¹⁷R¹⁸, —SR¹⁹, —SO₂R²⁰ or —SO₃H; or $R^9$ is $(C_6–C_{10})$aryl, substituted with one or more substituents independently selected from the group consisting of $(C_1–C_8)$alkyl, halo$(C_1–C_6)$alkyl, $(C_2–C_8)$alkenyl, $(C_7–C_{18})$aralkyl, heteroaryl, —OR¹⁵, —CN, —NO₂, —CO₂R¹⁵, —OC(O)R¹⁶, —C(O)R¹⁶, —NR¹³R¹⁴, —N(R²³)C(O)R²⁴, —C(O)NR¹⁷R¹⁸, —SR¹⁹, and —SO₂R²⁰;

or a pharmaceutically acceptable salt thereof to a mammal in need of such treatment.

14. A method for antagonizing adenosine $A_{2B}$ receptors in mammalian tissue comprising contacting the receptors with an effective amount of a compound of claim 1 or 4 wherein the amount is effective to antagonize the adenosine $A_{2B}$ receptors in the tissue.

15. The compound of claim 1 or 4, wherein one of the atoms of said compound is replaced by its radionuclide.

16. The compound of claim 15, wherein the radionuclide is tritium, or radioactive iodine.

17. A pharmaceutical composition comprising a compound of formula I:

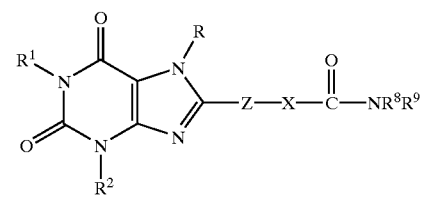

wherein R, and $R^1$ are independently hydrogen, $(C_1–C_8)$alkyl, $(C_2–C_8)$alkenyl, $(C_2–C_8)$alkynyl, $(C_{1-8})$alkoxy, $(C_3–C_8)$cycloalkyl, $(C_4–C_{16})$cycloalkylalkyl, heterocycle, $(C_6–C_{10})$aryl, $(C_7–C_{18})$aralkyl or heteroaryl;

Z is 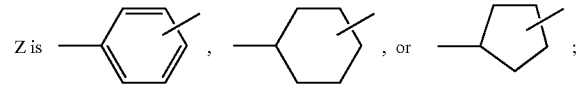

X is $(C_1–C_8)$alkylene, $(C_2–C_8)$alkenylene, $(C_2–C_8)$alkynylene, wherein one of the carbon atoms in the alkylene, alkenylene or alkynylene groups is optionally replaced with a group having the formula —O—, —N(R⁴)C(O)—, —OC(O)—, —S—, —S(O)— or —SO₂—, $R^2$ is hydrogen, $(C_1–C_8)$alkyl, $(C_2–C_8)$alkenyl, $(C_2–C_8)$alkynyl, $(C_1–C_8)$alkoxy, $(C_3–C_8)$cycloalkyl, $(C_4–C_{16})$ cycloalkylalkyl, ($C_6$–$C_{10}$)aryl, ($C_7$–$C_{18}$)aralkyl, heterocycle heteroaryl; wherein $R^2$ is optionally substituted with one or more substituents selected from the group consisting of —OH, —SH, —$NH_2$, —$NHR^7$, —CN, —COOH and —$SO_3H$, wherein $R^4$, and $R^7$ are independently hydrogen ($C_1$–$C_8$) alkyl, ($C_2$–$C_8$)alkenyl, ($C_3$–$C_8$)cycloalkyl, ($C_6$–$C_{10}$) aryl, ($C_7$–$C_{18}$)aralkyl or halo($C_1$–$C_6$)alkyl; and wherein $R^8$ is hydrogen, ($C_3$–$C_8$)cycloalkyl, ($C_4$–$C_{16}$) cycloalkylalkyl, ($C_7$–$C_{18}$)aralkyl, heterocycle or heteroaryl, each optionally substituted with one or more substituents, wherein the substituents independently are oxo, ($C_1$–$C_8$)alkyl, halo($C_1$–$C_6$)alkyl, ($C_2$–$C_8$)alkenyl, ($C_6$–$C_{10}$)aryl, ($C_7$–$C_{18}$)aralkyl, heteroaryl, halo, —$OR^{15}$, —CN, —$NO_2$, —$CO_2R^{15}$, —$OC(O)R^{16}$, —$C(O)R^{16}$, —$NR^{13}R^{14}$, —$N(R^{23})C(O)R^{24}$, —$C(O)NR^{17}R^{18}$, —$SR^{19}$, —$SO_2R^{20}$ or —$SO_3H$; or $R^8$ is ($C_6$–$C_{10}$)aryl, substituted with one or more substituents independently selected from the group consisting of ($C_1$–$C_8$)alkyl, halo($C_1$–$C_6$)alkyl, ($C_2$–$C_8$)alkenyl, ($C_7$–$C_{18}$)aralkyl, heteroaryl, —$OR^{15}$, —CN, —$NO_2$, —$CO_2R^{15}$, —$OC(O)R^{16}$, —$C(O)R^{16}$, —$NR^{13}R^{14}$, —$N(R^{23})C(O)R^{24}$, $C(O)NR^{17}R^{18}$, —$SR^{19}$, —$SO_2R^{20}$ and —$SO_3H$; and wherein $R^9$ is ($C_3$–$C_8$)cycloalkyl, ($C_4$–$C_{16}$) cycloalkylalkyl, heterocycle or heteroaryl, each optionally substituted with one or more substituents, wherein the substituents independently are oxo, ($C_1$–$C_8$)alkyl, halo($C_1$–$C_6$)alkyl, ($C_2$–$C_8$)alkenyl, ($C_6$–$C_{10}$)aryl, ($C_7$–$C_{18}$)aralkyl, heteroaryl, —$OR^{15}$, halo, —CN, —$NO_2$, —$CO_2R^{15}$, —$OC(O)R^{16}$, —$OC(O)R^{16}$, —$NR^{13}R^{14}$, —$N(R^{23})C(O)R^{24}$, —$C(O)NR^{17}R^{18}$, —$SR^{19}$, —$SO_2R^{20}$ or —$SO_3H$; or $R^9$ is ($C_6$–$C_{10}$)aryl, substituted with one or more substituents independently selected from the group consisting of ($C_1$–$C_8$)alkyl, halo($C_1$–$C_6$)alkyl, ($C_2$–$C_8$)alkenyl, ($C_7$–$C_{18}$)aralklyl, heteroaryl, —$OR^{15}$, —CN, —$NO_2$, —$C_2R^{15}$, —$OC(O)R^{16}$, —$C(O)R^{16}$, —$NR^{13}R^{14}$, —$N(R^{23})C(O)R^{24}$, —$C(O)NR^{17}R^{18}$, —$SR^{19}$, and —$SO_2R^{20}$, and wherein $R^{13}$, $R^{14}$, $R^{15}$, $R^{16}$, $R^{17}$, $R^{18}$, $R^{19}$, $R^{20}$, $R^{23}$ and $R^{24}$ are independently hydrogen, ($C_1$–$C_8$)alkyl, ($C_2$–$C_8$)alkenyl, ($C_3$–$C_8$)cycloalkyl, ($C_6$–$C_{10}$)aryl, ($C_7$–$C_{18}$)aralkyl or halo($C_1$–$C_6$)alkyl;

provided that when R and $R^8$ are both H, and $R^1$ and $R^2$ are both alkyl, $R^9$ is not methylphenyl or hydroxyphenyl; or a pharmaceutically acceptable salt thereof in combination with a pharmaceutically acceptable carrier.

18. The composition according to claim 17, wherein R and $R^1$ are independently hydrogen, ($C_1$–$C_6$)alkyl, ($C_2$–$C_6$) alkenyl, ($C_2$–$C_6$)alkynyl, ($C_1$–$C_6$)alkoxy, ($C_5$–$C_6$) cycloalkyl, ($C_6$–$C_{10}$)cycloalkylalkyl, heterocycle, ($C_6$)aryl, ($C_7$–$C_{10}$)aralkyl or heteroaryl;

X is ($C_1$–$C_6$)alkylene, ($C_2$–$C_6$)alkenylene, ($C_2$–$C_6$) alkynylene, wherein one of the carbon atoms in the alkylene, alkenylene or alkynylene groups is optionally replaced with a group having the formula —O—, —$N(R^4)C(O)$—, —OC(O)—, —S—, —S(O)— or —$SO_2$—;

$R^2$ is hydrogen, ($C_1$–$C_4$)alkyl, ($C_2$–$C_4$)alkenyl, ($C_2$–$C_4$) alkynyl, ($C_1$–$C_4$)alkoxy, ($C_5$–$C_6$)cycloalkyl, ($C_6$–$C_{10}$) cycloalkylalkyl, ($C_6$)aryl, ($C_7$–$C_{10}$)aralkyl or a heterocycle;

wherein $R^4$, and $R^7$ are independently hydrogen, ($C_1$–$C_4$) alkyl, ($C_2$–$C_4$)alkenyl, ($C_5$–$C_6$)cycloalkyl, ($C_6$)aryl, ($C_7$–$C_{10}$)aralkyl or halo($C_1$–$C_6$)alkyl groups; and wherein $R^8$ is hydrogen, ($C_3$–$C_6$)cycloalkyl, ($C_4$–$C_{10}$) cycloalkylalkyl, ($C_7$–$C_{10}$)aralkyl, heterocycle or heteroaryl, each optionally substituted with one or more substituents, wherein the substituents independently are oxo, ($C_1$–$C_6$)alkyl, halo($C_1$–$C_6$)alkyl, ($C_2$–$C_6$)alkenyl, ($C_6$)aryl, ($C_7$–$C_{10}$)aralkyl, heteroaryl, halo, —$OR^{15}$, —CN, —$NO_2$, —$CO_2R^{15}$, —$OC(O)R^{16}$, —$C(O)R^{16}$, —$NR^{13}R^{14}$, —$N(R^{23})C(O)R^{24}$, —$C(O)NR^{17}R^{18}$, —$SR^{19}$, —$SO_2R^{20}$ or —$SO_3H$; or $R^8$ is ($C_6$–$C_{10}$)aryl, substituted with one or more substituents independently selected from the group consisting of ($C_1$–$C_6$)alkyl, halo($C_1$–$C_6$)alkyl, ($C_2$–$C_6$)alkenyl, ($C_7$–$C_{10}$)aralkyl, heteroaryl, halo, —$OR^{15}$, —CN, —$NO_2$, —$CO_2R^{15}$, —$OC(O)R^{16}$, —$C(O)R^{16}$, —$NR^{13}R^{14}$, —$N(R^{23})C(O)R^{24}$, —$C(O)NR^{17}R^{18}$, —$SR^{19}$, —$SO_2R^{20}$ and —$SO_3H$; or $R^9$ is ($C_3$–$C_6$)cycloalkyl, ($C_4$–$C_{10}$)cycloalkylalkyl, heterocycle or heteroaryl, each optionally substituted with one or more substituents, wherein the substituents independently are oxo, ($C_1$–$C_6$)alkyl, halo($C_1$–$C_6$) alkyl, ($C_2$–$C_6$)alkenyl, ($C_6$)aryl, ($C_7$–$C_{18}$)aralkyl, heteroaryl, halo, —$OR^{15}$, —CN, —$NO_2$, —$CO_2R^{15}$, —$OC(O)R^{16}$, —$C(O)R^{16}$, —$NR^{13}R^{14}$, —$N(R^{23})C(O)R^{24}$, —$C(O)NR^{17}R^{18}$, —$SR^{19}$, —$SO_2R^{20}$ or —$SO_3H$; or $R^9$ is ($C_6$–$C_{10}$)aryl, substituted with one or more substituents independently selected from the group consisting of ($C_1$–$C_6$)alkyl, halo($C_1$–$C_6$)alkyl, ($C_2$–$C_6$)alkenyl, ($C_7$–$C_{10}$)aralkyl, heteroaryl, halo, —$OR^{15}$, —CN, —$NO_2$, —$CO_2R^{15}$, —$OC(O)R^{16}$, —$C(O)R^{16}$, —$NR^{13}R^{14}$, —$N(R^{23})C(O)R^{24}$, —$C(O)NR^{17}R^{18}$, —$SR^{19}$, and —$SO_2R^{20}$.

19. The composition according to claim 18, wherein R, $R^1$ and $R^2$ are independently hydrogen, ($C_1$–$C_4$)alkyl, ($C_2$–$C_4$) alkenyl, ($C_2$–$C_4$)alkynyl, ($C_1$–$C_4$)alkoxy, ($C_5$–$C_6$) cycloalkyl, ($C_6$–$C_{10}$)cycloalkylalkyl, ($C_6$)aryl, or ($C_7$–$C_{10}$) aralkyl;

Z is 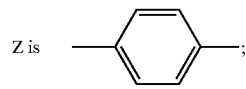 ;

X is O—($C_1$–$C_7$)alkylene, O—($C_2$–$C_7$)alkenylene, ($C_1$–$C_8$)alylene or ($C_2$–$C_8$)alkenylene;

wherein $R^9$ is ($C_3$–$C_6$)cycloalkyl, ($C_4$–$C_{10}$)cycloalkylalkyl, heterocycle or heteroaryl each optionally substituted with one or more substituents, wherein the substituents independently are oxo, ($C_1$–$C_6$)alkyl, halo($C_1$–$C_6$) alkyl, ($C_2$–$C_6$)alkenyl, ($C_6$)aryl, ($C_7$–$C_{10}$)aralkyl, heteroaryl, halo, —$OR^{15}$, —CN, —$NO_2$, —$CO_2R^{15}$, —$OC(O)^{16}$, —$C(O)R^{16}$, —$NR^{13}$ $R^{14}$, —$N(R^{23})C(O)R^{24}$, —$C(O)NR^{17}R^{18}$, —$SR^{19}$, —$SO_2R^{20}$ or —$SO_3H$; or $R^9$ is ($C_6$–$C_{10}$)aryl, substituted with one or more substituents independently selected from the group consisting of ($C_{1–6}$)alkyl, halo($C_1$–$C_6$)alkyl, ($C_2$–$C_6$)alkenyl, ($C_7$–$C_{10}$)aralkyl, heteroaryl, halo, —$OR^{15}$, —CN, —$NO_2$, —$CO_2R^{15}$, —$OC(O)R^{16}$, —$C(O)R^{16}$, —$NR^{13}R^{14}$, —$N(R^{23})C(O)R^{24}$, —$C(O)NR^{17}R^{18}$, —$SO_2R^{20}$.

20. The composition according to claim 19, wherein —Z—X— is

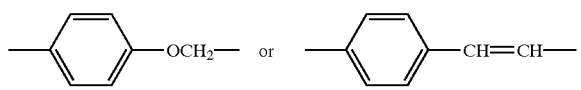

and $R^1$ and $R^2$ are independently —$CH_2C_3$, —$CH_2CH=CH$, —$CH_2CH_2CH_3$ or cyclohexylmethyl.

21. The composition according to claim 20, wherein aryl is phenyl and aralkyl is benzyl.

22. The composition according to claim 21, wherein $R^9$ is phenyl substituted with 1–3 substituents that are independently trifluoromethyl, 2,2,2-trifluoroethyl, pentafluoroethyl, alkenyl, benzyl, F, Cl, Br, I, —CN, —$NO_2$, —$CO_2R^{15}$, —$C(O)R^{16}$, —$NR^{13}R^{14}$ or —$C(O)NR^{17}R^{18}$.

23. The composition according to claim 22, wherein $R^8$ is hydrogen and $R^9$ is phenyl substituted with 1–3 substituents that are independently F, Cl, Br, I, —CN, —COOH, —$CO_2CH_3$, —$C(O)CH_2CH_3$, —$C(O)CH_3$, —$C(O)NH_2$ or —$C(O)NHCH_3$.

24. The composition according to claim 20, wherein —$NR^8R^9$ is:

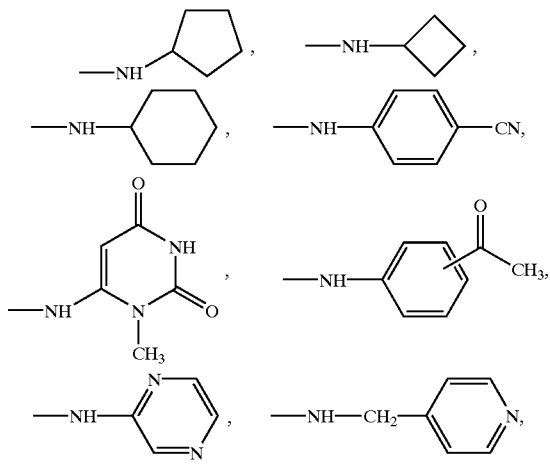

25. The composition according to claim 24, wherein R and $R^8$ are each H, $R^1$ and $R^2$ are each —$CH_2CH=CH_2$, and $R^9$ is 4-cyanophenyl.

26. The composition according to claim 25, wherein R and $R^8$ are each H, $R^1$ and $R^2$ are each —$CH_2CH_2CH_3$, and $R^9$ is 3-carboxy-4-hydroxyphenyl or 3-acetylphenyl.

27. A method for treating asthma comprising administering an effective amount of a compound of claim 1 or 4 to a mammal in need of such treatment.

* * * * *